(12) United States Patent
Schlessinger et al.

(10) Patent No.: US 6,861,442 B1
(45) Date of Patent: Mar. 1, 2005

(54) PYK2 AND INFLAMMATION

(75) Inventors: Joseph Schlessinger, New York, NY (US); Mitsuhiko Okigaki, New York, NY (US); Mikhail Gishizky, Menlo Park, CA (US)

(73) Assignees: Sugen, Inc., South San Francisco, CA (US); New York University, New York, NY (US)

( * ) Notice: Subject to any disclaimer, the term of this patent is extended or adjusted under 35 U.S.C. 154(b) by 0 days.

(21) Appl. No.: 09/476,484

(22) Filed: Dec. 30, 1999

Related U.S. Application Data

(60) Provisional application No. 60/114,465, filed on Dec. 30, 1998.

(51) Int. Cl.[7] .............................................. A01N 43/38
(52) U.S. Cl. ....................... 514/414; 514/312; 514/311; 514/546; 514/419; 514/450; 514/235.8; 514/227.5; 514/514; 514/229.8; 514/418; 435/7.4; 435/15; 424/94.1
(58) Field of Search ................................ 514/414, 312, 514/311, 546, 419, 450, 235.8, 227.5, 514, 229.8, 418; 435/252.3, 7.32, 7.4; 424/94.1, 95, 85.4, 85.5, 93.71

(56) References Cited

U.S. PATENT DOCUMENTS

| | | | |
|---|---|---|---|
| 3,691,016 A | | 9/1972 | Patel |
| 3,969,287 A | | 7/1976 | Jaworek et al. |
| 4,195,128 A | | 3/1980 | Hildebrand et al. |
| 4,215,051 A | | 7/1980 | Schroeder et al. |
| 4,229,537 A | | 10/1980 | Hodgins et al. |
| 4,247,642 A | | 1/1981 | Hirohara et al. |
| 4,330,440 A | | 5/1982 | Ayers et al. |
| 4,343,940 A | | 8/1982 | Kreighbaum et al. |
| 4,376,110 A | | 3/1983 | David et al. |
| 4,444,752 A | * | 4/1984 | Prudden ...................... 424/95 |
| 4,447,608 A | | 5/1984 | Jones et al. |
| 4,757,072 A | | 7/1988 | Kabbe et al. |
| 4,945,050 A | | 7/1990 | Sanford et al. |
| 4,946,778 A | | 8/1990 | Ladner et al. |
| 5,084,462 A | * | 1/1992 | Ackerman et al. ........... 514/311 |
| 5,242,932 A | * | 9/1993 | Gandy et al. ................ 514/313 |
| 5,296,353 A | * | 3/1994 | Ochoa et al. ............... 435/7.32 |
| 5,316,553 A | | 5/1994 | Kaul et al. |
| 5,580,882 A | * | 12/1996 | Abramsky et al. ........... 514/312 |
| 5,714,493 A | * | 2/1998 | Myers et al. ................. 514/259 |
| 5,731,343 A | * | 3/1998 | Feng et al. ................... 514/450 |
| 5,804,396 A | * | 9/1998 | Plowman .................... 435/7.23 |
| 5,834,504 A | * | 11/1998 | Tang et al. |
| 5,837,524 A | * | 11/1998 | Schlessinger et al. .... 435/252.3 |
| 5,837,815 A | * | 11/1998 | Lev et al. .................... 530/350 |
| 5,849,742 A | * | 12/1998 | App et al. .................... 514/249 |
| 5,854,285 A | * | 12/1998 | Sriram et al. ................ 514/514 |
| 5,856,331 A | * | 1/1999 | Bursten et al. .............. 514/263 |
| 5,880,141 A | * | 3/1999 | Tang et al. ................... 514/339 |
| 5,932,573 A | * | 8/1999 | Yuen ........................ 514/229.8 |
| 5,972,598 A | * | 10/1999 | Chaudhary et al. ............. 435/6 |
| 5,981,523 A | * | 11/1999 | Panetta et al. ............. 514/227.5 |
| 5,985,926 A | * | 11/1999 | Leung et al. ................. 514/558 |
| 6,015,812 A | * | 1/2000 | Ferrari et al. ............. 514/235.8 |
| 6,077,851 A | * | 6/2000 | Bjork et al. .................. 514/312 |
| 6,114,371 A | * | 9/2000 | Tang et al. ................... 514/414 |
| 6,121,287 A | * | 9/2000 | Bjork et al. .................. 514/312 |
| 6,143,764 A | * | 11/2000 | Kubo et al. .................. 514/312 |
| 6,147,106 A | * | 11/2000 | Tang et al. ................... 514/414 |
| 6,214,873 B1 | * | 4/2001 | Adachi et al. .............. 514/546 |
| 6,235,769 B1 | * | 5/2001 | Clary .......................... 514/419 |

FOREIGN PATENT DOCUMENTS

| | | | |
|---|---|---|---|
| EP | 516297 A1 | * 12/1992 | .......... A61K/31/50 |
| EP | 0 520 722 B1 | 12/1992 | |
| EP | 0 562 734 B1 | 9/1993 | |
| GB | 2202145 A | * 9/1988 | ......... A61K/31/395 |
| WO | WO 93/09236 A1 | 5/1993 | |
| WO | WO 93/23569 A1 | 11/1993 | |
| WO | WO 96/18738 A2 | 6/1996 | |
| WO | 96/18738 | * 6/1996 | ........... C12N/15/54 |
| WO | WO 96/22976 A1 | 8/1996 | |
| WO | 96/22976 | * 8/1996 | ......... C07D/209/34 |
| WO | WO 96/40116 A1 | 12/1996 | |
| WO | WO 98/16639 A1 | 4/1998 | |
| WO | WO 98/26054 A2 | 6/1998 | |
| WO | WO 98/35056 A1 | 8/1998 | |

OTHER PUBLICATIONS

Nasonova, VA et al, Ter Arkh, vol. 54(6), 1982, pp. 12–19, Russian document translated into English, Mixed Connective Tissue Disease.*
Yoneda, T et al, Cancer Research, vol. 51(16), pp. 4430–4435, 1991.*
Maguire, MP et al, J. Med. Chem. vol,. 37, pp. 2129–2137, 1994*
Current Drugs Ltd, ISSN 0962–2594, Current Opinion in Therapeutic Patents, Mar./Apr. 1993, Patent evaluation of EP–520722–A, pp. 425–427.*
Nasonova, VA et al, Ter Arkh, vol. 54(6), pp. 12–19, 1982, Mixed Connective tissue disease (abstract, English, only).*
Donovan, Frances M, Ph..D., Thrombin–induced protection and apoptossi in astrocytes and neurons:signal transduction pathways and regulation by protease nexin–1.vol. 58(08–B), Dissertation abstracts International, p. 4072, 1997, abstract only.*
Lopez–Talavera, J.C. et al, Journal of Clinical Investigation, vol. 100(3), pp. 664–670, Aug. 1997.*

(List continued on next page.)

*Primary Examiner*—Lynette R. F. Smith
*Assistant Examiner*—Ginny Allen Portner
(74) *Attorney, Agent, or Firm*—Beth A. Burrous; Foley & Lardner

(57) ABSTRACT

The present invention relates generally to the fields of immunology and medicine, and more specifically to the field of cellular signal transduction. The present invention relates, inter alia, to methods for diagnosis, treatment, and identification of therapeutics for particular inflammation-related diseases or disorders characterized by an interaction between a PYK2 polypeptide and a natural binding partner.

9 Claims, 16 Drawing Sheets

OTHER PUBLICATIONS

Levitzki, A, FASEB journal, vol. 6(14), pp. 3275–3282, Societies for Experimental Biology, Nov. 1992.*

Glaser, KB et al, Biochemical pharmacology, Feb. 9, 1993, vol. 45(3), pp. 711–721.*

Surwit, Richard S. et al, Arch. Dermatol., vol. 120(3), pp. 329–331. Double blind study of prazosin in the treatment of Raynaud's phenomenon in scleroderma.*

Aaronson "Growth Factors and Cancer," *Science*, 254:1146–1153 (1991).

Abe et al. "Molecular Characterization of a Novel Metabotropic Glutamate Receptor mGluR5 Coupled to Inositol Pohosphate/$Ca^{2+}$ Signal," *J. Biol. Chem.*, 267(19):13361–13368 (1992), © The American Society for Biochemistry and Molecular Biology, Inc., USA.

Adelman et al. "In Vitro Deletional Mutagenesis for Bacterial Production of the 20,000–Dalton Form of Human Pituitary Growth Hormone," *DNA*, 2(3):183–193 (1983), Mary Ann Liebert, Inc., Publishers.

Allen et al. "Modulation of CD4 by suramin" *Clin. Exp. Immunol.*, 91:141–146 (1991).

Anafi et al. "Tyrphostin–Induced Inhibition of p210bcr–abl Tyrosine Kinase Activity Induces K562 to Differentiate," *Blood*, 82(12):3524–3529, Dec. 15, 1993, © The American Society of Hematology, USA.

Andrade et al. "A G Protein Couples Serotonin and $GABA_B$ Receptors to the Same Channels in Hippocampus," *Science*, 234:1261–1265 (1986).

Anouti et al. "Tremor Disorders: Diagnosis and Management" *Western J. Medicine*, 162(6):510–513 Jun. 1995.

Aronheim et al. "Membrane Targeting of the Nucleotide Exchange Factor Sos is Sufficient for Activating the Ras Signaling Pathway," *Cell*, 78:949–961, Sep. 23, 1994, © Cell Press.

Botstein et al. "Making Mutations in vitro and Putting Them Back into Yeast," *Miami Winter Symposia—From Gene to Protein: Translation into Biotechnology*, eds. Ahmad et al., *Academic Press*, 19 265–274 (1982), © Academic Press.

Bowie et al. "Deciphering The Message in Protein Sequences: Tolerance to Amino Acid Substitutions," *Science*, 247:1306–1310, Mar. 16, 1990.

Brinster et al. "Factors Affecting the Efficiency of Introducing Foreign DNA into Mice by Microinjecting Eggs," *Proc. Natl. Acad. Sci. USA*, 82:4438–4442, Jul. 1985.

Broach "The Yeast Plasmid 2$\mu$ Circle," *Cell*, 28:203–204, Feb. 1982, © MIT.

Broach "The Yeast Plasmid 2$\mu$ Circle," in *The Molecular Biology of the Yeast Saccharomyces: Life Cycle and Inheritance*, Cold Spring Harbor Laboratory, Cold Spring Harbor, NY, 445–470 (1981).

Brown et al. "Ionic Channels and Their Regulation by G Protein Subunits," *Ann. Rev. Physiol.*, 52:197–213 (1990), © Annual Reviews Inc.

Brunton et al. "Anti–Tumour Activity of Novel Tryphostins in Breast Cancer Cells." *Proceedings of the Am. Assoc. for Cancer Res.*, 33:558 (#3335), Mar. 1992.

Bryckaert et al. "Inhibition of Platelet–Derived Growth Factor–Induced Mitogenesis and Tyrosine Kinase Activity in Cultured Bone Marrow Fibroblasts by Tyrphostins," *Exp. Cell Research*, 199:255–261 (1992), © Academic Press, Inc.

Bullock et al. (Eds.) *Techniques in Immunocytochemistry*, vols. 1, 2 and 3; Table Of Contents Only, © Academic Press, Inc.

Burgess et al. "Possible dissociation of the Heparin–Binding and Mitogenic Activities of Heparin–Binding (Acidic Fibroblast) Growth Factor–1 From Its Receptor–Binding Activities By Site–Directed Mutagenesis of A Single Lysine Residue," *J. Cell Biol.*, 11:2129–2138 (1990), © The Rockefeller University Press.

Burke et al. "Arylamides of Hydroxylated Isoquinolines As Protein–Tyrosine Kinase Inhibitors" *Bioorganic & Medicinal Chemistry Letters*, 2(12):1771–1774 (1992), © Pergamon Press Ltd., Great Britain.

Burke et al. Bicyclic Compounds as Ring–Constrained Inhibitors of Protein–Tyrosine Kinase p56$^{lck}$ *J. of Medicinal Chemistry*, 36(4):425–432, Feb. 19, 1983, © American Chemical Society.

Campbell "Monoclonal Antibody Technology, The Production and Characterization of Rodent and Human Hybridomas," *Laboratory Techniques in Biochemistry and Molecular Biology*, (Table Of Contents Only), vol. 13, © Elsevier Science Publishers, Amsterdam, The Netherlands, 1984.

Cantrell "G proteins in Lymphocyte Signalling," *Current Opinion in Immunology*, 6:380–384 (1994), © Current Biology Ltd.

Capecchi "Altering the Genome by Homologous Recombination," *Science*, 244:1288–1292, Jun. 16, 1989.

Carmeliet "Ion Channel Agonists: Expectations for Therapy." *Eur. Heart J.*, 12:30–37 (1991).

Cenatiempo "Prokaryotic Gene Expressin In Vitro: Transcription–Translation Coupled Systems," *Biochimie*, 68:505–515 (1986), © Societe de Chimie biologique/Elsevier, Paris.

Chater et al. "Streptomyces ØC31–Like Phages: Cloning Vectors, Genome Changes and Host Ranges," *Sixth International Symposium on Actinomycetes Biology*, eds. Szabe et al., Akademiai Kaido, Budapest, Hungary, 45–52 (1985).

Chen et al. "High–Efficiency Transformation of Mammalian Cells by Plasmid DNA," *Mol. and Cell. Biol.*, 7(8):2745–2752, Aug. 1987, © American Society for Microbiology.

Chen et al. "Shc Adaptor Proteins Are Key Transducers of Mitogenic Signaling Mediated By The G Protein–Coupled Thrombin Receptor," *EMBO Journal*, 15(5):1037–1044 (1996), © Oxford University Press.

Chomczynski et al. "Single–Step Method of RNA Isolation by Acid Guanidinium Thiocyanate–Phenol–Chloroform Extraction," *Analytical Biochemistry*, 162:156–159 (1987), © Academic Press.

Chowdhury et al. "Long–Term Improvement of Hypercholesterolemia After Ex Vivo Gene Therapy in LDLR–Deficient Rabbits," *Science*, 254:–1802–1805, Dec. 20, 1991.

Chu et al. "Electroporation for the efficient transfection of mammalian cells with DNA," *Nucleic Acids Res.* , 15(3):1311–1326 (1987), © IRL Press Limited, Oxford, England.

Cobb et al. "Stable Association of pp60$^{src}$ and pp59$^{fyn}$ with the Focal Adhesion–Associated Protein Tyrosine Kinase, pp125$^{FAK}$," *Mol. and Cell. Biol.*, 14(1):147–155, Jan. 1994, © American Society for Microbiology.

Colbère-Gararpin et al. "A New Dominant Hybrid Selective Marker for Higher Eukaryotic Cells," *J. Mol. Biol.*, 150:1–14 (1981), © Academic Press, Inc. (London) Ltd.

Cole et al. "The EBV–Hybridoma Technique and its Application to Human Lung Cancer," *Monoclonal Antibodies and Cancer Therapy*, 77–96 (1985), Eds. Reisfeld et al., © Alan R. Liss, Inc., New York.

Coleman et al. "Protein Against Dendrotoxin–Induced Clonic Seizures in Mice By Anticonvulsant Drugs," *Brain Res.*, 575:138–142 (1992), © Elsevier.

Cote et al. "Generation of Human Monoclonal Antibodies Reactive With Cellular Antigens," *Proc. Natl. Acad. Sci. USA* 80:2026–2030 (1983).

Creighton, T. *Proteins: Structures and Molecular Principles*, W.H. Freeman and Co., New York, 79–86 (1983).

Cristiano et al. "Hepatic Gene Therapy: Adenovirus Enhancement of Receptor–Mediated Gene Delivery and Expression in Primary Hepatocytes," *Proc. Natl. Acad. Sci. USA*, 90:2122–2126, Mar. 1993.

Cromakalim "Antihypertensive Potassium Channel Activator Antiallergic/Antiasthmatic," *Drugs of the Future*, 17(3):237–239, Mar. 1992.

Curiel et al. "Adenovirus Enhancement of Transferrin–Polylysine–Mediated Gene Delivery," *Proc. Nat. Acad. Sci. USA*, 88:8850–8854, Oct. 1991.

Curiel et al. "Gene Transfer to Respiratory Epithelial Cells via the Receptor–mediated Endocytosis Pathway," *Am. J. Respir. Cell. Mol. Biol.*, 6:247–252 (1992).

Curtin et al. "Inhibition of The Growth of Human Hepatocellular Carcinoma In Vitro And In Athymic Mice By A Quinazoline Inhibitor of Thymidylate Synthase, CB3717," *Br. J. Cancer*, 53:361–368 (1986), © The Macmillan Press Ltd.

Dasheiff "A New Method of Monitoring Membrane Potential In Rat Hippocampal Slices Using Cyanine Voltage–Sensitive Dyes," *J. of Neuroscience Methods*, 13:199–212 (1985), © Elsevier.

Daub et al. "Role of transactivation of the EGF receptor in signalling by G–protein–coupled receptors," *Nature* 379:557–560, Feb. 8, 1996.

Dikic et al. "A Role For PYK2 And Src In Linking G–Protein–Coupled Receptors With MAP Kinase Activation," *Nature*, 383: 547–560 (1996).

Dolle et al. "5,7–Dimethoxy–3–(4–pyridinyl)quinoline is a Potent and Selective Inhibitor of Human Vascular β–Type Platelet–Derived Growth Factor Receptor Tyrosine Kinase" *J. Med. Chem.*, 37(17):2627–2629 (1994).

Dolphin "G Protein Modulation of Calcium Currents in Neurons," *Ann. Rev. Physiol.*, 52:243–55 (1990), © Annual Reviews Inc.

Domchek et al. "Inhibition of SH2 Domain/Phosphoprotein Association by a Nonhydrolyzable Phosphonopeptide," *Biochemistry*, 31(41):9865–9870 (1992), © American Chemical Society.

Dong et al. "Activation of Tumoricidal Properties In Macrophages By Lipopolysaccharide Requires Protein–Tyrosine Kinase Activity" *Journal of Leukocyte Biology*, 53:53–60, Jan. 1993.

Dong et al. "Protein Tyrosine Kinase Inhibitors Decrease Induction of Nitric Oxide Synthase Activity in Lipopolysaccharide–Responsive and Lipopolysaccharide–Nonresponsibe Murine Macrophages" *J. Immunology*, 151(5):2717–2724, Sep. 1, 1993, © The American Association of Immunologists, USA.

Dreborg et al. "Ch. 10—The Chemistry and Standardization of Allergens," *Handbook of Experimental Immunology— vol. 1: Immunochemistry, 4th Ed.*, Eds. Weir et al., Blackwell Scientific Publications, Oxford, England, 10.1–10.28 (1986), Blackwell Scientific Publications.

Engvall et al. "Enzyme–Linked Immunosorbent Assay, ELISA. III. Quantitation of Specific Antibodies by Enzyme–Labeled Anti–Immunoglobulin in Antigen–Coated Tubes," *J. Immunology*, 109(1):129–135, Jul. 1972, © The Williams & Wilkins Co.

Ezoe et al. "PTK1, A Novel Protein Kinase Required For Proliferation of Human Melanocytes," *Oncogene*, 9:935–938 (1994), © Macmillan Press Ltd.

Fantl et al, "Distinct Phosphotyrosines on a Growth Factor Receptor Bind to Specific Molecules That Mediate Different Signaling Pathways," *Cell*, 69:413–423, May 1, 1992, © Cell Press.

Felder et al. "SH2 Domains Exhibit High–Affinity Binding to Tyrosine–Phosphorylated Peptides Yet Also Exhibit Rapid Dissociation and Exchange," *Mol. and Cell. Biol.*, 13(3):1449–1455 Mar. 1993, ©American Society for Microbiology.

Fry et al. "New Insights Into Protein–Tyrosine Kinase Receptor Signaling Complexes," *Protein Science*, 2:1785–1797 (1993), Cambridge University Press, USA, © The Protein Society.

Gazit et al., "Tyrphostins. 1. Synthesis and Biological Activity of Protein Tyrosine Kinase Inhibitors," *J. Med. Chem.*, 32(10):2344–2352 (1989).

Gazit et al. "Tyrphostins. 2. Heterocyclic and α–Substituted Benzylidenemalononitrile Tyrphostins as Potent Inhibitors of EGF Receptor and ErbB2/neu Tyrosine Kinases," *J. Med. Chem.*, 34(6):1896–1907 (1991).

Gazit et al. "Tyrphostins. 3. Structure–Activity Relationship Studies of a α–Substituted Benzylidenemalononitrile 5–S–Aryltyrphostins," *J. Med. Chem.*, 36(23):3556–3564 (1993).

Gehlert et al. "ATP Sensitive Potassium Channels: Potential Drug Targets in Neuropsychopharmacology," *Prog. Neuro–Psychopharmacol. Biol. Psychiatry*, 18:1093–1102 (1994).

Gillies et al. "Antigen Binding And Biological Activities of Engineered Mutant Chimeric Antibodies With Human Tumor Specificities," *Human Antibodies and Hybridomas*, 1: 47–54 (1990).

Gilman et al. "Isolation of Sigma–28–Specific Promoters From *Bacillus subtilis* DNA," *Gene*, 32:11–20 (1984), Elsevier.

Gilman "G Proteins: Transducers of Receptor–Generated Signals," *Ann. Rev. Biochem.*, 56:615–49 (1987), © Annual Reviews Inc.

Gishizky et al. "Mutant Forms of Growth Factor–Binding Protein–2 Reverse BCR–ABL–Induced Transformation," *Proc. Natl. Acad. SCi. USA*, 92:10889–10893 (1995).

Glick et al. "Factors Affecting The Expression of Foreign Proteins In *Escherichia coli*," *J. Industrial Microbiology*, 1:277–282 (1987), Elsevier.

Goding "Conjugation of Antibodies with Fluorochromes: Modifications to the Standard Methods," *J. Immunological Methods*, 13: 215–226 (1976), © Elsevier/North–Holland Biomedical Press.

Gold et al. "Translational Initiation in Prokaryotes," *Ann. Rev. Microbiol.*, 35:365–403 (1981), © Annual Reviews Inc.

Gottesman "Bacterial Regulation: Global Regulatory Networks," *Ann. Rev. Genet.*, 18:415–441 (1984).

Gryczan "Molecular Cloning in *Bacillus subtilis*," in *The Molecular Biology of the Bacilli*, edited by Dubnau, Academic Press, New York, Chp. 10:307–329 (1982).

Gumbiner "Proteins Associated with the Cytoplasmic Surface of Adhesion Molecules," *Neuron*, 11:551–564, Oct. 1993, © Cell Press.

Hamer et al. "Regulation In Vivo of a Cloned Mammalian Gene: Cadmium Induces the Transcription of a Mouse Metallothionein Gene in SV40 Vectors," *J. of Molecular and Applied Genetics*, 1:273–288 (1982), © Raven Press, New York.

Hammer et al. "Spontaneous Inflammatory Disease in Transgenic Rats Expressing HLA–B27 and Human $\beta_2$m: An Animal Model of HLA–B27–Associated Human Disorders," *Cell*, 63:1099–1112, Nov. 30, 1990, © Cell Press.

Herzog et al. "Molecular Cloning And Assignment Of FK2, A Novel Human Adhesion Mkinase To 8p11.2–P22 By Nonisotopic In Situ Hybridization," *Genomics*, 32:484–486 (1996), © Academic Press.

Hildebrand et al. "Identification of Sequences Required for the Efficient Localization of the Focal Adhesion Kinase, pp125$^{FAK}$, to Cellular Focal Adhesions," *J. Cell. Biology*, 123:993–1005 (1993).

Hille "G Protein–Coupled Mechanisms and Nervous Signaling," *Neuron*, 9:187–195 (1992), © Cell Press.

Houdebine et al. "Transgenesis in Fish," *Experientia*, 47:891–897 (1991), Switzerland.

Huang et al. "Tyrosine Kinase–Dependent Suppression of a Potassium Channel by the G Protein–Coupled m1 Muscarinic Acetylcholine Receptor," *Cell*, 75:1145–1156 (1993).

Hurby et al. "A User's Guide," *Synthetic Peptides*, Ed. Grant, Washington University School of Medicine, W.H. Freeman and Company, New York, 289–307 (1992).

Huse et al. "Generation of a Large Combinatorial Library of the Immunoglobulin Repertoire in Phage Lambda," *Science*, 246:1275–1281, Dec. 8, 1989.

Kaneda et al. "The Improved Efficient Method for Introducing Macromolecules into Cells Using HVJ (Sendai Virus) Liposomes with Gangliosides," *Experimental Cell Res.*, 173: 56–69 (1987), © Academic Press, Inc.

Kasprzak et al. "Location of a Contact Site Between Actin and Myosin in the Three–Dimensional Structure of the Acto–S1 Complex," *Biochemistry*, 28(23):9230–9238 (1989).

Kaur "Tyrphostin Induced Growth Inhibition: Correlation With Effect on p210$^{bcr-abl}$ Autokinase Activity In K562 Chronic Myelogenous Leukemia," *Anti–Cancer Drugs*, 5:213–222 (1994), © Rapid Communications of Oxford Ltd.

Kawashima et al. "Genomic Organiation Of The Human Homologue Of The Rat Pancreatic Elastase I Gene," *DNA Sequence—J. DNA Sequencing and Mapping*, 2:303–312 (1992), © Harwood Academic Publishers GmbH, United Kingdom.

Kendall et al. "Plasmid Transfer in *Streptomyces lividans*: Identification of a kil–kor System Associated with the Transfer Region of PIJ101," *J. of Bacteriology*, 169(9):4177–4183, Sep. 1987, © American Society for Microbiology.

Killen et al. "Specific Killing of Lymphocytes that Cause Experimental Autoimmune Myasthenia Gravis by Ricin Toxin–Acetlycholine Receptor Conjugates," *J. of Immunology*, 133(5):2549–2553, Nov. 1984, © The American Association of Immunologists, USA.

King et al. "Site–Specific Dephosphorylation and Deactivation of the Human Insulin Receptor Tyrosine Kinase By Particular And Soluble Phosphotyrosyl Protein Phosphatases," *Biochem. J.*, 275:413–418 (1991), Great Britain.

Köhler and Milstein "Continuous Cultures of Fused Cells Secreting Antibody of Predefined Specificity," *Nature*, 256:495–496, Aug. 7, 1975.

Kozbor et al. "The production of Monoclonal Antibodies from Human Lymphocytes," *Immun. Today*, 4(3):72–79 (1983), © Elsevier Biomedical Press.

Kubo et al. "Cloning, Sequencing and Expression of Complementary DNA Encoding The Muscarinic Acetylcholine Receptor," *Nature*, 323: 411–416 (1986).

Kuo et al. "Effects of Signalling Transduction Modulators on The Transformed Phenotypes in v–H–ras–Transformed NIH 3T3 Cells," *Cancer Letters*, 74:197–202 (1993), Elsevier Scientific Publishers, Ireland.

Lam et al. "A new type of synthetic peptide library for identifying ligand–binding activity," *Nature*, 354:82–84, Nov. 7, 1991.

Lazar et al. "Transforming Growth Factor $\alpha$: Mutation of Aspartic Acid 47 and Leucine 48 Results in Different Biological Activities," *Mol. And Cell. Biol.*, 8(3):1247–1252 (1988), © American Society for Microbiology.

Lee et al. "Active–Site–Directed Reductive Alkylation of Xanthine Oxidase by Imidazo[4,5–g]quinazoline–4,9–diones Functionalized with a Leaving Group," *Biochemistry*, 26(23):7355–7362 (1987), © American Chemical Society.

Lemus et al. "Studies of Extended Quinone Methides, Synthesis and Physical Studies of Purine–Like Monofunctional Imidazo[4,5–g]quinazoline Reductive Alkylating Agents," *J. Org. Chem.*, 54(15):3611–3618 (1989), © American Chemical Society.

Lev et al. "Protein Tyrosine Kinase PYK2 Involved in $Ca^{2+}$–Induced Regulation of ion Channel and MAP Kinase Functions," *Nature*, 376: 737–745, Aug. 31, 1995.

Lev et al. "Interspecies Molecular Chimeras of Kit Help Define the Binding Site of the Stem Cell Factor," *Molecular and Cellular Biology*, 13(4):2224–2234, Apr. 1993, © American Society for Microbiology.

Levitzki "Tyrphostins: Tyrosine Kinase Blockers As Novel Antiproliferative Agents and Dissectors of Signal Transduction," *FASEB J.*, 6:3275–3282, Nov. 1992.

Ley et al. "Synthesen Unter Verwendung von Benzofuroxan," *Synthesis*, 1975:415–422, Jul. 1975.

Liu et al. "Regulation of c–Src tyrosine Kinase Activity by the Src SH2 Domain," *Oncogene*, 8:1119–1126 (1993), © Macmillan Press Ltd.

Logan et al. "Adenovirus Tripartite Leader Sequence Enhances Translation of mRNAs Late After Infection," *Proc. Natl. Acad. Sci. USA*, 81:3655–3659, Jun. 1984.

Lowy et al. "Isolation of Transforming DNA: Cloning the Hamster aprt Gene," *Cell*, 22:817–823 Dec. 1980, © MIT.

Lutz et al. "The Distribution of Two hnRNP–Associated Proteins Defined by a Monoclonal Antibody Is Altered in Heat–Shocked HeLa Cells," *Experimental Cell Res.*, 175:109–124 (1988), © Academic Press, Inc.

Lyall et al. "Tyrphostins Inhibit Epidermal Growth Factor (EGF)–Receptor Tyrosine Kinase Activity in Living Cells and EGF–stimulated Cell Proliferation," *J. Bio. Chem.*, 264(24):14503–14509, Aug. 25, 1989, © American Society for Biochemistry and Molecular Biology, Inc., USA.

Maguire et al. "A New Series of PDGF Receptor Tyrosine Kinase Inhibitors: 3–Substituted Quinoline Derivatives," *J. Med. Chem.*, 37(14):2129–2137 (1994), © American Chemical Society.

Maniatis "Study of Eukaryotic Genes: Recombinant DNA Procedures," *Cell Biology: A Comprehensive Treatise, vol. 3, Gene Sequence Expression*, Academic Press, NY, Chp. 11: 563–608 (1980).

Manser et al. "A Non–Receptor Tyrosine Kinase That Inhibits the GTPase Activity of p21$^{cdc42}$," *Nature*, 363:364–367 (1993).

Marasco et al. "Design, Intracellular Expression, and Activity of a Human Anti–Human Immunodeficiency Virus Type 1 gp 120 Single–Chain Antibody," *Proc. Natl. Acad. Sci. USA*, 90:7889–7893, Aug. 1993.

Maxwell et al. "$^{19}$F Nuclear Magnetic Resonance Imaging of Drug Distribution in Vivo: The Disposition of an Antifolate Anticancer Drug in Mice," *Magnetic Resonance in Medicine*, 17:189–196 (1991), © Academic Press, Inc.

McKnight "Functional Relationships Between Transcriptional Control Signals of the Thymidine Kinase Gene of Herpes Simplex Virus," *Cell*, 31:355–365, Dec. 1982 (Part 1), © MIT.

McLean et al. "Oxcarbazepine: Mechanisms of Action," *Epilepsia*, 35(3):55–59 (1994), Raven Press, New York.

Millauer et al. "Glioblastoma Growth Inhibited in vivo By a Dominant–Negative Flk–1 Mutant," *Nature*, 367:576–579, Feb. 10, 1994.

Miller "Human Gene Therapy Comes of Age," *Nature*, 357:455–460, Jun. 11, 1992.

Miller et al. "Improved Retroviral Vectors for Gene Transfer and Expression," *Biotechniques*, 7(9):982–988 (1989).

Miller et al. "An Insect Baculovirus Host–Vector System for High–Level Expression of Foreign Genes," in *Genetic Engineering: Principles and Methods*, Eds. Setlow et al., Plenum Press, New York 8:277–298 (1986).

Mini et al. "Cytotoxic Effects of Folate Antagonists against Methotrexate–resistant Human Leukemic Lymphoblast CCRF–CEM Cell Lines," *Cancer Res.*, 45:325–330, Jan. 1985.

Miyachi et al. "Use of Copper(I) Trifluromethanesulfonate in β–Lactam Synthesis," *J. Org. Chem.*, 54(15):3511–3513, Jul. 21, 1989, © American Chemical Society.

Morrison et al. "Chimeric human antibodymolecules: Mouse antigen–binding domains with human constant region domains," *Proc. Natl. Acad. Sci. USA*, 81:6851–6855, Nov. 1984.

Mulligan "The Basic Science of Gene Therapy," *Science*, 260: 926–932, May 14, 1993.

Mulligan et al. "Selection For animal Cells That Express the *Escherichia coli* Gene Coding For Xanthine–Guanine Phosphoribosyltransferase," *PNAS*, 78(4):2072–2076, Apr. 1981.

Murphy et al. "Neuronal Selectivity of ATP–Sensitive Potassium Channels in Guinea–Pig Substantia Nigra Revealed By Responses To Anoxia," *J. of Physiology*, 453:167–183 (1992), Great Britain.

Murphy et al. "ATP–Sensitive Potassium Channels Counteract Anoxia in Neurons of the *Substantia niagra*," *Exp. Brain Res.*, 84:355–358 (1991), © Springer Verlag.

Nada et al. "Cloning of a Complementary DNA for a Protein–Tyrosine Kinase that Specifically Phosphorylates a Negative Regulatory Site of p60$^{c-src}$," *Nature*, 351:69–72, May 2, 1991.

Nelson "Detection of Acridinium Esters by Chemiluminescence," *Nonisotopic DNA Probe Techniques*, Ed. Larry J. Kricka, Academic Press, San Diego, Chapter 12, 275–310 (1992).

Neuberger et al. "Recombinant Antibodies Possession Novel Effector Functions," *Nature*, 312:604–608, Dec. 13, 1984.

O'Hare et al. "Transformation of mouse Fibroblasts to Methotrexate Resistance by a Recombinant Plasmid Expressing A Prokaryotic Dihydrfolate Reductase," *PNAS*, 78(3):1527–1531, Mar. 1981.

Okayama et al. "A cDNA Cloning Vector That Permits Expression of cDNA Inserts in Mammalian Cells," *Molecular and Cellular Biology*, 3(2):280–289, Feb. 1983, © American Society for Microbiology.

Olpe et al. "4–Aminopyridine and Barium Chloride Attenuate the Anti–Epileptic Effect of Carbamazepine in Hippocampal Slices," *Experientia*, 47:254–257 (1991), Birkhauser Verlag, Basel, Switzerland.

Peterson and Barnes "Genistein and Biochanin A Inhibit the Growth of Human Prostate Cancer Cells But Not Epidermal Growth Factor Receptor Tyrosine Autophosphorylation," *The Prostate*, 22: 335–345 (1993), © Wiley–Liss, Inc.

Phillips et al. "Quino[1,2–c]quinzalines.I.Synthesis of Quino[1,2–c]quinazolinium Derivatives and the Related Indazolo[2,3–a]quinoline Derivatives As Analogs of the Antitumor Benzo[c]phenanthridine Alkaloids," *J. Heterocyclic Chemistr*, 17:1489–1496, Nov. 1980, © HeteroCorporation.

Pillemer et al. "Insulin Dependence of Murine Lymphoid T–Cell Leukemia," *J. Cancer*, 50:80–85 (1992), © Wiley–Liss, Inc.

Popoli et al. "Cromakalim (BRL 34915) Counteracts the Epileptiform Activity Elicited By Ditiazem and Verapamil in Rats," *Br. J. Pharmacol*, 104:907–913 (1991), © Macmillan Press Ltd.

Porter et al. "New Antiepiletic Drugs: From Serendipity to Rational Discovery," *Epilepsia*, 33(1):S1–S6 (1992), Raven Press Ltd., New York.

Posner et al. "Kinetics of Inhibition by Tyrphostins of the Tyrosine Kinase Activity of the Epidermal Growth Factor Receptor and Analysis by a New Computer Program," *Molecular Pharmacology*, 45:673–683 (1993), © The American Society for Pharmacology and Experimental Therapeutics.

Pursel et al. "Genetic Engineering of Livestock," *Science*, 244:1281–1288, Jun. 16, 1989.

Reece et al. "Pharmacokinetics of Trimetrexate Administered by Five–Day Continuous Infusion to Patients with Advanced Cancer," *Cancer Res.*, 47:2996–2999, Jun. 1, 1987.

Rendu et al. "Inhibition of Platelet Activation by Tyrosine Kinase Inhibitors," *Biochem. Pharm.*, 44(5):881–888 (1992), © Pergamon Press Ltd., Great Britain.

Ricard–Mousnier et al. "Involvement of Voltage–Dependent Ion Channels in Epileptogenesis," *Neurophysiol Clin*, 23:395–421 (1993), © Elsevier, Paris.

Ridley et al. "The Small GTP–Binding Protein rho Regulates the Assembly of Focal Adhesions and Actin Stress Fibers in Response to Growth Factors," *Cell*, 70:389–399, Aug. 7, 1992, © Cell Press.

Rodriguez–Pena et al. "Rapid Dephosphorylation of a Mr 80000 Protein, a Specific Substrate of Protein Kinase C Upon removal of Phorbol Esters, Bomesin and Vasopressin," *Biochemical and Biophysical Comm.*, 140(1):379–385, Oct. 15, 1996.

Rotin et al. "SH2 Domains Prevent Tyrosin Dephosphorylation fo The EGF Receptor: Identification of Tyr992 as The High–Affinity Binding Site for SH2 Domains of Phospholipase Cγ" *EMBO J.*, 11(2):559–567 (1992), © Oxford University Press.

Rubin "Drosophila Melanogaster As An Experimental Organism," *Science*, 240:1453–1459, Jun. 10, 1988.

Ruther et al. "Easy Identification of cDNA Clones," *EMBO J.*, 2(10):1791–1794 (1983).

Sadoshima et al. "The heterotrimeric $G_q$ Protein–Coupled Angiotensin II Receptor Activates $p21^{ras}$ Via the Tyrosine Kinase–Shc–Grb2–Sos Pathway in Cardian Myocytes," *EMBO J.*, 15(4):775–787 (1996).

Santerre et al. "Expression of Prokaryotic Genes for Hygromycin B and G418 Resistance As Dominant–Selection Markers in Mouse L Cells," *Gene*, 30:147–156 (1984), Elsevier.

Sasaki et al. "Cloning of a cDNA for the Human Adhesion Kinase Beta," *Tumor Res.*, 30:37–46 (1995).

Sauro et al. "Decreased Sensitivity of Aorta from Hypertensive Rats to Vasorelazation by Tyrphostin," *Life Sciences*, 53(22):371–376 (1993), Pergamon Press, USA.

Sauro et al. "Tyrphostin Attenates Platelet–Derived Growth Factor–Induced Contraction in Aortic Smooth Muscle Through Inhibition of Protein Tyrosine Kinase(s)," *J. of Pharmacolory and Experimental Therapeutics*, 267(3):1119–1125 (1993), © The American Society for Pharmacology and Experimental Therapeutics, USA.

Schaller et al. "Focal Adhesion Kinase: an Integrin–Linked Protein Tyrosine Kinase,".

Schaller et al. "Autonomous Expression of a Noncatalytic Domain of the Focal Adhesion–Associated Protein Tyrosine Kinase $pp125^{FAK}$," *Mol. and Cell. Biol.*, 13(2):785–791, Feb. 1993, © American Society for Microbiology.

Schaller et al. "$pp125^{FAK}$, a Structurally Distinctive Protein–Tyrosine Kinase Associated with Focal Adhesions," *Proc. Natl. Acad. Sci. USA*, 89:5192–5196, Jun. 1992.

Schlessinger "Signal Transduction by Allosteric Receptor Oligomerization," *Trends in Biochemical Sciences*, 13:443–447, Nov. 1988, The International Union of Biochemistry and Elsevier Publications Cambridge.

Schrey et al. "Bombesin and Glucocorticoids Stimulate Human Breast Cancer Cells to Produce Endohelin, a Paracrine Mitogen for Breast Stromal Cells," *Cancer Res.*, 52:1786–1790, Apr. 1, 1992.

Sculier et al. "Role of an Intensive Care Unit (ICU) In a Medical Oncology Department," *Cancer Immunol. and Immunotherapy*, 23:A65 (1986).

Shattil et al. "Tyrosine Phosphorylation of $pp125^{FAK}$ in Platelets Requires Coordinated Signalling Through Integrin and Agonist Receptors," *J. Biol. Chem.*, 269(2):14738–14745, May 20, 1994, © The American Society for Biochemistry and Molecular Biology, Inc., USA.

Sikora et al. "Development of an Assay for the Estimation of $N^{10}$–Propargyl–5,8–dideazafolic Acid Polyglutamates in Tumor Cells," *Analytical Biochemistry*, 172:344–355 (1988), © Academic Press.

Sikora et al. "Quinazoline CB 3717 and CB 3703 Inhibitors of Folate Retention and Metabolsim in Ehrlich Ascites Carcinoma Cells and Some Organs of the Host–Mouse," *Cancer Letters*, 23:289–295 (1984), Elsevier Scientific Publishers Ireland Ltd.

Silver et al. "Amino Terminus of the Yeast GAL4 Gene Product is Sufficient for Nuclear Localization," *Proc. Natl. Acad. Sci. USA*, 81:5951–5955, Oct. 1984.

Simon et al. "Potassium Channel Openers Block Seizure Activity In an In–Vitro Model of Epilepsy," *Biophys. J.*, 64:A100 (1993).

Simons et al. "Gene Transfer into Sheep," *Bio/Technology*, 6:179–182, Feb. 1988.

Skolnik et al. "Cloning of P13 Kinase–Associated p85 Utilizing a Novel Method for Expression/Cloning of Target Proteins for Receptor Tyrosin Kinases," *Cell*, 65:83–90, Apr. 5, 1991, © Cell Press.

Smith et al. "Single–Step Purification of Polypeptides Expressed in *Escherichia coli* as Fusions with Glutathione S–Transferase," *Gene*, 67:31–40 (1988).

Smith et al. "Molecular Engineering of the *Autographa californica* Nuclear Polyhedrosis Virus Genome: Deletion Mutations Within the Polyhedrin Gene," *J. Virology*, 46(2):584–593, May 1983, © May 1983.

Songyang et al. "SH2 Domains Recognize Specific Phosphopeptide Sequences," *Cell*, 72:767–778, Mar. 12, 1993, © Cell Press.

St. Groth et al. "Production of Monoclonal Antibodies: Strategy and Tactics," *J. Immunol. Methods*, 35:1–21 (1980), ©Elsevier/North–Holland Biomedical Press.

Sternberger et al. "The Unlabeled Antibody Enzyme Method of Immunohistochemistry: Preparation and Properties of Soluble Antigen–Antibody Complex (Horseradish Peroxidase–Antihorseradish Peroxidase) and its Use in Indentification of Spirochetes," *J. Histochemistry and Cytochemistry*, 18(5):315–333 (1970), © The Histochemical Society, Inc., USA.

Su "Delineating Biochemical and Functional Properties of Sigma Receptors: Emerging Concepts," *Critical Reviews in Neurobiology*, 7(3,4):187–203 (1993), © CRC Press, Inc.

Szybalska et al. "Genetics of Human Cell Lines, IV. DNA–Mediated Heritable Transformation of a Biochemical Trait," *PNAS*, 48:2026–2034 (1962).

Takeda et al. "Construction of Chimaeric Processed Immunoglobulin Genes Containing mouse Variable and Human Constant Region Sequences," *Nature*, 314:452–454, Apr. 4, 1985.

Tao et al. "Role of Carbohydrate in the Structure and Effector Functions Mediated by the Human IgG constant Region" *J. Immunol.*, 143(8):2595–2601, Oct. 15, 1989, © The American Association of Immunologists, USA.

Tijssen "Practice and Theory of Enzyme Immunoassays: Laboratory Techniques in Biochemistry and Molecular Biology," vol. 15, Elsevier Science Publishers, Amsterdam, The Netherlands, (Table Of Contents Only) (1985).

Tokiwa et al. "Activation of Pyk2 by Stress Signals and Coupling with JNK Signaling Pathway," *Science*, 273:792–794, Aug. 9, 1996.

Treherne et al. "The Regional Distribution of Sulphonylurea Binding Sites in Rat Brain," *Neuroscience*, 40(2):523–531 (1991, © Pergamon Press plc, Great Britain.

Ullrich et al. "Signal Transduction by Receptors with Tyrosine Kinase Activity," *Cell*, 61:203–212, Apr. 1990, ©Cell Press.

Ulmanen et al. "Transcription and Translation of Foreign Genes in *Bacillus subtilis* by the Aid of a Secretion Vector," *J. Bacteriology* 162(1):176–182, Apr. 1985, ©American Society for Mirobiology.

van Biesen et al. "Receptor–Tyrosine–Kinase– and Gβγ–Mediated MAP Kinase Activation by a Common Signaling Pathway," *Nature*, 376:781–784, Aug. 31, 1995.

Van Heeke et al. "Expression of Human Asparagine Synthetase in *Escherichia coli*," *J. Biol. Chem.*, 264(10):5503–5509, Apr. 5, 1989, © The American Society for Biochemistry and Molecular Biology, Inc., USA.

Wan et al. "Tyrosine Kinases in Activation of the MAP Kinase Cascade by G–Protein–Coupled Receptors," *Nature*, 380:541–544, Apr. 11, 1996.

Ward et al. "Binding Activities of a Repertoire of Single Immunoglobulin Variable Domains Secreted from *Escherichia coli*," *Nature*, 341:544–546, Oct. 12, 1989.

Ward et al. "Construction and Characterisation of a Series of Multi–Copy Promoter–Probe Plasmid Vectors for Streptomyces Using the Aminoglycoside Phosphotransferase Gene from Tn5 as Indicator," *Mol. Gen. Genet.*, 203:468–478 (1986), © Springer–Verlag.

Whitney "Human T and B Lympholytes Express a Structurally Conserved Focal Adhesion Kinase pp125$^{FAK}$," *DNA Cell Biol.*, 12(9):823–830 (1993), Mary Ann Liebert, Inc., Publishers.

Wigler et al. "Transfer of Purified Herpes Virus Thymidine Kinase Gene to Cultured Mouse Cells," *Cell*, 11:223–232, May 1977, © MIT.

Wigler et al. "Transformation of Mammalian Cells with an Emplifiable Dominant–Acting Gene," *Proc. Natl. Acad. Sci. USA*, 77(6):3567–3570, Jun. 1980.

Wigler et al. "Transformation of Mammalian Cells with Genes from Procaryotes and Eucaryotes," *Cell*, 16:777–785, Apr. 1979, © MIT.

Wilchek et al. "The Literature on Affinity Chromatography," *Methods in Enzymology*, 34:3–10 (1974).

Wilk–Blaszczak et al. "Bradykinin Modulates Potassium and Calcium Currents in Neuroblastoma Hybrid Cells via Different Pertussis Toxin–Insensitive Pathways," *Neuron*, 12:109–116, Jan. 1994, © Cell Press.

Wilson et al. "Clinical Protocol: Ex Vivo Gene Therapy of Familial Hypercholesterolemia," *Human Gene Therapy*, 3:179–222 (1991), Mary Ann Liebert, Inc., Publishers.

Wilson et al. "Distribution and Molecular Characterization of a Cell–Surface and a Cytoplasmic Antigen Detectable in Human Melanoma Cells with Monoclonal Antibodies," *Int. J. Cancer*, 28:293–300 (1981).

Wolbring et al. "Inhibition GTP–Utilizing Enzymes by Tyrphostins," *J. Biol. Chem.*, 269(36):22470–22472 (1994), © The American Society for Biochemistry and Molecular Biology, Inc., USA.

Wolff et al. "Direct Gene Transfer into Mouse Muscle In Vivo," *Science*, 247: 1465–1468 (1990).

Wu et al. "Receptor–Mediated In Vitro Gene Transformation by a Soluble DNA Carrier System," *J. Biol. Chem.*, 262(10):4429–4432, Apr. 5, 1987, © The American Society of Biological Chemists, Inc., USA.

Wu et al. "Receptor–Mediated Gene Delivery In Vivo, Partial Correction of Genetic Analbuminemia in Nagas-Rats," *J. Biol. Chem.*, 266:14338–14342, Aug. 5, 1991, © The American Society for Biochemistry and Molecular Biology, Inc., USA.

Xie et al. "Dominant–Negative Mutants of Grb2 Induced Reversal of the Transformed Phenotypes Caused by The Point Mutation–Activated Rat HER–2/Neu," *J. Biol. Chem.*, 270(51):30717–30724, Dec. 22, 1995, © The American Society for Biochemistry and Molecular Biology, Inc., USA.

Yang et al. "Human Very Low Density Lipoprotein Structure: Interaction of the c Apolipoproteins With Apolipoprotein B–100," *J. Lipid Research*, 34(8):1311–1321, Aug. 1993.

Yang et al. "In Vivo and In Vitro Gene Transfer to Mammalian Somatic Cells by Particle Bombardment," *Proc. Natl. Acad. Sci. USA*, 87:9568–9572, Dec. 1990.

Yoneda et al. "The Antiproliferative Effects of Tyrosine Kinase Inhibitors Tyrphostins on a Human Squamous Cell Carcinoma in Vitro and in Nude Mice," *Cancer Research*, 5:4430–4435, Aug. 15, 1991.

Yu et al. "Activation of a Novel Calcium Dependent Protein Tyrosine Kinase," *J. Biol. Chem.*, 271(47):29993–29998, Nov. 22, 1996, © The American Society for Biochemistry and Molecular Biology, Inc, USA.

Zheng et al. "Interaction of cellular proteins with a novel tyrosine kinase PY2," *Mol. Biol. of the Cell*, 7:360A (1996).

Zhu et al. "Systemic Gene Expression After Intravenous DNA Delivery into Adult Mice," *Science*, 261:209–211, Jul. 9, 1993.

Avraham et al. "Identification and Characterization of a Novel Related Adhesion Focal Tyrosine Kinase (RAFTK) from Megakaryocytes and Brain," *J. Biol. Chem.*, 270:27742–27751 (1995).

Baker et al. "Induction of Acetycholine Receptor Clustering By Native Polystyrene Beads: Implication of an Endogenous Muscle–Derived Signaling System," *J. Cell Science*, 102:543–555 (1992), © The Company of Biologists Limited, Great Britain.

Barker et al. "In Vitro Activity of Non–Glutamate Containing Quinazoline–Based Thymidylate Synthase Inhibitors" *Proc. Am. Assoc. Cancer Res.*, 32:327 No. 1939, Mar. 1991.

Baudy "Agents for the Treatment of Neurodegenerative Diseases: Part 2," *Exp. Opin. Ther. Patents*, 4(4):343–378, (1994), © Ashley Publications ISSN 0962–2594.

Bayer et al. "The Avidin–Biotin Complex in Affinity Cytochemistry," *Methods in Enzymology*, 62: 308–319 (1979), © Adademic Press, Inc.

Benoist et al. "In Vivo Sequence Requirements of the SV40 Early Promoter Region," *Nature*, 290:304–310, Mar. 26, 1981.

Bertino "Toward Improved Selectivity in Cancer Chemotherapy: The Richard and Hinda Rosenthal Founation Award Lecture" *Cancer Res.*, 39:293–304, Feb. 1979.

Bilder et al. "Tyrphostins inhibit PDGF–induced DNA Synthesis and Associated Early Events in Smooth Muscle Cells," *Am. J. Physiol.*, 260:C721–C730 (1991), © American Physiological Society.

Bird et al. "Single–Chain Antigen–Binding Proteins," *Science*, 242: 423–426, Oct. 21, 1988.

Birnstiel et al. "Adenosine–Mediated Synaptic Inhibition: Partial Blockade by Barium Does Not Prevent Anti–Epileptiform Activity," *Synapse*, 11:191–196 (1992), © Wiley–Liss, Inc.

Bitter et al. "Expression and Secretion Vectors for Yeast," *Methods in Enzym.* 153:516–544 (1987), © Academic Press, Inc.

Bollon et al. "DNA Transformation Efficiency of Various Bacterial and Yeast Host–Vector Systems," *J. Clini. Hematology and Oncology*, 10(2, 3):39–48, Apr. –Jul. 1980.

Bork "Powers and Pitfalls in Sequence Analysis: The 70% Hurdle", *Genome Res.*, 10:398–400 (2000), © Cold Spring Harbor Laboratory.

Felgner et al. "Cationic Liposome–Mediated Transfection," *Nature*, 337:387–388, Jan. 26, 1989.

Felgner et al. "Lipofection: A Highly Efficient, Lipid–mediated DNA–transfection Procedure," *Proc. Natl. Acad. SCi. USA*, 84:7413–7417, Nov. 1987.

Felsch et al. "Activation of Protein Tyrosine Kinase PYK2 By The M1 Muscarinic Acetylecholine Receptor" *PNAS*, 95:5051–5056, Apr. 1998.

Fernandes et al. "Biochemical and Antitumor Effects of 5,8–Dideazaisopteroylglutamate, a Unique Quinazoline Inhibitor of Thymidylate Synthase" *Cancer Res.*, 43:1117–1123, Mar. 1983.

Ferrari et al. "An in Vivo Moel of Somatic Cell Gene Therapy for Human Severl Combined Immunodeficiency," *Science*, 251:1363–1366, Mar. 15, 1991.

Ferris et al. "Synthesis of Zuinazoline Nucleosides from Ribose and Anthranilonitrile. Application of Phase–Transfer Catalysis in Nucleoside Synthesis," *J. Org. Chem.*, 44(2):173–178 (1979), © American Chemical Society.

Fingl et al. "Section I, Introduction , Chapter 1, General Principles," *The Pharmacological Basis of Therapeutics, 5th Ed.*), Eds. Goodman et al., MacMillan Publishing Co., Inc., New York, pp. 1–46 (1975).

Fischer and Schonbrunn "Bombesin Receptor is Coupled to a Guanine Nucleotide–binding Protein Which is Insensitive to Pertussis and Cholera Toxins," *J. Biol. Chem.*, 263(6):2808–2816, Feb. 25, 1988, © Society for Biochemistry and Molecular Biology, Inc., USA.

Fischer et al. "Protein Tyrosine Phosphatases: A Diverse Family of Intracellular and Transmembrane Enzymes," *Science*, 253:401–406, Jul. 26, 1991.

Fischer et al. "Frontiers of Clinical Neuroscience, vol. 11: Neurotransmitters and Epilespsy," Wiley–Liss, New York (Table Of Contents Only).

Frucht et al. "Characterization of Functional Receptors for Gastrointestinal Hormones on Human Colon Cancer Cells," *Cancer Research*, 52:1114–1122, Mar. 1, 1992.

Fry et al. "A Specific Inhibitor of the Epidermal Growth Factor Receptor Tyrosine Kinase," *Science*, 265:1093–1095, Aug. 19, 1994.

Huston et al. "Protein Engineering of Antibody Binding Sites: Recovery of Specific Activity In An Anti–Digoxin Singel–Chain Fv Analogue Produced in *Escherichia coli*," *Proc. Natl. Acad. Sci. USA*, 85:5879–5883, Aug. 1988.

Inouye et al. "Up–Promoter Mutations In The IPP Gene of *Escherichia coli*," *Nucleic Acids Research*, 13(9):3100–3111 (1985), © IRL Press Limited, Oxford, England.

Iverson and Rudy "The Role of the Divergent Amino and Carboxyl Domains on the Inactivation Properties of Potassium Channels Derived from the Shaker Gene of Drosophila," *J. Neuroscience*, 10(9):2903–2916 (1990).

Izaki "Plasmid Induced Heavy Metal Resistance," *Japanese J. of Bacteriology*, 33(6):729–742 (1978).

Jackman "ICI D1694, a Quinazoline Antifolate Thymidylate Synthase Inhibitor That Is a Potent Inhibitor of L1210 Tumor Cell Growth in Vitro and in Vivo: A New Agent for Clinical Study," *Cancer Res.*, 51:5579–5586, Oct. 15, 1991.

Jansen et al. "Immunotoxins: Hybrid Molecules Combining High Specificity and Potent Cytotoxicity," *Immunological Rev.*, 62:185–216 (1982), Munksgaard, Copenhagen, Denmark.

John et al. "Plasmids as Epidemiologic Markers in Nosocomial Gram–Negative Bacilli: Experience at a University and Review of the Literature," *Reviews of Infectious Diseases*, 8(5):693–704, Sep.–Oct. 1986, © The University of Chicago.

Johnson *Proc. Natl. Acad. Sci. US*, 90: 5677–5681 (1993).

Johnson et al. "Isolation of The Yeast Regulatory Gene GAL4 And Analysis of Its Dosage Effects on The Galactose/Melibiose Regulon," *Proc. Natl. Acad. Sci. US*, 79: 6971–6975 (1982).

Jones et al. "Quinazoline Antifolates Inhibiting Thymidylate Synthase: Varation of the Amino Acid," *J. Med. Chem.*, 29:1114–1118 (1986), © American Chemical Society.

Joyner et al. "Production of A Mutation In Mouse En–2 By Homologous Recombination In Embryonic Stem Cells," *Nature*, 338:153–156, Mar. 9, 1989.

Kaneda et al. "Increased Expression of DNA Cointroduced with Nuclear Protein in Adult Rat Liver," *Science*, 243:375–378, Jan. 20, 1989.

* cited by examiner

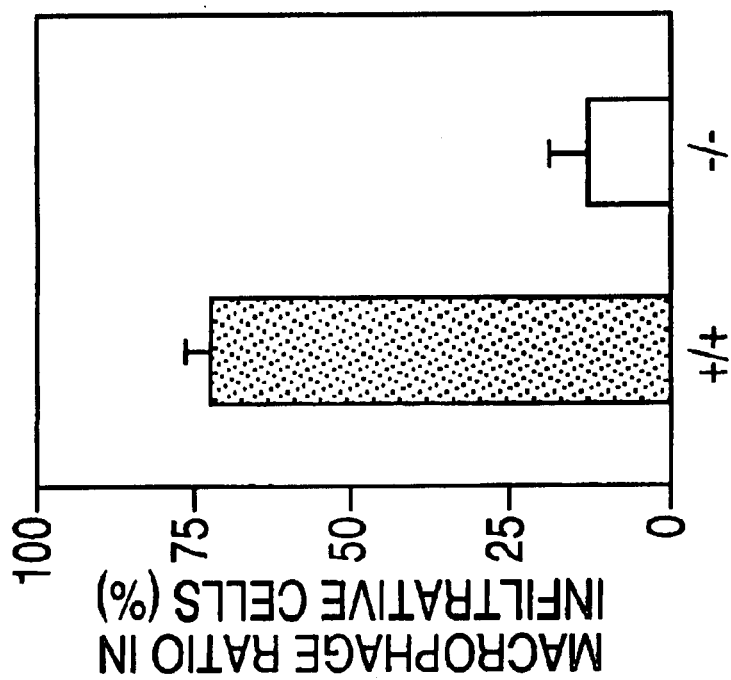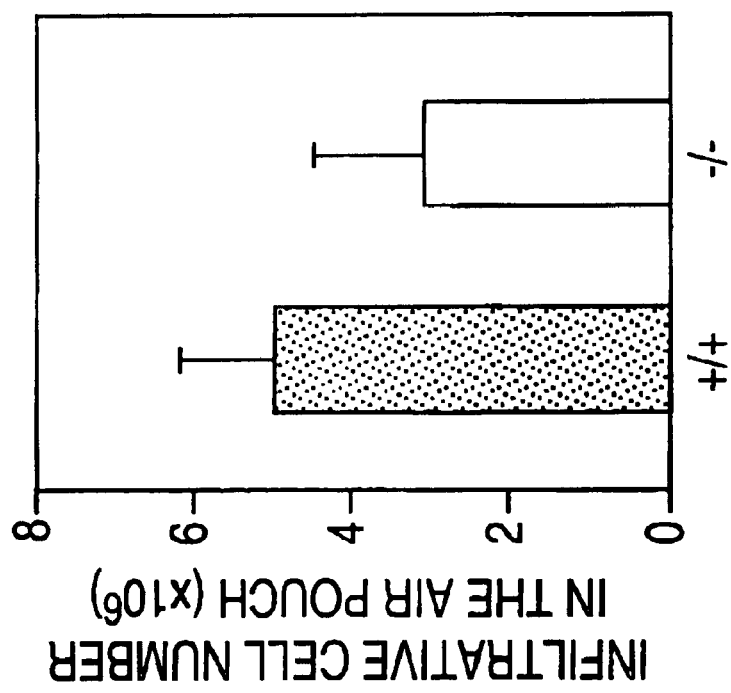

FIG. 6a Phosphorylation of Pyk2 in P388D1 Cells after LPS Stimulation
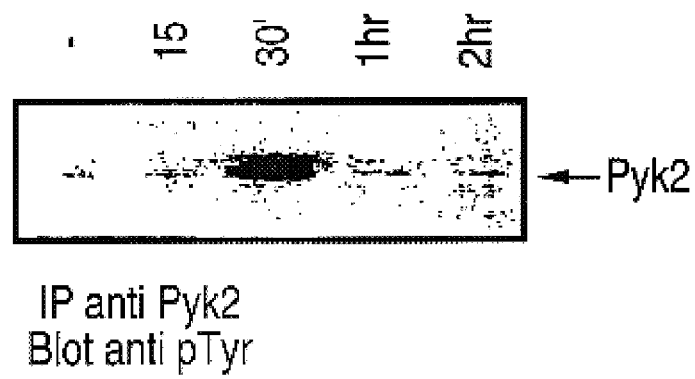
IP anti Pyk2
Blot anti pTyr
FIG. 6b
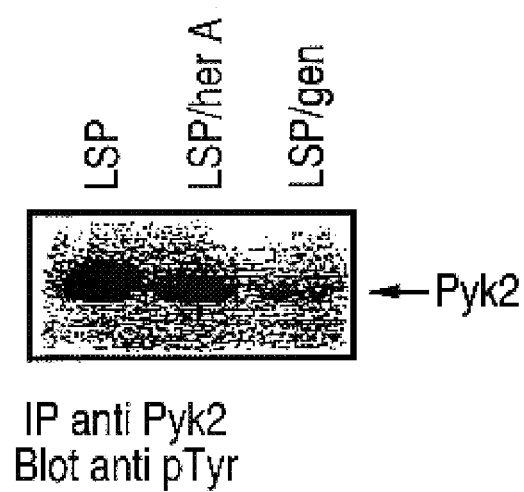
IP anti Pyk2
Blot anti pTyr

FIG. 7a Expression of Pyk2 w.t.-HA and Pyk2-ATP-HA in P388D.1 cells is inducible via Doxycyclin Utilizing the Tet-On Gene Expression System FIG. 7b
Pyk2-ATP-HA With Doxycyclin
Clone # 3  4  5  6  7  8  1
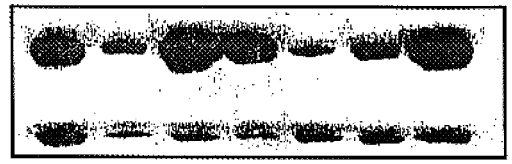
Pyk2 w.t.-HA With Doxycyclin
25  31
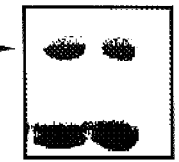
← Pyk2 →
FIG. 7c Pyk2-ATP-HA Without Doxycyclin
FIG. 7d Pyk2 w.t.-HA Without Doxycyclin
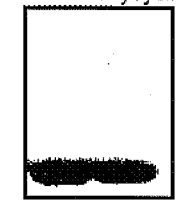
Blot anti-HA Expression of Pyk2 Kinase Mutant Suppresses
TNF Secretion in P388D1 Cells

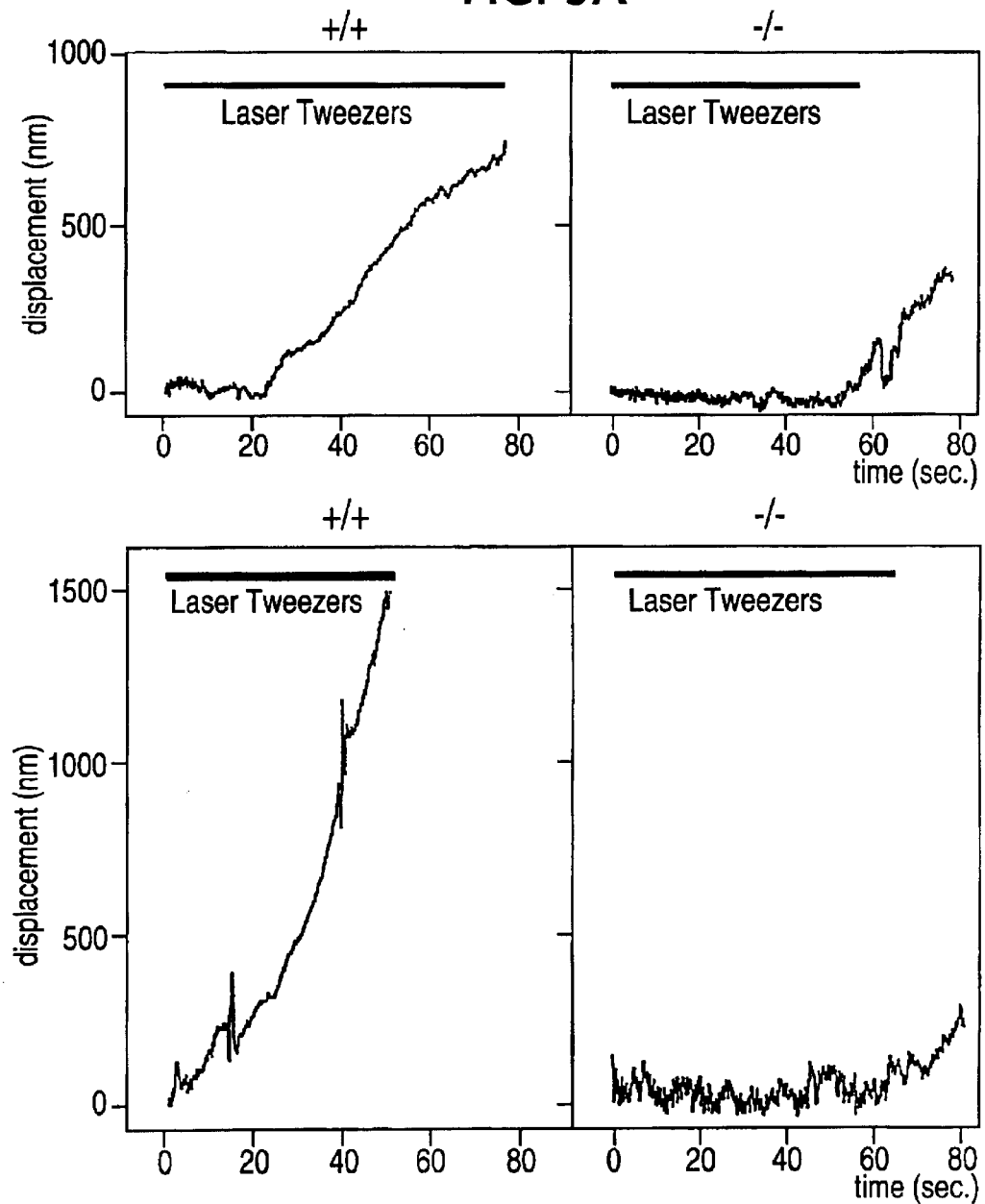

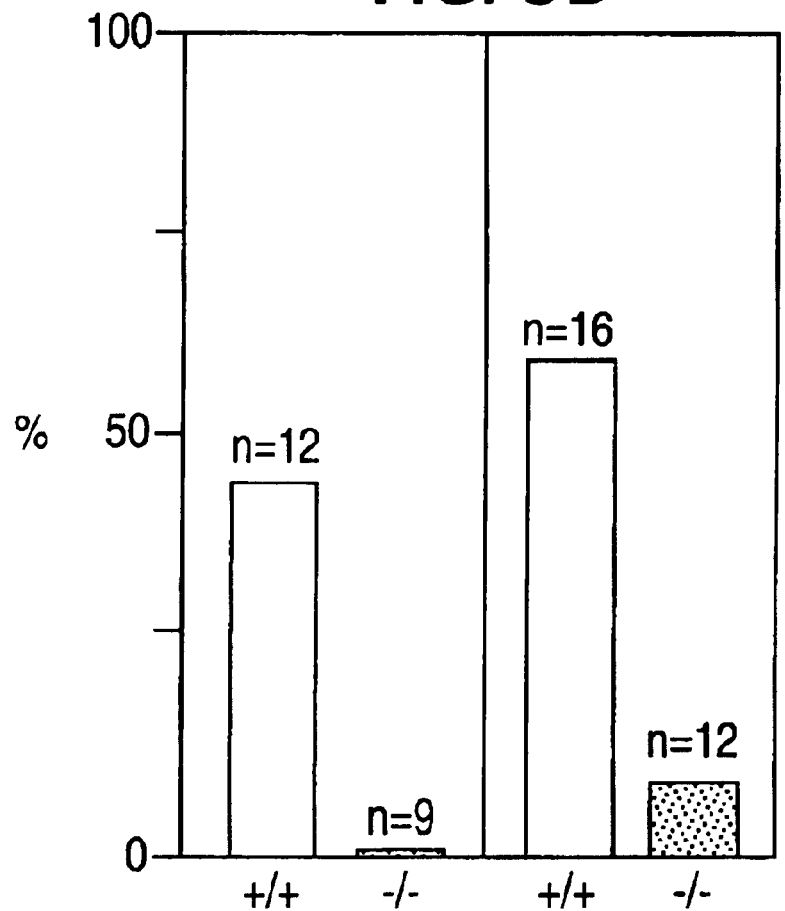

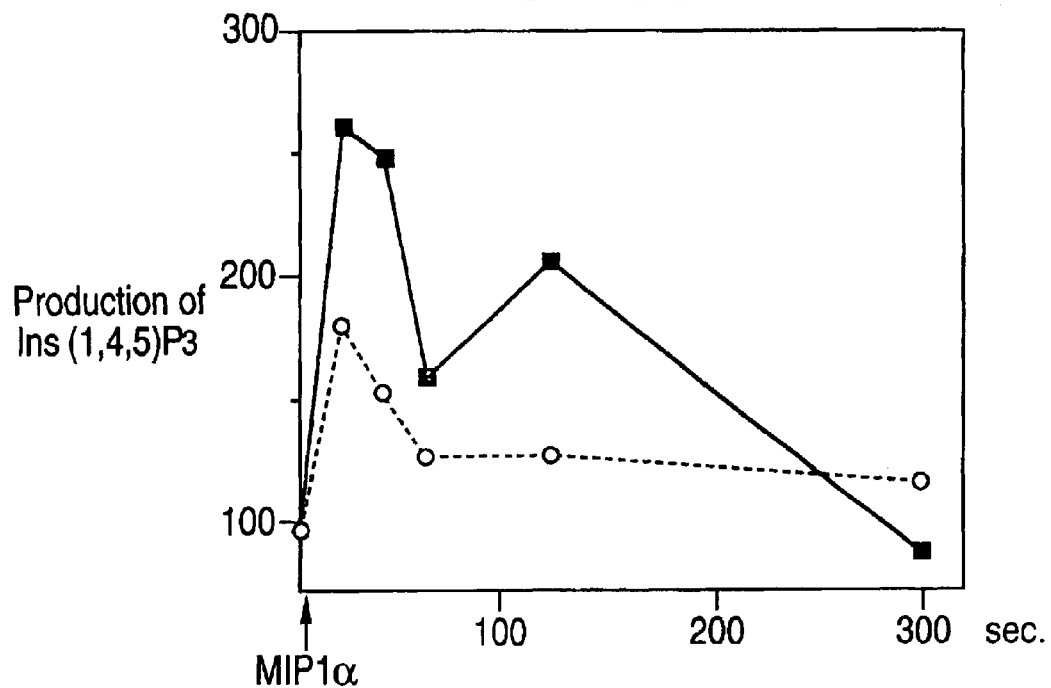

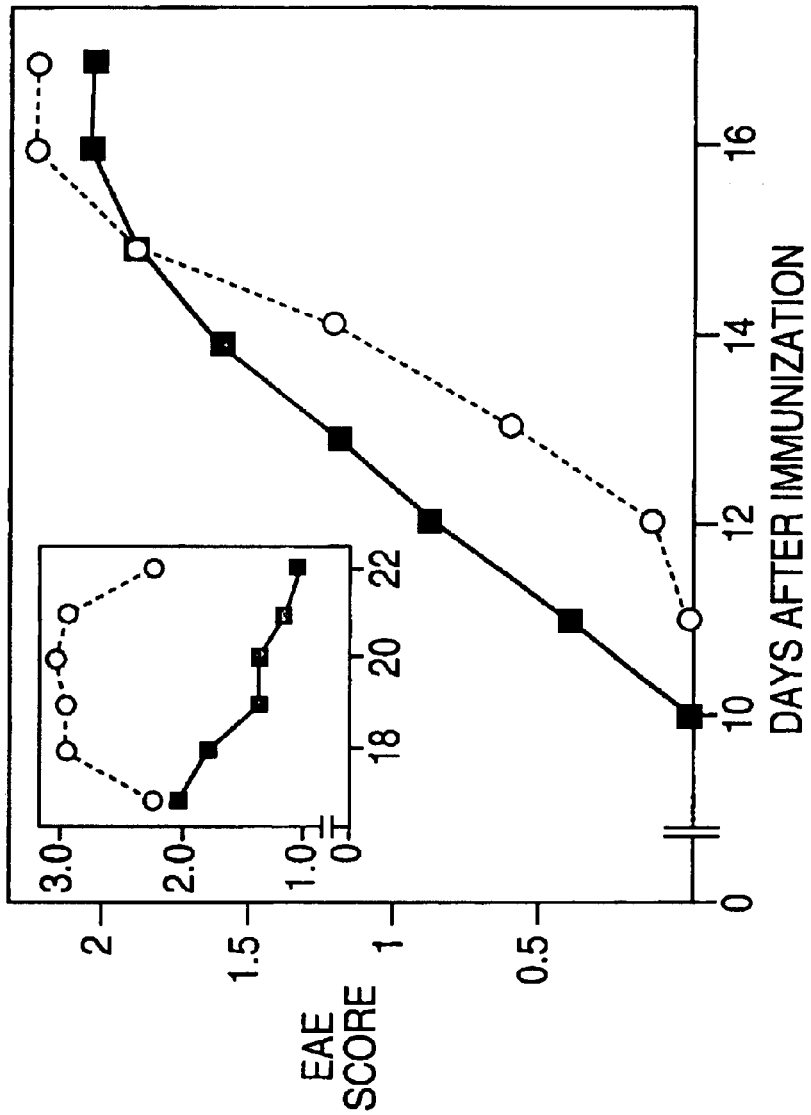

PYK2 AND INFLAMMATION

RELATED APPLICATIONS

The present application claims priority to U.S. Provisional Patent Application Ser. No. 60/114,465 by Schlessinger, Okigaki, and Gishizky, entitled PYK2 and Inflammation, filed Dec. 30, 1998 (Lyon & Lyon Docket No. 236/075) which is hereby incorporated by reference herein in its entirety, including any drawings, tables, or figures.

FIELD OF THE INVENTION

The present invention relates generally to the fields of immunology and medicine, and more specifically to the field of cellular signal transduction.

BACKGROUND OF THE INVENTION

None of the following discussion of the background of the invention, which is provided solely to aid the reader in understanding the invention, is admitted to be or to describe prior art to the invention.

Cellular signal transduction is a fundamental mechanism whereby external stimuli that regulate diverse cellular processes are relayed to the interior of cells. One of the key biochemical mechanisms of signal transduction involves the reversible phosphorylation of tyrosine residues on proteins. The phosphorylation state of a protein is modified through the reciprocal actions of tyrosine phosphatases (TPs) and tyrosine kinases (TKs), including receptor tyrosine kinases and non-receptor tyrosine kinases.

RTKs are composed of at least three domains: an extracellular ligand binding domain, a transmembrane domain and a cytoplasmic catalytic domain that can phosphorylate tyrosine residues. The intracellular, cytoplasmic, non-receptor protein tyrosine kinases do not contain a hydrophobic transmembrane domain or an extracellular domain and instead contain non-catalytic domains in addition to their catalytic kinase domains. Such non-catalytic domains include the SH2 domains and SH3 domains. The non-catalytic domains are thought to be important in the regulation of protein-protein interactions during signal transduction.

FAK (focal adhesion kinase) and PYK2 (proline-rich tyrosine kinase also known as RAFTK, CAK and CADTK (Lev, et al. (1995) Nature 376:737–745; Avraham, et al. (1995) J. Biol. Chem. 270:27742–27751; Sasaki, et al. (1995) J. Biol. Chem. 270:21206–21219; Yu, et al. (1996) J. Biol. Chem. 271:29993–29998) comprise one family of protein tyrosine kinases. FAK and PYK2 exhibit approximately 45% amino acid sequence identity to each other and each contain an N terminus with similarity to band 4.1 homology domain, a centrally located protein tyrosine kinase domain (Girault, et al. (1999) Trends Neurosci. 22:257–263), and two proline rich regions at the C-terminus (Lev, et al. (1995) Nature 376:737–745). PYK2 and FAK bind to proteins that have been shown to interact with the cytoskeleton such as paxillin (Salgia, et al. (1996) J. Biol. Chem. 271:31222–31226), p130$^{cas}$, the rhoGAP protein Graf (Ohba, et al. (1998) Biochem. J. 330:1249–1254) and a novel protein containing a LIM domain (Matsuya, et al. (1998) J. Biol. Chem. 273:1003–1014; Lipsky, et al. (1998) J. Biol. Chem. 273:11709–11713).

PYK-2 is a non-receptor tyrosine kinase that is activated by binding of ligand to G-coupled protein receptors such as bradykinin and acetylcholine. PYK2 has a predicted molecular weight of 111 kD and contains five domains: (1) a relatively long N-terminal domain; (2) a kinase catalytic domain; (3) a proline rich domain; (4) another proline rich domain; and (5) a C-terminal domain.

PYK2 is expressed in various tissues, including neural tissues, hematopoietic cells, and in some tumor cell lines. PYK2 is believed to regulate the activity of potassium channels in response to neurotransmitter signaling. PYK2 may also regulate ion-channel function by tyrosine phosphorylation.

PYK2 is activated by stimulation of G-protein coupled receptors (Lev, et al. (1995) Nature 376:737–745), by stimulation of antigen receptors on T cells (Qian, et al. (1997) J. Exp. Med. 185:1253–1259); B cells (Astier, et al. (1997) J. Biol. Chem. 272:228–232), and mast cells (Okazaki, et al. (1997) J. Biol. Chem. 272:32443–32447); as well as in response to inflammatory cytokines (Tokiwa, et al. (1996) Science 273:792–794; Miyazaki, et al. (1998) Genes Dev. 12:770–775; Takaoka, et al. (1999) EMBO J. 18:2480–2488), and stress signals (Tokiwa, et al. (1996) Science 273:792–794). In some cells, tyrosine phosphorylation and activation of PYK2 was shown to be triggered by integrin-mediated adhesion (Astier, et al. (1997) J. Biol. Chem. 272:228–232). Furthermore, PYK2 can be activated by phorbol ester (PMA), or by a variety of extracellular signals that elevate intracellular $Ca^{+2}$ concentration (Lev, et al. (1995) Nature 376:737–745).

It has been proposed that PYK2 acts in concert with Src to link Gi or Gq coupled receptors with the MAP kinase signaling pathway (Dikic, et al. (1996) Nature 383:547–550). Autophosphorylation of Y402 on PYK2 generates a binding site for the SH2 domain of the docking protein Grb2, and subsequent recruitment of the Grb2/Sos complex leads to activation of the Ras/MAP kinase signal transduction cascade (Dikic, et al. (1996) Nature 383:547–550). Activation of the JNK pathway can also be mediated by PYK2, and this signaling pathway can be inhibited by dominant-negative forms of rac and cdc42 (Tokiwa, et al. (1996) Science 273:792–794). In addition, PYK2 activation leads to suppression of outward potassium currents via tyrosine phosphorylation of the delayed rectifier-type potassium channel Kv1.2 (Lev, et al. (1995) Nature 376:737–745). PYK2 also interacts with and phosphorylates a family of phosphatidylinositol transfer proteins, designated Nirs (Lev, et al. (1999) Mol. Cell. Biol. 19:2278–2288), and with a novel ArfGAP, designated Pap (Andreev, et al. (1999) Mol. Cell. Biol. 19:2338–2350), both in vitro and in vivo. In addition, it was shown that activation of PYK2 leads to tyrosine phosphorylation of other proteins that play a role in signal transmission, including the adaptor proteins Shc (Lev, et al. (1995) Nature 376:737–745) and Cas (Astier, et al. (1997) J. Biol. Chem. 272:228–232).

PYK2 is activated by extracellular signals that lead to calcium influx or calcium release from internal stores. PYK2 is phosphorylated on tyrosine residues in response to a variety of external stimuli. PYK2 may provide a link between G-protein coupled receptors and calcium influx and the MAP kinase signaling pathway, a pathway that relays signals from the cell surface to regulate transcriptional events in the nucleus.

In the PCT Publication WO 98/07870 (Avraham, et al.), the authors discuss PYK2 and state that ". . . RAFTK therapeutics which modulate RAFTK activity in B cells, T cells, and monocytes can be used to treat immune-mediated disorders and mediate both cell mediated and humoral immune responses.

Normal hematopoietic cells are dependent on growth factors for growth and differentiation and the loss of this growth factor dependence can lead to autonomous growth. The involvement of RAFTK in several growth factor signaling pathways indicates that misse[x]pression of RAFTK can lead to the development of cancers, and the present invention contemplates modulating RAFTK expression and/or activity to control aberrant cell growth. In a preferred embodiment RAFTK is modulated to treat cancers of hematopoietic cells. In another embodiment malignancy can be suppressed in certain cells e.g., leukemic cells, by modulating RAFTK to induce cellular differentiation . . .

. . . In one embodiment the RAFTK proteins of the present invention can modulate the differentiation or maturation of hematopoietic cells; the subject RAFTK polypeptides are capable of influencing both the differentiation and maturation of pluripotent stem cells and the proliferation of differentiated cells."

SUMMARY OF THE INVENTION

The present invention relates, inter alia, to methods for identification of compounds useful to treat or prevent inflammation-related diseases or disorders characterized by an interaction between a PYK2 polypeptide and a natural binding partner. In addition, the present invention relates to methods for diagnosis and for treatment of inflammation-related diseases or disorders characterized by an interaction between a PYK2 polypeptide and a natural binding partner.

The current invention demonstrates for the first time in an in vivo mouse model and a cellular model the link between PYK2 and the inflammatory response. To demonstrate the role of PYK2 in vivo, knockout mice lacking the pyk2 gene were created using molecular genetic techniques. The inflammatory response of the knockout mice was compared with the corresponding mice not containing a pyk2 deletion. Experiments are described in detail herein in the Detailed Description of the Invention.

The data from these experiments confirm the role for PYK2 in cytokine release and support the importance of PYK2 function in inflammation. These experiments indicate that treatments that inhibit the functioning of PYK2 will be useful to decrease excessive inflammatory responses, whereas treatments to enhance the functioning of PYK2 will be useful to augmnent inadequate immune responses.

In a first aspect, the invention features a method for identifying one or more potential compounds useful to treat or to prevent a disease or disorder, wherein said disease or disorder is characterized by a inflammatory response, wherein said inflammatory response is characterized by an abnormality in a signal transduction pathway, and wherein said signal transduction pathway includes an interaction between a PYK2 polypeptide and a natural binding partner, comprising assaying said one or more potential compounds for those able to modulate said interaction as an indication of a useful said compound.

By "identifying" is meant investigating for the presence or absence of a property. The process may include measuring or detecting various properties, including the level of signal transduction and the level of interaction between a PYK2 polypeptide and a natural binding partner.

The term "compound" preferably refers to a non-peptide organic molecule, and most preferably refers to a non-peptide synthetic organic molecule. The term "non-peptide molecule" refers to a compound that is not a polymer of amino acids. A non-peptide molecule preferably does not contain chemical moieties that hydrolyze in physiological conditions, e.g. a peptidomimetic. Alternatively, a non-peptide molecule may be a peptoid, or modified nucleic acid molecule. Examples of compounds are included in the Description of the Invention, herein. Preferably, such molecules have a molecular weight less than 3,000.

By "inflammatory response" is meant a protective response elicited by injury or destruction of tissues, which serves to destroy, dilute, or wall off (sequester) both the injurious agent and the injured tissue. Histologically, it involves a complex series of events, including dilatation of arterioles, capillaries, and venules, with increased permeability and blood flow; exudation of fluids, including plasma proteins; and leukocyte migration into the inflammatory focus. A pathologic inflammatory response may be a continuation of an acute form or a prolonged low-grade form, and usually causes permanent tissue damage. Macrophage and T-cell recruitment and functions, such as cytokine production, directly contribute to inflammatory pathogenesis. There are many types of diseases and disorders associated with inflammatory responses, all of which are intended to be included under specific embodiments of the present invention.

An "organism" can be single or multi-cellular. The term includes mammals, and, most preferably, humans. Preferred organisms include mice, as the ability to treat or diagnose mice is often predictive of the ability to function in other organisms such as humans.

By "disease or disorder"is meant a state in an organism (e.g., a human) which is recognized as abnormal by members of the medical community. The disease or disorder is characterized by an abnormality in one or more signal transduction pathways in a cell, where the components of the signal transduction pathway include a PYK2 polypeptide and a natural binding partner.

By "abnormality" is meant a level which is statistically different from the level observed in organisms not suffering from such a disease or disorder and may be characterized as either an excess amount, intensity or duration of signal or a deficient amount, intensity or duration of signal. The abnormality in signal transduction may be realized as an abnormality in cell function, viability or differentiation state. Such abnormality in a pathway can be alleviated by action at the PYK2:natural binding partner interaction site in the pathway. An abnormal interaction level may also either be greater or less than the normal level and may impair the normal performance or function of the organism. Thus, it is also possible to screen for agents that will be useful for treating a disease or condition, characterized by an abnormality in the signal transduction pathway, by testing compounds for their ability to affect the interaction between a PYK2 polypeptide and a natural binding partner, since the complex formed by such interaction is part of the signal transduction pathway. However, in some embodiments, the disease or condition may be characterized by an abnormality in the signal transduction pathway even if the level of interaction between the PYK2 polypeptide and natural binding is normal. Further in some embodiments, the defect may result from an inability of a natural binding partner to perform a function on PYK2, or PYK2 to perform a function on a natural binding partner, or both. Finally, in some preferred embodiments, the abnormality does not fall within what is traditionally meant by the signal transduction pathway, e.g. it may involve an activity of PYK2 that does not directly relate to signal transduction.

The term "signal transduction pathway" refers to the molecules that propagate an extracellular signal through the cell membrane to become an intracellular signal. This signal can then stimulate a cellular response. The polypeptide molecules involved in signal transduction processes are typically (but not limited to) receptor and non- receptor protein tyrosine kinases, receptor and non-receptor protein phosphatases, SRC homology 2 and 3 domains, PDZ domain containing proteins, phosphotyrosine binding proteins (SRC homology 2 (SH2) and phosphotyrosine binding (PTB and PH) domain containing proteins), PTB (phosphotyrosine binding) domain that binds to phosphotyrosine as well as non-phosphorylated peptides, PH (pleckstrin homology) domain that binds to phosphoinositides, proline-rich binding proteins (SH3 domain containing proteins), nucleotide exchange factors, and transcription factors.

By "interact" is meant any physical association between polypeptides, whether covalent or non-covalent. This linkage can include many chemical mechanisms, for instance covalent binding, affinity binding, intercalation, coordinate binding and complexation. Examples of non-covalent bonds include electrostatic bonds, hydrogen bonds, and Van der Waals bonds. Furthermore, the interactions between polypeptides may either be direct or indirect. Thus, the association between two given polypeptides may be achieved with an intermediary agent, or several such agents, that connects the two proteins of interest (e.g., a PYK2 polypeptide and a natural binding partner).

Another example of an indirect interaction is the independent production, stimulation, or inhibition of both a PYK2 polypeptide and natural binding partner by a regulatory agent. Depending upon the type of interaction present, various methods may be used to measure the level of interaction. For example, the strengths of covalent bonds are often measured in terms of the energy required to break a certain number of bonds (i.e., kcal/mol). Non-covalent interactions are often described as above, and also in terms of the distance between the interacting molecules. Indirect interactions may be described in a number of ways, including the number of intermediary agents involved, or the degree of control exercised over the PYK2 polypeptide relative to the control exercised over the natural binding partner.

By "a PYK2 polypeptide" is meant the PYK2 polypeptide described in U.S. Pat. No. 5,837,815 to Lev et al. and WO publication WO 96/18738 by Lev et al., both hereby incorporated by reference herein in their entirety including tables, figures, and drawings. The isolation and characterization of the PYK2 polypeptide is also fully described therein. The PYK2 polypeptide can be encoded by a full-length nucleic acid sequence or any portion of the full-length nucleic acid sequence, so long as a functional activity of the polypeptide is retained. Preferred functional activities include, but are not limited to, the ability to phosphorylate and regulate RAK and/or other potassium channels. A variety of methodologies known in the art can be utilized to obtain PYK2 polypeptides for use in the methods of the invention.

The term "natural binding partner" refers to polypeptides, lipids, small molecules, or nucleic acids that bind to kinases in cells. A change in the interaction between a kinase and a natural binding partner can manifest itself as an increased or decreased probability that the interaction forms, or an increased or decreased concentration of kinase/natural binding partner complex. Binding is understood to include interactions such as phosphorylation or dephosphorylation, for example.

The term "modulates" refers to the ability of a compound to alter the interaction of PYK2 and a natural binding partner. The $K_m$ of a compound is preferably between 100 $\mu$M and 1 $\mu$M, more preferably between 1 $\mu$M and 100 nM, most preferably between 100 nM and 1 nM. A modulator preferably promotes or disrupts the interaction of PYK2 and a natural binding partner. Alternatively, the modulator may increase or decrease the cellular activity of the kinase, including phosphorylation.

Kinase activity is preferably the phosphorylation of a natural binding partner on tyrosine, serine, or threonine residues. Changes in the interaction with a natural binding partner can also include increasing or decreasing the probability that a complex forms between the kinase and a natural binding partner. A modulator preferably increases the probability that such a complex forms between the kinase and the natural binding partner, and most preferably decreases the probability that a complex forms between the kinase and the natural binding partner. In some preferred embodiments the interaction includes actions of the natural binding partner on PYK2.

The term "complex" refers to an assembly of at least two molecules bound to one another. Signal transduction complexes often contain at least two protein molecules bound to one another. For instance, a protein tyrosine kinase receptor, GRB2, SOS, RAF, and RAS assemble to form a signal transduction complex in response to a mitogenic ligand.

By "disrupt" is meant that the interaction between the PYK2 polypeptide and a natural binding partner is reduced either by preventing expression of the PYK2 polypeptide, or by preventing expression of the natural binding partner, or by specifically preventing interaction of the naturally synthesized proteins or by interfering with the interaction of the proteins.

By "promote" is meant that the interaction between a PYK2 polypeptide and a natural binding partner is increased either by increasing expression of a PYK2 polypeptide, or by increasing expression of a natural binding partner, or by decreasing the dephosphorylating activity of the corresponding regulatory TP (or other phosphatase acting on other phosphorylated signaling components), by promoting interaction of the PYK2 polypeptide and natural binding partner or by prolonging the duration of the interaction.

The term "activates" refers to increasing the cellular activity of the kinase. The term "inhibit" refers to decreasing the cellular activity of the kinase. Kinase activity is preferably the phosphorylation of a natural binding partner on tyrosine, threonine, or serine residues. Changes in the interaction with a natural binding partner can also include increasing or decreasing the probability that a complex forms between the kinase and a natural binding partner. A modulator preferably increases the probability that such a complex forms between the kinase and the natural binding partner, and most preferably decreases the probability that a complex forms between the kinase and the natural binding partner.

In preferred embodiments of methods for screening for compounds potentially useful for treating or preventing inflammatory response-related diseases or disorders involving the interaction of PYK2 and a natural binding partner, the inflammatory response-related disease or disorder is selected from the group consisting of inflammatory bowel diseases and connective tissue diseases. Preferably, the inflammatory bowel diseases are selected from the group consisting of ulcerative colitis and Crohn's Disease and the connective tissue diseases are selected from the group consisting of rheumatoid arthritis, systemic lupus erythematosus, progressive systemic sclerosis, mixed connective tissue disease, and Sjögren's syndrome.

Macrophage function and the production of cytokines by macrophages and other cells associated with the inflammatory response directly contribute to the pathophysiologic progression of the diseases. The importance of PYK2 in these disease processes is indicated by the decreased production of cytokines in cells from pyk2−/− mice and in macrophage cell lines expressing kinase inactive PYK2. Thus, inhibiting PYK2 function in inflammatory cells should alleviate some of the pathologic consequences associated with these diseases.

The term "inflammatory bowel disease" as used herein, refers to inflammatory diseases of the bowel, many of which are of unknown etiology, including Crohn's disease and ulcerative colitis.

The term "Crohn's Disease" as used herein, refers to a chronic granulomatous inflammatory disease of unknown etiology, involving any part of the gastrointestinal tract from mouth to anus, but commonly involving the terminal ileum and/or colon with scarring and thickening of the bowel wall. It frequently leads to intestinal obstruction and fistula and abscess formation and has a high rate of recurrence after treatment.

By "ulcerative colitis" is meant chronic, recurrent ulceration in the colon, chiefly of the mucosa and submucosa, of unknown cause. The rectum is almost always involved. It is manifested clinically by cramping abdominal pain, rectal bleeding, and loose discharges of blood, pus, and mucus with scanty fecal particles. Complications include hemorroids, abscesses, fistulas, perforation of the colon, pseudopolyps, and carcinoma.

The term "connective tissue diseases" as used herein refers to heterogeneous disorders which share certain common features, including inflammation of skin, joints, and other structures rich in connective tissue, as well as altered patterns of immunoregulation, including production of autoantibodies and abnormalities of cell-mediated immunity. While certain distinct clinical entities may be defined, manifestations may vary considerably from one patient to the next and overlap of clinical features between and among specific diseases is common.

The term "rheumatoid arthritis" as used herein refers to a chronic systemic disease primarily of the joints, usually polyarticular, marked by inflammatory changes in the synovial membranes and articular structures and by muscle atrophy and rarefaction of the bones. Persistent inflammatory synovitis usually involves the peripheral joints in a symmetrical fashion, marked by cartilaginous destruction, bony erosions, and joint deformation. Infiltration of inflammatory cells is common. Forms of rheumatoid arthritis include, but are not limited to, juvenile, chronic villous, cricoarytenoid, deformans, degenerative, mutilans, and proliferative.

The term "systemic lupus erythematosus" as used herein, refers to a disease in which tissues and cells are damaged by deposition of pathogenic antibodies and immune complexes. B-cell hyperactivity, production of autoantibodies with specificity for nuclear antigenic determinants, and abnormalities of T-cell function occur. It may involve virtually any organ system and follows a course of exacerabation followed by remission. A common feature is the alar "butterfly" rash.

The term "progressive systemic sclerosis" as used herein refers to a multisystem disorder characterized by inflammatory, vascular, and fibrotic changes of skin and various internal organ systems (chiefly GI tract, lungs, heart, and kidney). Primary event may be endothelial cell injury with eventual intimal proliferation, fibrosis, and vessel obliteration. Clinical manifestations include, but are not limited to, Raynaud's phenomenon, scleroderma (fibrosis of the skin), hypertension, and renal failure.

The term "mixed connective tissue disease" as used herein, refers to syndrome characterized by a combination of clinical features similar to those of systemic lupus erythematosus, progressive systemic sclerosis, polymyositis, and rheumatoid arthritis. Unusually high titers of circulating antibodies to a nuclear ribonucleoprotein are found. Clinical manifestations include Raynaud's phenomenon, polyarthritis and pulmonary fibrosis among others.

The term "Sjögren's syndrome" as used herein refers to an immunologic disorder characterized by progressive destruction of exocrine glands leading to mucosal and conjunctival dryness (sicca syndrome). Affected tissues show lymphocyte infiltration and immune-complex deposition.

In preferred embodiments of methods of identifying compounds, the one or more compounds modulate (inhibit or promote) the interaction of PYK2 and a natural binding partner in vitro. An example of an in vitro method involves growing cells (i.e., in a dish) that either naturally or recombinantly express a G-coupled protein receptor, PYK2, and RAK. The test compound preferably is added at a concentration from 0.1 $\mu$M to 100 $\mu$M and the mixture preferably is incubated from 5 minutes to 2 hours. The ligand is added to the G-coupled protein receptor preferably for 5 to 30 minutes and the cells are lysed. RAK is isolated using immunoprecipitation or ELISA by binding to a specific monoclonal antibody. The amount of phosphorylation compared to cells that were not exposed to a test compound is measured using an anti-phosphotyrosine antibody (preferably polyclonal). Alternatively, in other methods of identifying compounds, the one or more compounds modulate (inhibit or promote) PYK2 and natural binding partner interactions in vivo.

In other methods of identifying compounds, the interaction is selected from the group consisting of PYK2 phosphorylation, PYK2 natural binding partner phosphorylation, PYK2 de-phosphorylation, PYK2 natural binding partner de-phosphorylation, and complex formation between PYK2 and a natural binding partner.

Examples of compounds that could be tested in such screening methods include tyrphostins, quinazolines, quinoxolines, quinolines, and indolinones. Publications describing representative examples of these compounds and methods of making are given in the Detailed Description of the Invention.

A second aspect of the invention features a method for diagnosis of a disease or disorder, wherein said disease or disorder is characterized by an inflammatory response involving an abnormality in a signal transduction pathway that includes an interaction between a PYK2 polypeptide and a natural binding partner, comprising detecting the level of said interaction as an indication of said disease or disorder.

By "diagnosis" is meant any method of identifying a symptom normally ssociated with a given disease or condition. Thus, an initial diagnosis may be onclusively established as correct by the use of additional confirmatory evidence such as the presence of other symptoms. Current classification of various diseases and conditions is constantly changing as more is learned about the mechanisms causing the diseases or conditions. Thus, the detection of an important symptom, such as the detection of an abnormal level of interaction between PYK2 polypeptides and natural binding partners may form the basis to define and diagnose a newly named disease or condition. For example, conventional cancers are classified according to the presence of a particular set of symptoms. However, a subset of these symptoms may both be associated with an abnormality in a particular signaling pathway, such as the ras[21] pathway and in the future these diseases may be reclassified as ras[21] pathway diseases regardless of the particular symptoms observed.

In preferred embodiments of methods for screening for diagnosis of inflammatory response-related diseases or disorders involving the interaction of PYK2 and a natural binding partner, the inflammatory response-related disease or disorder is selected from the group consisting of inflammatory bowel diseases and connective tissue diseases. Preferably, the inflammatory bowel diseases are selected from the group consisting of ulcerative colitis and Crohn's Disease and the connective tissue diseases are selected from the group consisting of rheumatoid arthritis, systemic lupus erythematosus, progressive systemic sclerosis, mixed connective tissue disease, and Sjögren's syndrome.

A third aspect of the invention features a method for treating or preventing a disease or disorder, wherein said disease or disorder is characterized by an inflammatory response involving an abnormality in a signal transduction pathway that includes an interaction between a PYK2 polypeptide and a natural binding partner, comprising administering to a patient in need of such treatment one or more compounds preferably in a pharmaceutically acceptable composition, wherein said one or more compounds modulate said interaction.

In preferred embodiments of methods for treating or preventing inflammatory response-related diseases or disorders involving the interaction of PYK2 and a natural binding partner, the inflammatory response-related disease or disorder is selected from the group consisting of inflammatory bowel diseases and connective tissue diseases. Preferably, the inflammatory bowel diseases are selected from the group consisting of ulcerative colitis and Crohn's Disease and the connective tissue diseases are selected from the group consisting of rheumatoid arthritis, systemic lupus erythematosus, progressive systemic sclerosis, mixed connective tissue disease, and Sjögren's syndrome.

In other preferred embodiments of the methods for treating or preventing inflammatory response-related diseases or disorders involving the interaction of PYK2 and a natural binding partner, the one or more compounds modulate (inhibit or promote) the interaction in vitro and/or in vivo. In some preferred embodiments, the interaction is selected from the group consisting of PYK2 phosphorylation, PYK2 natural binding partner phosphorylation, PYK2 de-phosphorylation, PYK2 natural binding partner de-phosphorylation, and complex formation between PYK2 and a natural binding partner.

In yet other preferred embodiments of methods for treating or preventing inflammation-related diseases or disorders involving the interaction of PYK2 and a natural binding partner, the one or more compounds is selected from the group consisting of tyrphostins, quinazolines, quinoxolines, quinolines, and indolinones.

In preferred embodiments the agent is therapeutically effective and preferably has an $EC_{50}$, or $IC_{50}$ of less than or equal to 100 $\mu M$, even more preferably less than or equal to 50 $\mu M$, and most preferably less than or equal to 10 $\mu M$. Such lower $EC_{50}$'s or $IC_{50}$'s are advantageous since they allow lower concentrations of molecules to be used in vivo or in vitro for therapy or diagnosis. The discovery of molecules with such low $EC_{50}$'s and $IC_{50}$'s enables the design and synthesis of additional molecules having similar potency and effectiveness. Generally, a therapeutically effective amount is between about 1 nmol and 1 $\mu$mol of the molecule, depending on its $EC_{50}$ or $IC_{50}$, and on the age and size of the patient, and the disease associated with the patient.

The term "preventing" refers to decreasing the probability that an organism contracts or develops an abnormal condition. Thus, in these cases a patient would include someone who is thought to be at risk for contracting an abnormal condition. Persons skilled in the art would be able to identify persons who would be considered at risk from contracting an abnormal condition.

The term "treating" refers to having a therapeutic effect and at least partially alleviating or abrogating an abnormal condition in the organism. In this case the patient is already been identified as having an abnormal condition.

The term "therapeutic effect" refers to the inhibition or activation of factors causing or contributing to the abnormal condition. A therapeutic effect relieves to some extent one or more of the symptoms of the abnormal condition. In reference to the treatment of abnormal conditions, a therapeutic effect can refer to one or more of the following: (a) an increase or decrease in the infiltration of cells; (b) inhibition of (i.e., slowing or stopping) or increase in cell movement; (c) relieving to some extent one or more of the symptoms associated with the abnormal condition; and (d) enhancing or inhibiting the function of the affected population of cells. Compounds demonstrating efficacy against abnormal conditions can be identified as described herein.

The term "abnormal condition" refers to a function in the cells or tissues of an organism that deviates from their normal functions in that organism. An abnormal condition can relate to cell proliferation, cell differentiation, cell function, or cell survival.

Abnormal cell infiltration conditions include, but are not limited to, rheumatoid arthritis and chronic inflammatory bowel disease.

The term "aberration", in conjunction with the function of a kinase in a signal transduction process, refers to a kinase that is over- or under-expressed in an organism, mutated such that its catalytic activity is lower or higher than wild-type protein kinase activity, mutated such that it can no longer interact with a natural binding partner, is no longer modified by another protein kinase or protein phosphatase, or no longer interacts with a natural binding partner.

The term "administering" relates to a method of incorporating a compound into cells or tissues of an organism. The abnormal condition can be prevented or treated when the cells or tissues of the organism exist within the organism or outside of the organism. Cells existing outside the organism can be maintained or grown in cell culture dishes. For cells harbored within the organism, many techniques exist in the art to administer compounds, including (but not limited to) oral, parenteral (e.g. intra-venous, intramuscular, subcutaneous, and intra-articular) and aerosol applications. The compounds may also be administered in a depot or sustained release formulation. For cells outside of the organism, multiple techniques exist in the art to administer the compounds, including (but not limited to) cell microinjection techniques, simple diffuision, and carrier techniques.

The term "pharmaceutically acceptable" or "pharmaceutical" as used herein refers to solutions or components of the pharmaceutical composition that do not prevent the therapeutic compound from exerting a therapeutic effect and do not cause unacceptable adverse side effects. Examples of pharmaceutically acceptable reagents are provided in *The United States Pharmacopeia The National Formulary*, United States Pharmacopeial Convention, Inc., Rockville, Md. 1990 and *FDA Inactive Ingredient Guide* 1990, (1996) issued by the Division of Drug Information Resources (both are hereby incorporated by reference herein, including any drawings). Unacceptable side effects vary for different diseases. Generally, the more severe the disease the more toxic effects which will be tolerated. Unacceptable side effects for different diseases are known in the art.

The term "physiologically acceptable" defines a carrier or diluent that does not cause significant irritation to an organism and preferably does not abrogate the biological activity and properties of the compound.

The term "carrier" defines a chemical compound that facilitates the incorporation of a compound into cells or tissues. For example dimethyl sulfoxide (DMSO) is a commonly utilized carrier as it facilitates the uptake of many organic compounds into the cells or tissues of an organism.

The term "diluent" defines chemical compounds diluted in water (or another solvent) that will dissolve the compound of interest as well as stabilize the biologically active form of the compound. Many salts dissolved in buffered solutions are utilized as diluents in the art. One commonly used buffered solution is phosphate buffered saline because it mimics the salt conditions of human blood. Because buffer salts can control the pH of a solution at low concentrations, a diluent rarely modifies the biological activity of a compound.

The term "solvent" as used herein refers to a chemical compound that facilitates the solubilization of compounds of the invention. Examples of solvents include, but are not limited to, pharmaceutically acceptable alcohols, such as ethanol and benzyl alcohol; polyoxyhydrocarbyl compounds, such as poly(ethylene glycol); pharmaceutically acceptable surfactants such as CREMOPHOR® EL; polyglycolized lipids, such as GELUCIRE® and LABRASOL®; and pharmaceutically acceptable oils, such as miglyol 812.

The term "pharmaceutically acceptable alcohol" as used herein refers to alcohols that are liquids at about room temperature (approximately 20° C.). These include propylene glycol, ethanol, 2-(2-ethoxyethoxy)ethanol (TRANSCUTOL®, Gattefosse, Westwood, N.J. 07675), benzyl alcohol, and glycerol.

The term "polyoxyhydrocarbyl compound" as used herein refers to a water soluble carbohydrate such as glucose, sucrose, maltotriose, and the like; water soluble carbohydrate derivatives such as gluconic acid and mannitol, and oligosaccharides; and water soluble polymers such as polyvinylpyrrolidone, poly(vinyl alcohol), and in particular, polyethers such as other polyoxyalkylenes including poly (ethylene glycol) or other water soluble mixed oxyalkylene polymers and the polymeric form of ethylene glycol. Although polyoxyhydrocarbyl compounds preferably contain more than one carbon, oxygen, and hydrogen atom, some molecules such as poly(ethylene imine) are also included.

A particularly preferred class of solubilizing polyoxyhydrocarbyl moieties comprises poly(ethylene glycol) (PEG) and PEG derivatives, such as PEG monomethyl ether. Other suitable PEG derivatives include PEG-silicon derived ethers. Many of these polymers are commercially available in a variety of molecular weights. Others may be conveniently prepared from commercially available materials, such as by coupling of amino-PEG moiety to a haloalkyl silyl or silane moiety.

Suitable PEGs may vary in molecular weight from about 200 g/mol to about 20,000 g/mol or more, more preferably 200 g/mol to 5,000 g/mol, even more preferably 250 g/mol to 1,000 g/mol, and most preferably 250 g/mol to 500 g/mol. The choice of a particular molecular weight may depend on the particular compound chosen and its molecular weight and degree of hydrophobicity, as well as the particular application for which the formulation is to be used.

The term "pharmaceutically acceptable surfactant" as used herein refers to a compound that can solubilize compounds of the invention into aqueous solutions, if necessary. Preferably for parenteral formulations, the surfactant is a non-ionic surfactant. Examples of pharmaceutically acceptable surfactants include POLYSORBATE 80 and other polyoxyethylene sorbitan fatty acid esters, glyceryl monooleate, polyvinyl alcohol, ethylene oxide copolymers such as PLURONIC® (a polyether) and TETRONIC® (BASF), polyol moieties, and sorbitan esters. Preferably ethoxylated castor oils, such as CREMOPHOR® EL, are used for the formulation of some compounds.

The term "ethoxylated castor oil" as used herein refers to castor oil that is modified with at least one oxygen containing moiety. In particular the term refers to castor oil comprising at least one ethoxyl moiety.

Further, the term "pharmaceutically acceptable surfactant" as used herein in reference to oral formulations, includes pharmaceutically acceptable non-ionic surfactants (for example polyoxyethylene-polypropylene glycol, such as POLOXAMER® 68 (BASF Corp.) or a mono fatty acid ester of polyoxyethylene (20) sorbitan monooleate (TWEEN® 80), polyoxyethylene (20) sorbitan monostearate (TWEEN® 60), polyoxyethylene (20) sorbitan monopalmitate (TWEEN® 40), polyoxyethylene (20) sorbitan monolaurate (TWEEN® 20) and the like); polyoxyethylene castor oil derivatives (for example, polyoxyethyleneglycerol-triricinoleate or polyoxyl 35 castor oil (CREMOPHOR® EL, BASF Corp.), polyoxyethyleneglycerol oxystearate (CREMOPHOR® RH 40 (polyethyleneglycol 40 hydrogenated castor oil) or CREMOPHOR® RH 60 (polyethyleneglycol 60 hydrogenated castor oil), BASF Corp.) and the like); or a pharmaceutically acceptable anionic surfactant.

The term "polyglycolized lipids" as used herein refers to mixtures of monoglycerides, diglycerides, or triglycerides and polyethyleneglycol monoesters and diesters formed by the partial alcoholysis of vegetable oil using PEG of 200 g/mol to 2,000 g/mol or by the esterification of fatty acids using PEG 200 g/mol to 2,000 g/mol and glycerols. Preferably these include GELUCIRE® 35/10, GELUCIRE® 44/14, GELUCIRE® 46/07, GELUCIRE® 50/13, GELUCIRE® 53/10, and LABRASOL®.

The term "pharmaceutically acceptable oils" as used herein refers to oils such as mineral oil or vegetable oil (including safflower oil, peanut oil, and olive oil), fractionated coconut oil, propylene glycol monolaurate, mixed triglycerides with caprylic acid and capric acid, and the like. Preferred embodiments of the invention feature mineral oil, vegetable oil, fractionated coconut oil, mixed triglycerides with caprylic acid, and capric acid. A highly preferred embodiment of the invention features Miglyol® 812 (available from Huls America, USA).

In preferred embodiments, the methods described herein involve identifying a patient in need of treatment. Those skilled in the art will recognize that various techniques may be used to identify such patients.

A fourth aspect of the invention features a composition comprising one or more compounds identified by any of the methods of the invention described above or herein. Preferably, this composition is useful for treating or preventing a disease or disorder, where the disease or disorder is characterized by an inflammatory response involving an abnormality in a signal transduction pathway that includes an interaction between a PYK2 polypeptide and a natural binding partner.

In preferred embodiments, the inflammatory response-related disease or disorder is selected from the group consisting of inflammatory bowel diseases and connective tissue diseases. Preferably, the inflammatory bowel diseases are selected from the group consisting of ulcerative colitis and Crohn's Disease and the connective tissue diseases are selected from the group consisting of rheumatoid arthritis, systemic lupus erythematosus, progressive systemic sclerosis, mixed connective tissue disease, and Sjögren's syndrome.

A fifth aspect of the invention features methods of making compounds potentially useful to treat or to prevent a disease or disorder, where the disease or disorder is characterized by an inflammatory response that is characterized by an abnormality in a signal transduction pathway, and where the signal transduction pathway includes an interaction between a PYK2 polypeptide and a natural binding partner, comprising assaying one or more potential compounds for those able to modulate the interaction as an indication of a useful compound and synthesizing the identified compounds. References describing methods of synthesizing the identified compounds are indicated in the Detailed Description of the Invention.

In preferred embodiments, the inflammatory response-related disease or disorder is selected from the group consisting of inflammatory bowel diseases and connective tissue diseases. Preferably, the inflammatory bowel diseases are selected from the group consisting of ulcerative colitis and Crohn's Disease and the connective tissue diseases are selected from the group consisting of rheumatoid arthritis, systemic lupus erythematosus, progressive systemic sclerosis, mixed connective tissue disease, and Sjögren's syndrome.

A sixth aspect of the invention features kits comprising a composition comprising one or more compounds identified by any of the methods of the invention described above or herein. Preferably, this composition is useful for treating or preventing a disease or disorder, where the disease or disorder is characterized by an inflammatory response involving an abnormality in a signal transduction pathway that includes an interaction between a PYK2 polypeptide and a natural binding partner. The kit preferably further comprises instructions for use either on a label or using other suitable means as discussed herein in the Detailed Description of the Invention.

In other preferred embodiments, the kit comprises additional container means containing one or more of the following: diluents, carriers, and solvents. Such containers include small glass containers, plastic containers, or strips of plastic or paper. Such containers allow the efficient transfer of contents from one container to another, such that the contents are not contaminated and the contents can be added in a quantitative fashion from one compartment to another. The kit may additionally comprise means for administering the composition. One skilled in the art will readily recognize that the compositions of the instant invention can be readily incorporated into one of the established kit formats that are well-known in the art.

In preferred embodiments, the composition contained in the kit is useful for treating or preventing an inflammatory response-related disease or disorder selected from the group consisting of inflammatory bowel diseases and connective tissue diseases. Preferably, the inflammatory bowel diseases are selected from the group consisting of ulcerative colitis and Crohn's Disease and the connective tissue diseases are selected from the group consisting of rheumatoid arthritis, systemic lupus erythematosus, progressive systemic sclerosis, mixed connective tissue disease, and Sjögren's syndrome.

Other features and advantages of the invention will be apparent from the following description of the preferred embodiments thereof, and from the claims.

BRIEF DESCRIPTION OF THE FIGURES

These figures are provided for illustration only, and are not considered necessary to disclose the invention.

FIG. 1b shows Southern blot hybridization analysis of the mouse tail DNA digested with Apal. FIG. 1c shows immunoblot analysis with anti-PYK2 antibodies of lysates from Thymus(T), Brain (B), and Spleen (S) from wild-type, pyk2+/−, and pyk2−/− mice. FIG. 1d shows an immunoblot analysis of tissue lysates of FAK from wild type or PYK2−/− mice. B, Brain; T, Thymus; S, spleen; H, Heart; K, Kidney; L, Lung.

FIGS. 4a and 4b demonstrate Carageenen induced cellular infiltration in murine air pouches. FIG. 4a shows a number of cells infiltrating into wild type +/+ and pyk2−/− air pouches 10 hours after injection with Carageenen. FIG. 4b shows a fraction of cells infiltrating into wild-type +/+ and pyk2−/− mice air pouches 10 hours after injection with Carageenen.

FIG. 5 shows the time course of the survival of mice at different doses of influenza virus.

FIGS. 6a and 6b show the tyrosine phosphorylation of PYK2 in macrophage cell lines in response to LPS (lipopolysaccharide) and tyrosine kinase inhibitors. Cells were either starved overnight in 0.5% serum and stimulated with LPS for variable time intervals (FIG. 6a), or were pre-treated with either herbimycin A or genestein for 4 hours and then stimulated with LPS for 30 minutes (FIG. 6b). After stimulation, cells were washed, lysed, and immunoprecipitated with anti-PYK2 antibody. Immunoprecipitates (IP) were then analyzed by western blotting.

FIGS. 7a, 7b, 7c, and 7d demonstrate that expression of both the PYK2 wild-type and the dominant negative kinase mutant are inducible in P388D1 cells. The murine macrophage cell line (P388D1) was serially transfected with doxycycline (DOX) inducible plasmids. In the first transfection, a regulator plasmid was introduced, and stable, drug-resistant clones were established. Two clones were then selected and transfected with doxycycline-responsive plasmids containing either HA-tagged hemagglutinin), wild-type PYK2 or the kinase dead, dominant-negative PYK2 mutant also HA-tagged). After drug selection, stable clones containing the wild-type (FIGS. 7b and 7d) or the dominant-negative mutant (FIGS. 7a and 7c) were screened for expression of the appropriate protein in the presence (FIGS. 7a and 7b) and absence (FIGS. 7c and 7d) of doxycyclin by western blotting.

FIGS. 8a and 8b show the effect of LPS in the presence and absence of DOX on TNF-α secretion from kinase mutant (dominant negative; FIG. 8a) and wild-type (FIG. 8b) cells. FIGS. 8c and 8d show the effect of PMA in the presence and absence of DOX on TNF-α secretion from kinase mutant (FIG. 8c) and wild-type (FIG. 8d) cells. Induction of P388D1 cells in the presence of doxicycline was carried out for 48 hours followed by stimulation with LPS (1 μg/mL) or PMA (1 μg/mL) for 18 hrs. Secreted TNF-α was measured by ELISA.

FIGS. 9a and 9b show measurement of contractile capacity of lamellipodia in wild type or PYK2-/- macrophages by laser tweezers. FIG. 9a shows plots of bead displacement from leading edge as a function of time. Fibronectin coated beads were positioned with tweezers on the lamellipodia of PYK2-/- or wild type macrophages of unstimulated (top panels) or MIP1α-stimulated (bottom panels) cells near the leading edge at time 0. The trap remained on for approximately 60 sec. as indicated by shaded area. Two upper plots present beads displacement on non-stimulated macrophages and two lower plots present displacement on MIP1α-stimulated macrophages. FIG. 9b shows a histogram of ratio (%) of beads displaying escape from trapped field by laser tweezer. All the beads on the lamellipodia of PYK2-/- or wild type macrophages before and after stimulation by MIP1α were subjected to a restraining force after initial bead-cell contact for 60 sec. Ratios of beads which escaped and moved rearward were scored. Left column shows score of non-stimulated macrophages and right column shows score of MIP1α-stimulated macrophages.

FIGS. 10a, 10b and 10c show a comparison of cell signaling in wild type and PYK2-/- deficient macrophages. For FIG. 10a, PYK2-/- and wild type macrophages were plated on fibronectin coated dishes for 0.5, 1 and 2 hour, then lysed and incubated with GST-RBD(rho-binding domain) bound to gluthatione beads as described in material and methods. The amount of rhoA: GTP complex was determined by immunoblotting with anti-rhoA antibodies. FIG. 10b shows $Ca^{+2}$ release in PYK2-/- or wild type macrophages. Macrophages loaded by fura-2 were stimulated by MIP1α in Ringer's solution with 2 mM calcium. Changes in fluorescence intensity as a function of time were traced in the fura-2 loaded cells following stimulation with MIP1α or ATP. FIG. 10c shows production of $Ins(1,4,5)P_3$ in wild type or PYK2-/- macrophages. Wild type or PYK2-/- macrophages were labeled with myo-[$^3$H]inositol for 24 hours. After MIP1α stimulation the lipid fraction was extracted and analyzed by HPLC. Closed square indicate production of inositol (1,4,5) triphosphate in wild type macrophages and open circle indicate production of inositol (1,4,5) triphosphate in PYK2-/- macrophages. The experiment was done in duplicates and repeated three times.

FIGS. 11a and 11b show data related to myelin oligodendrocyte glycoprotein induced experimental autoimmune encephalomyelitis (MOG-induced EAE). FIG. 11a shows that both wild type and PYK2-/- mice were susceptible to MOG-induced EAE. FIG. 11b shows that the proliferative response toward MOG was delayed in T-cells from draining lymph nodes from PYK2-/- mice as compared to T-cells from wild type mice.

DETAILED DESCRIPTION OF THE INVENTION

I. PYK2 and Signal Transduction

Figure 1A:
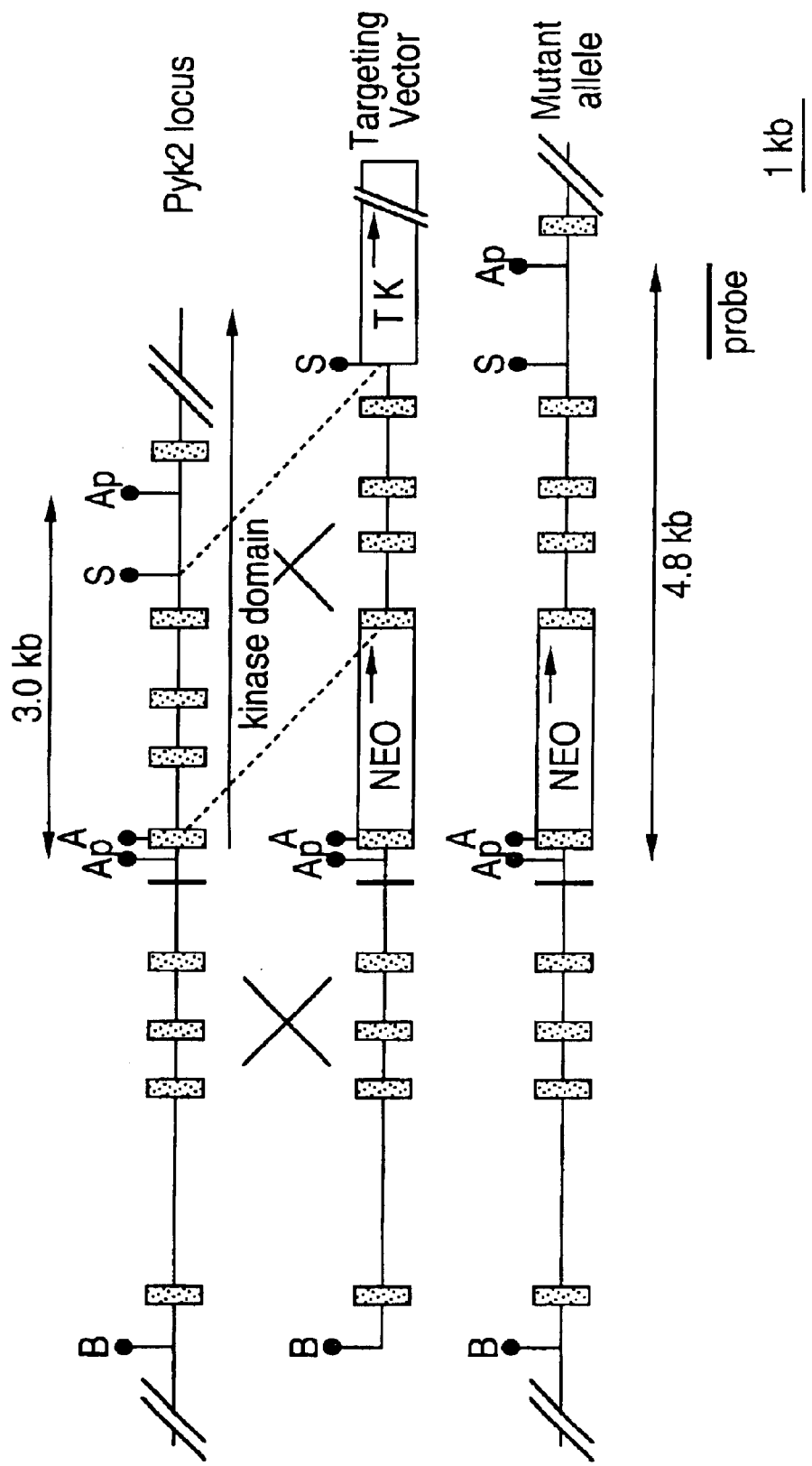
FIGS. 1a, 1b, 1c and 1d show the targeted disruption of the pyk2 gene in mice. Partial restriction maps of murine pyk2 locus, the regions used as a targeting vector, and the expected mutant allele are shown in FIG. 1a. Solid boxes indicate exons. The probe was used for Southern blot hybridization analysis of the genomic DNA from the ES cells and tail biopsy analysis. The solid line under the pyk2 locus marks the PYK2 kinase domain. Arrows mark the expected Apal fragments of the wild-type and mutant alleles.

PYK-2 is a non-receptor tyrosine kinase that is activated by binding of ligand to G-coupled protein receptors such as bradykinin, acetylcholine, and CXCR4 or CCR5. PYK2 has a predicted molecular weight of 111 kD and contains five domains: (1) a relatively long N-terminal domain; (2) a kinase catalytic domain; (3) a proline rich domain; (4) another proline rich domain; and (5) a C-terminal domain.

The C-terminal domain of PYK2 has 62% similarity to the C-terminal domain of another non-receptor tyrosine kinase, focal adhesion kinase (FAK), which is also activated by G-coupled proteins. The overall similarity between PYK2 and FAK is 52%. However, the expression of PYK2 does not correspond with the expression of FAK. PYK2 exhibits diffuse cytoplasmic localization unlike the preferential localization of Fak in focal adhesion areas. PYK2 is expressed in a variety of cells including neural tissues, hematopoietic cells, some tumor cell lines, and immune-related cells. PYK2 is highly expressed in the nervous system and in the adult rat brain.

PYK2 enzymatic activity is positively regulated by phosphorylation on tyrosine and results in response to binding of bradykinin, TPA, calcium ionophore, carbachol, TPA+forskolin, and membrane depolarization. Activated PYK2 is known to phosphorylate and thus suppress the activity of the delayed rectifier-type K+channel, termed RAK (also called Kvi.2, RBK2, RCK5 and NGKI), that is highly expressed in the brain and cardiac atria. In the same system, FAK does not phosphorylate RAK. PYK2 activation may provide a rapid and highly localized control mechanism for ion channel function and kinase activation induced by stimuli that elevate intracellular calcium.

PYK2 is activated by, and phosphorylated on tyrosine residues in response to a variety of extracellular signals that lead to calcium influx or calcium release from internal stores resulting in elevation of intracellular $Ca^{2+}$ concentration. Calcium influx leads to the activation of PYK2, tyrosine phosphorylation of Shc, recruitment of Grb2/Sos and activation of the MAP kinase signaling pathway that relays signals to the cell nucleus. Overexpression of PYK2 also leads to activation of MAP kinase. PYK2 has also been shown to be activated by peptide hormones that bind to G-protein coupled receptors that mediate their intracellular responses via Gi and Gq type of G-proteins (Lev, et al. (1995) *Nature* 376:737–745). Thus, PYK2 may provide a link between G-protein coupled receptors and calcium influx and the MAP kinase signaling pathway; a pathway that relays signals from the cell surface to regulate transcriptional events in the nucleus.

Additionally, in certain cells PYK2 is activated by integrin mediated cell adhesion (Astier, et al. (1997) *J. Biol. Chem.* 272:228–232).

These results reveal a role for PYK2 in activation of the MAP kinase signaling pathway by ion channels, calcium influx and G-protein coupled receptors and provide a mechanism for signal transduction induced by these stimuli. Furthermore, tyrosine phosphorylation of Shc in response to membrane depolarization and carbachol treatment was dependent on the presence of extracellular calcium, indicating that calcium-influx plays a role in regulation of Shc phosphorylation by these stimuli.

Similarly, PYK2 may modulate the action of ion channels that mediate their responses via and are sensitive to intracellular calcium concentration. PYK2 may therefore provide an autoregulatory role for the very same channel responsible for PYK2 activation.

The expression pattern of PYK2 and the external stimuli that activate this kinase together with its role in the control of MAP kinase signaling pathway, suggests a potential role for PYK2 in the control of a broad array of processes.

Since PYK2 activity is regulated by intracellular calcium level, both the temporal and spatial pattern of PYK2 activation may represent a carbon copy or a replica of the spatial and temporal profile of intracellular calcium concentration. Calcium concentration inside cells is highly localized because of a variety of calcium binding proteins that provide a strong buffer. Moreover, in excitable cells the level of calcium can be regulated by voltage dependent calcium channels that induce large and transient increase in intracellular calcium concentration leading to calcium oscillations and calcium waves. PYK2 may provide a mechanism for rapid and highly localized control of ion channel function, as well as, localized activation of the MAP kinase signaling pathway.

II. Knockout Mice Lacking PYK2

The current invention demonstrates for the first time in an in vivo mouse model and a cellular model the link between PYK2 and the inflammatory response. To demonstrate the role of PYK2 in vivo, knockout mice lacking the pyk2 gene were created using molecular genetic techniques. FIG. 1 shows the altered size of a fragment of the pyk2 gene following the knockout procedure along with the lack of PYK2 expression in mice which are PYK2–/–. Additionally, Northern blot hybridization analysis of total RNA isolated from PYK2–/– brain, thymus and spleen tissues did not reveal any PYK2 expression.

PYK2–/– homozygous mice were fertile and did not show gross anatomical abnormalities compared to wild-type littermates, including tissues that normally express high levels of PYK2, such as the brain, thymus, and spleen. Further analysis of lymphoid subpopulations by flow cytometry did not reveal any obvious difference in the distribution of T-cells, B-cells, macrophage-monocytes, or NK cells in any lymphoid tissue, including spleen, lymph node, thymus, bone marrow, and peritoneal cavity. Serum levels of IgG1, IgG2a, IgG3, IgM and IgA were also similar in /PYK2–/– and wild-type littermates.

In the influenza model, the inflammatory response of the knockout mice was compared with the corresponding mice not containing a pyk2 deletion following infection with the influenza virus which leads to an overwhelming pulmonary inflammatory response and eventually death. It was found that the pyk2 knockout mice survived significantly longer than control mice expressing the pyk2 gene (48 hours). Histologic examination of the lungs of the knockout and control mice showed that in the lungs of the pyk2 knockout mice there was a significantly lower infiltration of inflammatory cells including PMNs (polymorphonuclear leukocytes), macrophages, and T-cells. In vitro experiments showed that macrophages and splenocytes from pyk2–/– mice produced decreased amounts of cytokines and chemokines, including IL-1α, IL-1β, IL-6, IL-10, TNF-α, GMCSF, IFN-γ, and MIP1-α. Lower production of cytokines and chemokines such as TNF-α and MIP1-α (among others) results in attenuated recruitment and decreased activation of macrophages, T-cells and other hematopoietic and nonhematopoietic cells involved in the inflammatory response. In addition, macrophages from knockout mice had decreased motility in vitro. The attenuated cytokine response and migration defect in vitro correlate with the enhanced survival and decreased pulmonary cellular infiltrate in pyk2–/– mice following influenza challenge.

In the subcutaneous carageenen air pouch model, a subcutaneous air pouch is surgically induced on the hind flank of the mouse. The air pouch is then filled with the immunogen carageenen, a substance that induces an inflammatory response. After 10 hours, the number and type of cells infiltrating the pouch are enumerated. Histologic examination revealed a decrease in the number of cells infiltrating the carageenen filled pouch of pyk2–/– mice compared to controls. In addition there was a significant decrease in the number of macrophages present at the site of inflammation.

To evaluate the role of PYK2 in mature macrophage cells that express wild-type PYK2, kinase inactive PYK2 protein was introduced into a normal macrophage cell line. Expression of the kinase inactive PYK2 should function as a "dominant-negative" inhibitor and abrogate the function of the endogenous wild-type PYK2 protein in these macrophages. Expression of the kinase inactive PYK2 protein decreased secretion of TNF-α in response to LPS, a physiologically relevant inducer of the inflammatory response.

Defect in Cell Signaling in PYK2–/– Macrophages

The experiments presented below show that several intracellular signals that are stimulated by chemokines are impaired in PYK2–/– macrophages. We found that chemokine-induced production of Ins(1,4,5)P$_3$ as well as other inositol phospholipids is impaired. In addition, chemokine-induced Ca$^{+2}$ release and MAP kinase activation are also impaired. In certain cell types intracellular release of Ca$^{+2}$ leads to strong activation of PYK2 (Lev, et al. (1995) *Nature* 376:737–745). Taken together, these experiments suggest that PYK2 can function both as a Ca$^{+2}$ sensor as well as an element crucial for the control of Ca$^{+2}$ release.

Impairment in Macrophage Contractility and Locomotion Caused by PYK2 Deficiency

The migration of cells in culture in response to extracellular stimuli can be divided into a five-step cycle: (i) extension of the leading edge towards to stimulus; (ii) adhesion of the leading edge to the substrate, (iii) movement of the cytoplasm towards the leading edge, (iv) release from contact sites at the lagging edge and (V) recycling of membrane receptor from the lagging edge to the leading edge of the cell (Sheetz, et al. (1999) *Biochem. Soc. Symp.* 65:233–243). Each step of the cycle requires orderly changes in cytoskeletal structures and focal contacts, a process that is regulated by a variety of intracellular enzymes including protein tyrosine kinases and protein tyrosine phosphatases (Manes, et al. (1999) *Mol. Cell. Biol.* 19:3125–3135).

The experiments described below demonstrate that in macrophages PYK2 plays an important role in the control of cell migration. In fact, it appears that PYK2−/− macrophages display alterations in most steps of the migration cycle. In PYK2−/− macrophages, extension of the leading edge is delayed, and multiple extensions are generated (steps i and ii). Furthermore, PYK2−/− macrophages inefficiently detach the lagging edge from the matrix to allow net movement (steps iv and v). It appears that the migration of the cytoplasm is also impaired in the PYK2 deficient macrophages. Alterations in the migration cycle are particularly evident after the initial extension of lamellipodia, and altered cell polarization, which could be observed as multi directional lamellipodia and redistribution of F-actin in multiple sites.

The strength of the traction force in the lamellipodia of wild type or PYK2−/− macrophages was analyzed by applying the laser tweezer method (Choquet, et al. (1997) *Cell* 88:39–48). The ability of plasma membrane bound beads to move rearward on the cell surface in opposition to the restraining force imposed by the force field of the laser provides a measurement for the ability of cells to migrate over a fixed point on the matrix. Measurements of bead movements on wild type or PYK2−/− lamellipodia revealed the diminished capacity of integrin/cytoskeletal complex in PYK2−/− macrophages to supply the contractile force necessary for cell migration. This can be caused by decreased tightness of the linkage between integrin and the cytoskeleton or decreased contractile force of the cytoskeleton or decreases in both processes. It appears that aberrant adhesion and diminished traction force in PYK2−/− macrophages will stabilize lamellipodia that would normally be retracted resulting in the disruption of cellular polarization and migration.

It is thought that cells subjected to a chemotactic gradient are "sampling" the environment by extending lamellipodia in several directions. Stable attachments to the extracellular matrix are formed in the direction of the highest concentration of the stimulus, whereas other larnellipodia eventually retract into the cell. The maintenance of an appropriate cellular polarization in a gradient thus requires regulation of contact stability and contractile capacity of the lamellipodia. In PYK2−/− macrophages both process are impaired.

Aberrant regulation of the stability of contacts in PYK2−/− macrophages leads to increased adherence of extended lamellipodia to the substratum and impairment in subsequent retraction even when the lamellipodia extends for the purpose of "sampling" the environment into a direction which does not contain a high concentration of chemokine. Increase in the stability of contacts may result in change in cell polarization.

PYK2 Deficiency Impairs rho Activation and Causes Cytoskeletal Changes

Cell morphological change such as contraction of lamellipodia or formation of contact require vigorous changes in cytoskeleton. Numerous studies have indicated that members of the rho family of GTPases play an important role in modulating the cytoskeleton in response to extracellular stimuli. Rho GTPases were implicated in the control cytoskeletal organization, actomyosin contraction, vesicle transport, phospholipid production (Exton, et al. (1997) *Eur. J. Biochem.* 243:10–20) as well as in the control of integrin clustering (Hotchin and Hall (1995) *J Cell. Biol.* 131:1857–1865; Renshaw, et al. (1996) *J. Biol. Chem.* 271:21691–21694). In this report we show that activation of rho in response to integrin-mediated cell adhesion on fibronectin is impaired in PYK2−/− macrophages. Moreover, formation of long processes and decreased cell contraction displayed by PYK2−/− macrophages also occur in wild type macrophages that were treated with a specific rho inhibitor. Since activation of rho has been shown to be critical for contraction of lamellipodia (Kimura, et al. (1996) *Science* 273:245–248), the decreased contractility in PYK2−/− macrophages could be due to decreased activity of rho.

Degradation of molecules and disassembly of F-actin at the rear end of migrating macrophages are required for cell detachment from the substratum.

Intracellular calcium plays an important role in this process by regulating the activity of calpain and gelsolin (Witke, et al. (1995) *Cell* 81:41–51; Huttenlocher, et al. (1997) *J Biol. Chem.* 272:32719–32722). The attenuated chemokine-induced calcium release caused by PYK2 deficiency may lead to the impairment of detachment of the rear end of migrating cell.

Phagocytotic cells such as macrophages or neutrophils as well as lymphocytes migrate quickly into inflammatory regions in response to chemokines and other cues. Recruited inflammatory cells produce a battery of cytokines and a variety of inflammatory mediators such as oxygen radicals, nitric oxide and lipid mediators, which induce inflammatory reaction and systematic effects. The onset of experimental allergic encephalitis (EAE) induced by injection of a peptide corresponding to myelin specific protein requires appropriate migration of macrophages into primary inflammatory region that was triggered by infiltrated TH1 cells. Experiments presented in this report demonstrate that the onset of EAE was delayed by approximately two days in PYK2 deficient mice. However, although EAE was delayed in PYK2 deficient mice the outcome of the disease was more severe in these mice. It is also demonstrated that the infiltration of macrophages into carageenen induced inflammatory region is strongly inhibited in PYK2−/− mice. Taken together, both the in vitro and in vivo experiments presented in this study reveal an important regulatory role for PYK2 in normal function of macrophages.

The above data confirm the role for PYK2 in cytokine release and support the importance of PYK2 function in inflammation. These experiments indicate that treatments that inhibit the functioning of PYK2 will be useful to decrease excessive inflammatory responses, whereas treatments to enhance the functioning of PYK2 will be useful to augment inadequate immune responses.

III. Identification of Compounds that Modulate PYK2

The present invention relates, inter alia, to methods of detecting compounds that modulate the interaction of PYK2 with its natural binding partners. The modulation can encompass either a decrease, or an increase in the interaction between PYK2 and its natural binding partners. The compounds thus identified would be useful in the prevention or treatment of immune-related disorders involving the signal transduction system and in particular interactions among PYK2 and its natural binding partners. The compounds may be present within a complex mixture, for example, serum, body fluid, or cell extracts. Once the compounds are identified, they can be isolated using techniques well known in the art.

The present invention also encompasses a method of treating or preventing immune-related diseases in a mammal with one or more compounds, that modulate PYK2:natural binding partner interactions, comprising administering the compounds to a mammal in an amount sufficient to modulate PYK2:natural binding partner interactions.

In an effort to discover novel treatments for diseases, biomedical researchers and chemists have designed, synthesized, and tested molecules that inhibit the function of protein kinases. Some small organic molecules form a class of compounds that modulate the function of protein kinases. Examples of molecules that have been reported to inhibit the function of protein kinases include, but are not limited to, bis monocyclic, bicyclic or heterocyclic aryl compounds (PCT WO 92/20642, published Nov. 26, 1992 by Maguire, et al.), vinylene-azaindole derivatives (PCT WO 94/14808, published Jul. 7, 1994 by Ballinari, et al.), 1-cyclopropyl-4-pyridyl-quinolones (U.S. Pat. No. 5,330,992), styryl compounds (U.S. Pat. No. 5,217,999), styryl-substituted pyridyl compounds (U.S. Pat. No. 5,302,606), certain quinazoline derivatives (EP Application No. 0 566 266 A1), selenoindoles and selenides (PCT WO 94/03427, published Feb. 17, 1994 by Denny, et al.), tricyclic polyhydroxylic compounds (PCT WO 92/21660, published Dec. 10, 1992 by Dow), and benzylphosphonic acid compounds (PCT WO 91/15495, published Oct. 17, 1991 by Dow, et al.), all of which are hereby incorporated by reference herein including any figures, drawings, or tables.

Compounds that can traverse cell membranes and are resistant to acid hydrolysis are potentially advantageous as therapeutics as they can become highly bioavailable after being administered orally to patients. However, many of these protein kinase inhibitors only weakly inhibit the function of protein kinases. In addition, many inhibit a variety of protein kinases and will therefore cause multiple side-effects as therapeutics for diseases.

Some indolinone compounds, however, form classes of acid resistant and membrane permeable organic molecules. WO 96/22976 (published Aug. 1, 1996 by Ballinari, et al.; hereby incorporated by reference herein including any figures, drawings, or tables) describes hydrosoluble indolinone compounds that harbor tetralin, naphthalene, quinoline, and indole substituents fused to the oxindole ring. These bicyclic substituents are in turn substituted with polar moieties including hydroxylated alkyl, phosphate, and ether moieties. PCT Publication WO 98/07695, published Mar. 26, 1998 by Tang, et al. (Lyon & Lyon Docket No. 221/187 PCT), PCT Publication WO 96/40116, published Dec. 19, 1996 by Tang, et al. (Lyon & Lyon Docket No. 223/298), and International Patent Publication WO 96/22976, published Aug. 1, 1996 by Ballinari, et al., all of which are incorporated herein by reference in their entirety, including any drawings, figures, or tables describe indolinone chemical libraries of indolinone compounds harboring other bicyclic moieties as well as monocyclic moieties fused to the oxindole ring. They also teach methods of indolinone synthesis, methods of testing the biological activity of indolinone compounds in cells, and inhibition patterns of indolinone derivatives.

Other examples of substances capable of modulating kinase activity include, but are not limited to, tyrphostins, quinazolines, quinoxolines, and quinolines. The quinazolines, tyrphostins, quinolines, and quinoxolines referred to above include well known compounds such as those described in the literature. For example, representative publications describing quinazolines include Barker, et al., EPO Publication No.0 520 722 A1; Jones, et al., U.S. Pat. No. 4,447,608; Kabbe, et al., U.S. Pat. No. 4,757,072; Kaul and Vougioukas, U.S. Pat. No. 5,316,553; Kreighbaum and Comer, U.S. Pat. No. 4,343,940; Pegg and Wardleworth, EPO Publication No. 0 562 734 A1; Barker, et al. (1991) *Proc. of Am. Assoc. for Cancer Research* 32:327; Bertino, J. R. (1979) *Cancer Research* 3:293–304; Bertino, J. R. (1979) *Cancer Research* 9(2 part 1)293–304; Curtin, et al. (1986) *Br. J. Cancer* 53:361–368; Fernandes, et al.(1983) *Cancer Research* 43:1117–1123; Ferris, et al. *J. Org. Chem.* 44(2), 173–178; Fry, et al. (1994) *Science* 265:1093–1095; Jackman, et al. (1981) *Cancer Research* 51:5579–5586; Jones, et al. *J. Med. Chem.* 29(6), 1114–1118; Lee and Skibo (1987) *Biochemistry* 26(23), 7355–7362; Lemus, et al. (1989) *J. Org. Chem.* 54:3511–3518; Ley and Seng, (1975) *Synthesis* 1975:415–522; Maxwell, et al. (1991) *Magnetic Resonance in Medicine* 17:189–196; Mini, et al. (1985) *Cancer Research* 45:325–330; Phillips and Castle (1980) *J. Heterocyclic Chem.* 17(19), 1489–1596; Reece, et al. (1977) *Cancer Research* 47(11), 2996–2999; Sculier, et al. (1986) *Cancer Immunol. and Immunother.* 23, A65; Sikora, et al. (1984) *Cancer Letters* 23:289–295; Sikora, et al. (1988) *Analytical Biochem.* 172:344–355; all of which are incorporated herein by reference in their entirety, including any drawings.

Quinoxaline is described in Kaul and Vougioukas, U.S. Pat. No. 5,316,553, incorporated herein by reference in its entirety, including any drawings.

Quinolines are described in Dolle, et al. (1994) *J. Med. Chem.* 37:2627–2629; MaGuire (1994) *J. Med. Chem.* 37:2129–2131; Burke, et al. (1993) *J. Med. Chem.* 36:425–432; and Burke, et al. (1992) *BioOrganic Med. Chem. Letters* 2:1771–1774, all of which are incorporated by reference in their entirety, including any drawings.

Tyrphostins are described in Allen, et al. (1993) *Clin. Exp. Immunol* 91:141–156; Anafi, et al. (1993) *Blood* 82, 12, 3524–3529; Baker, et al. (1992) *J. Cell Sci.* 102:543–555; Bilder, et al. (1991) *Amer. Physiol. Soc.* 6363–6143, C721–C730; Brunton, et al. (1992) *Proceedings of Amer. Assoc. Cancer Rsch.* 33:558; Bryckaert, et al. (1992) *Experimental Cell Research* 199:255–261; Dong, et al. (1993) *J. Leukocyte Biology* 53:53–60; Dong, et al. (1993) *J. Immunol.* 151(5), 2717–2724; Gazit, et al. (1989) *J. Med. Chem.* 32:2344–2352; Gazit, et al. (1993) *J. Med. Chem.* 36:3556–3564; Kaur, et al. (1994) *Anti-Cancer Drugs* 5:13–222; King, et al. (1991) *Biochem. J.* 275:413–418; Kuo, et al. (1993) *Cancer Letters* 74:197–202; Levitzki, A. (1992) *The FASEB J.* 6:3275–3282; Lyall, et al. (1989) *J. Biol. Chem.* 264:14503–14509; Peterson, et al. (1993) *The Prostate* 22:335–345; Pillemer, et al. (1992) *Int. J. Cancer* 50:80–85; Posner, et al. (1993) *Molecular Pharmacology* 45:673–683; Rendu, et al. (1992) *Biol. Pharmacology* 44(5), 881–888; Sauro and Thomas, (1993) *Life Sciences* 53:371–376; Sauro and Thomas (1993) *J. Pharm. and Experimental Therapeutics* 267(3), 119–1125; Wolbring, et al. (1994) *J. Biol. Chem.* 269(36), 22470–22472; and Yoneda, et al. (1991) *Cancer Research* 51:4430–4435; all of which are incorporated herein by reference in their entirety, including any drawings.

Other compounds that could be used as modulators include oxindolinones such as those described in U.S. patent application Ser. No. 08/702,232 filed Aug. 23, 1996 and indolinones such as those described in U.S. Pat. No. 5,792,783 issued Aug. 11, 1998, entitled "3-Heteroaryl-2-Indolinone Compounds for the Treatment of Disease" (Lyon & Lyon Docket No. 223/301, both of which are hereby incorporated herein by reference in their entirety, including any drawings, figures or tables.

IV. Pharmaceutical Formulations and Routes of Administration

The compounds described herein can be administered to a human patient per se, or in pharmaceutical compositions where they are mixed with other active ingredients, as in combination therapy, or suitable carriers or excipient(s).

Techniques for formulation and administration of the compounds of the instant application may be found in "Remington's Pharmaceutical Sciences," Mack Publishing Co., Easton, Pa., latest edition. Preferred routes include oral, transdermal, and parenteral delivery.

a) Routes of Administration

Suitable routes of administration may, for example, include depot, oral, rectal, transmucosal, or intestinal administration; parenteral delivery, including intramuscular, subcutaneous, intravenous, intramedullary injections, as well as intrathecal, direct intraventricular, intraperitoneal, intranasal, or intraocular injections.

Alternately, one may administer the compound in a local rather than systemic manner, for example, via injection of the compound directly into a solid tumor, often in a depot or sustained release formulation.

Furthermore, one may administer the drug in a targeted drug delivery system, for example, in a liposome coated with tumor-specific antibody. The liposomes will be targeted to and taken up selectively by the tumor.

b) Composition/Formulation

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries that facilitate processing of the active compounds into preparations that can be used pharmaceutically. Proper formulation is dependent upon the route of administration chosen.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by adding a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic compounds of the invention is a cosolvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:D5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various types of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Many of the PTK modulating compounds of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents that are the corresponding free base forms.

c) Effective Dosage

Pharmaceutical compositions suitable for use in the present invention include compositions where the active ingredients are contained in an amount effective to achieve its intended purpose. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

For any compound used in the methods of the invention, the therapeutically effective dose can be estimated initially from cell culture assays. For example, a dose can be formulated in animal models to achieve a circulating concentration range that includes the $IC_{50}$ as determined in cell culture (i.e., the concentration of the test compound which achieves a half-maximal inhibition of the PTK activity). Such information can be used to more accurately determine useful doses in humans.

Toxicity and therapeutic efficacy of the compounds described herein can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds which exhibit high therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See e.g., Fingl, et al. (1975) *The Pharmacological Basis of Therapeutics* Ch. 1 p.1).

Dosage amount and interval may be adjusted individually to provide plasma levels of the active moiety which are sufficient to maintain the kinase modulating effects, or minimal effective concentration (MEC). The MEC will vary for each compound but can be estimated from in vitro data; e.g., the concentration necessary to achieve 50–90% inhibition of the kinase using the assays described herein. Dosages necessary to achieve the MEC will depend on individual characteristics and route of administration. However, HPLC assays or bioassays can be used to determine plasma concentrations.

Dosage intervals can also be determined using MEC value. Compounds should be administered using a regimen that maintains plasma levels above the MEC for 10–90% of the time, preferably between 30–90% and most preferably between 50–90%.

In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

d) Packaging

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in a form prescribed by a governmental agency regulating the manufacture, use, or sale of pharmaceuticals, which notice is reflective of approval by the agency of the form of the compound for human or veterinary administration. Such notice, for example, may be the labeling approved by the U.S. Food and Drug Administration or other government agency for prescription drugs, or the approved product insert. Compositions comprising a compound of the invention formulated in a compatible pharmaceutical carrier may also be prepared, placed in an appropriate container, and labeled for treatment of an indicated condition. Suitable conditions indicated on the label may include, for example, treatment of immune-related diseases including inflammation, and the like.

V. Target Diseases to be Treated or Diagnosed by Methods of the Invention

Target diseases to be treated or diagnosed by the methods of the invention are generally those that have an aberrant inflammatory response. A pathologic inflammatory response may be a continuation of an acute inflammatory response or a prolonged low-grade inflammatory response, and usually causes permanent tissue damage. Macrophage and T-cell recruitment and functions, such as cytokine production, directly contribute to inflammatory pathogenesis. There are many types of diseases and disorders associated with inflammatory responses, both acute and chronic, all of which are intended to be included under specific embodiments of the present invention.

Specific diseases of interest include, but are not limited to the following:

Inflammatory bowel diseases include ulcerative colitis and Crohn's disease. The majority of cases of ulcerative colitis are mild, being limited to rectosigmoid involvement. However clinical manifestations include bloody diarrhea, mucus, fever, abdominal pain, tenesmus, and weight loss. Complications can include toxic megacolon, colonic perforation, and cancer. The level of risk of cancer is related to the extent and duration of colitis, and may be preceded by dysplasia. Intractable disease (to drug treatment), toxic megacolon, cancer and severe dysplasia may require a colectomy.

Crohn's disease is generally more serious, occurring in any part of the GI tract with transmural inflammation, bowel wall thickening, linear ulcerations, granulomas, fissures and fistulas. Clinical manifestations include fever, abdominal pain, diarrhea, fatigue, weight loss, acute ilietis, anorectal fissures, fistulas, and abscesses. Complications may include intestinal obstruction, intestinal fistulas, and intestinal malignancy. Treatments include parenteral nutrition as well as pharmaceuticals including corticosteroids, immunosuppressive agents, and metronidazole. Surgery may be required for fixed obstruction, abscesses, persistent symptomatic fistulas, and intractability.

Connective tissue diseases involve inflammation of the connective tissue as well as altered patterns of immunoregulation.

Rheumatoid arthritis is a serious health care problem. Progressive arthritic conditions in humans cause severe pain, loss of joint mobility and disfigurement, and an overall reduction in the quality of life. In rheumatoid arthritis, the synovium hyperproliferates (aided by new blood vessels) and invades the cartilage which is destroyed. Conventional treatment for rheumatoid arthritis includes non-steroidal anti-inflammatory drugs (NSAIDs). A need exists for an effective treatment for rheumatoid arthritis that will disrupt disease progression in addition to suppression or amelioration of symptoms.

Clinical manifestations of systemic lupus erythematosus include fatigue, fever, malaise, weight loss, skin rashes (malar "butterfly" rash), photosensitivity, arthritis, myositis, oral ulcers, vasculitis, alopecia, anemia, neutropenia, thrombocytopenia, lymphadenopathy, splenomegaly, organic brain syndromes, seizures, psychosis, pleuritis, pericarditis, myocarditis, pneumonitis, nephritis, venous or arterial thrombosis, mesenteric vasculitis, and sicca syndrome. There is currently no cure. treatment is directed at controlling generalized inflammation. Drugs include salicylates and NSAIDs. New, effective drugs are desperately needed.

Clinical manifestations of progressive systemic sclerosis include Raynaud's phenomenon, scleroderma, telangiectasis, calcinosis, esophageal hypomotility, arthralgias and/or arthritis, intestinal hypofunction, pulmonary fibrosis, hypertension, and renal failure. Renal failure is the leading cause of death. There is no definitive therapy.

Clinical manifestations of the mixed connective tissue disease include Raynaud's phenomenon, polyarthritis, sclerodactyly, esophageal dysfunction, pulmonary fibrosis, and inflammatory myopathy. treatment is directed to controlling the inflammatory process in general.

Clinical manifestations of Sjögren's syndrome include xerostomia and keratoconjunctivitis sicca, nephritis, vasculitis, polyneuropathy, interstitial pneumonitis, pseudolymphoma, autoimmune thyroid disease, and congenital cardiac conduction defects in women with SSA antibodies. Treatment includes symptomatic relief of dryness as well as treatments associated with autoimmune phenomena.

Although the primary target diseases to be treated or diagnosed by the methods of the invention are those that have an aberrant inflammatory response, other diseases that involve alterations in macrophage or macrophage-like cell function (i.e. osteoclast) are also intended to be included. Examples of diseases that are not considered to be classic inflammatory response-mediated diseases include, but are not limited to, osteoarthritis, osteoperosis, osteopetrosis and atherosclerosis.

VI. Other Embodiments

Methods for evaluation of disorders, methods for monitoring changes in cells, methods of identifying compounds, methods of isolating compounds which interact with a PTK, compositions of compounds that interact with a PTK, and derivatives of complexes are disclosed in detail with respect PYK-2 in PCT publication WO 96/18738 and U.S. Pat. No. 5,837,815. These publications are hereby incorporated herein by reference in their entirety, including any drawings, tables, or figures. Those skilled in the art will appreciate that such descriptions are applicable to the present invention and can be easily adapted to it. Those skilled in the art will also appreciate that any modifications made to a complex can be manifested in a modification to any of the molecules in that complex. Thus, the invention includes any modifications to nucleic acid molecules, polypeptides, antibodies, or compounds in a complex.

In addition, the WO 96/18738 provides disclosure describing the recombinant DNA techniques pertaining to the present invention, nucleic acid vectors, the nucleic acid elements of these vectors, the types of cells that can harbor these vectors, methods of delivering these vectors to cells or tissues, methods of producing and purifying antibodies, methods of constructing hybridomas that produce these antibodies, methods of detecting signaling molecule complexes, methods of detecting interactions with natural binding partners, antibodies to complexes, disruption of PTK protein complexes, purification and production of complexes, transgenic animals containing nucleic acid vectors encoding a PTK, antisense and ribozyme approaches, and gene therapy techniques. Those skilled in the art will readily appreciate that such descriptions are applicable to the present invention and can be easily adapted to it.

Other methods associated with the invention are described in the examples disclosed herein.

EXAMPLES

The examples below are non-limiting and are merely representative of various aspects and features of the proce dures used to demonstrate the role of PYK-2 in signal transduction in inflammation.

Materials and Methods

Chemicals

Bradykinin, pertusis toxin, cholera toxin, forskolin, phorbol 12-myristate 13-acetate (PMA), calcium ionophore A23187, carbachol, muscarine, atrophine, mecamylamine, and 1,1-dimethyl-4-phenyl piperazinium iodide (DMPP) were purchased from Sigma.

Cells and Cell Culture

PC12-rat pheochromocytoma cells were cultured in Dulbecco's modified Eagle's medium containing 10% horse serum, 5% fetal bovine serum, 100 µg/mL streptomycin and 100 units of penicillin/mL. NIH3T3, 293, GP+E-86 and PA317 cells were grown in Dulbecco's modified Eagle's medium containing 10% fetal bovine serum, 100 µg/mL streptomycin and 100 units of penicillin/mL.

Antibodies

Antibodies against PYK2 were raised in rabbits immunized (HTI) either with a GST fusion protein containing residues 362–647 of PYK2 or with a synthetic peptide corresponding the 15 amino acids at the N-terminus of PYK2. Antisera were checked by immunoprecipitation and immunoblot analysis. The specificity was confirmed either by reactivity to the related protein Fak or by competition with the antigenic or control peptides. The antibodies were found to be specific to PYK-2; they do not cross react with FAK.

Transfections and Infections

For stable expression in PC12 cells, PYK2 was subcloned into the retroviral vector pLXSN (Miller and Rosman, Biotechniques 7:980, (1989)). The construct was used to transfect GP+E-86 cells using lipofectamine reagent (GIBCO BRL). 48 hours after transfection, virus containing supernatants were collected. Pure retrovirus-containing cell-free supernatants were added to PC12 cells in the presence of polybrene (8 µg/mL, Aldrich) for 4 hours (MCB 12 491, 1992). After 24 hours, infected PC12 cells were split into growing medium containing 350 µL/mg G418. G418 resistant colonies were isolated two to three weeks later and the level of expression was determined by Western blot analysis.

Stable cell lines of NIH3T3 that overexpress PYK2 were established by cotransfection of PYK2 subcloned into pLSV together with pSV2neo utilizing lipofectamine reagent (GIBCO BRL). Following transfection, the cells were grown in Dulbecco's modified Eagle's medium containing 10% fetal bovine serum and 1 mg/mL G418. Transient transfections into 293 cells were performed by using a calcium phosphate technique, standard in the art.

Constructs

GST-PYK2

A DNA fragment of λ900 bp corresponding to residues 362–647 of PYK2 was amplified by PCR utilizing he following oligonucleotide primers (SEQ ID NO: 1) 5'-CGGGATCCTCATCATCCATCCTAGGAAAGA-3' (sense) and (SEQ ID NO: 2) 5'-CGGGAATTCGTC GTAGTCCCAGCAGCGGGT-3' (antisense).

PYK2

The full length cDNA sequence of PYK2 was subcloned into the following mammalian expression vectors: pLSV; downstream from the SV40 early promoter, pLXSN-retroviral vector; downstream from the Mo-MuLV long terminal repeat; pRK5; downstream from the CMV promoter.

PYK2-HA

The influenza virus hemagglutinin peptide (SEQ ID NO: 3)(YPYDVPDYAS) was fused to the C-terminus of PYK2 utilizing the following oligonucleotide primers in the PCR reaction: (SEQ ID NO: 4) 5'-CACAATGTCTTCAAACGC CAC-3' and (SEQ ID NO: 5) 5'-GGCTCTAGATCACGA TGCGTAGTCAGGGACATCGTATGGGRACTCTGCA GGTGGGTGGGGCCAG-3'. The amplified fragment was digested with Rsrll and XbaI and was substituted with the corresponding fragment of PYK2. The nucleotide sequence of the final construct was confirmed by DNA sequencing.

Kinase negative mutant/Dominant-negative

In order to construct a kinase negative mutant, Lys (457) was substituted to Ala by site directed mutagenesis utilizing the 'Transformer Site-Directed mutagenesis Kit' (Clontech). The oligonucleotide sequence was designed to create a new restriction site of NruI. The nucleotide sequence of the mutant was confirmed by DNA sequencing. The oligonucleotide sequence that was (SEQ ID NO: 6) used for mutagenesis was: 5'–

Immunoprecipitation and Immunoblot Analysis

Cells were lysed in lysis buffer containing 50 mM N-2-hydroxyethylpiperazine-N'-2-ethanesulferic acid (HEPES pH 7.5), 150 mM NaCl, 10% glycerol, 1% Triton X-100, 1.5 mM $MgCl_2$, 1 mM ethyleneglycol-bis (β-aminoethyl ether)-N,N,N'N'-tetraacetic acid (EGTA), 10 µg leupeptin per mL, 10 µg aprotinin per mL, 1 mM phenylmethylsulfonyl fluoride (PMSF), 200 µM sodium orthovanadate and 100 mM sodium fluoride. Immunoprecipitations were performed using protein A-sepharose (Pharmacia) coupled to specific antibodies. Immunoprecipitates were washed either with HNTG' solution (20 mM HEPES buffer at pH 7.5, 150 mM NaCl, 10% glycerol, 0.1% Triton X-100, 100 mM sodium fluoride, 200 µM sodium orthovanadate) or successively with H' solution (50 mM Tris-HCl pH 8, 500 mM NaCl, 0.1% SDS, 0.2% Triton X-100, 100 mM NaF, 200 µM sodium orthovanadate) and L' solution (10 mM Tris-HCl pH 8, 0.1% Triton X-100, 100 mM NaF, 200 µM sodium orthovanadate). The washed immunoprecipitates were incubated for 5 min with gel sample buffer at 100° C. and analyzed by sodium dodecyl sulfate polyacrylamide gel electrophoresis (SDS-PAGE). In some experiments, the gel-embedded proteins were electrophoretically transferred onto nitrocellulose. The blot was then blocked with TBS (10 mM Tris pH 7.4, 150 mM NaCl) that contained 5% low fat milk and 1% ovalbumin. Antisera or purified mAbs were then added in the same solution and incubation was carried out for 1 h at 22 ° C. For detection, the filters were washed three times (5 min each wash) with TBS/0.05% Tween-20 and reacted for 45 min at room temperature with horseradish peroxidase-conjugated protein A. The enzyme was removed by washing as described above, and the filters were reacted for 1 min with a chemiluminescence reagent (ECL, Amersham) and exposed to an autoradiography film for 1–15 min.

In Vitro Kinase Assay

This was carried out on immunoprecipitates in 50 µL HNTG (20 mM Hepes pH 7.5, 150 mM NaCl, 20% glycerol, 0.1% Triton X-100) containing 10 mM $MnCl_2$ and 5 µCi or [mN-$^{32}$P]ATP for 20 min at 22 ° C. The samples were washed with H', M' and, L' washing solutions, boiled for 5 min in sample buffer and separated by SDS-PAGE.

Construction of Targeting Vector

A mouse genomic DNA clone corresponding to the N-terminal domain and the kinase domain, was isolated from 129 strain P1 phage library (Genom Systems). 4.5 kb BamH1-Acc1 genomic DNA fragment encoding the 5' terminal of the kinase domain was inserted a XhoI site, flanking to a neo expression cassette in the pPNT vector (Soriano, et al. (1991) *Cell* 64:693–702) and 2 kb AccI-SacI genomic DNA fragment was inserted to BamHI site flanking to HSV thymidine kinase expression cassette in the pPNT vector.

Electroporation of ES Cells and Generation of PYK2−/− Mice

R1 ES cells were grown on mitomycin C-treated primary embryonic fibroblast that are extracted from day 15 embryos at 37° C. in Dulbecco's modified Eagles Medium (DMEM) supplemented with 15% heat inactivated fetal bovine serum (Hyclone), 0.1 mM 2-mercaptoethanol, 1 mM sodium pyruvate, and $10^3$ U/ml leukemia inhibitory factor. (LIF) (GIBCO). Cells ($7 \times 10^6$) were electroporated in 800 µl of phosphate-buffered saline(PBS) with 32 µg of NotI linealized targeting vector DNA at 240V, 500 mF using Gene Pulser (Bio-Rad) and plated on gelatin coated plastic dishes. After 48 hours, the cells were transferred to growth medium supplemented with G418 (150 mg/ml) (GIBCO) and Gancyclovir (2 mg/ml) (Syntex). G418- and Gancyclovir resistant colonies were picked up 10–12 days after electroporation. Homologous recombination was screened by Southern blot hybridization. Four independently mutated ES cells clones were used in embryo aggregation experiments for generation of mice. Chimeric mice were crossed to 129Sv/Ev females and germ line transmission in heterozyous mice was identified in two independent ES cell clone derived F1 mice by Southern blot analysis. Heterozygote mice were intercrossed to produce homozygote mice.

Cell Culture 2.0 ml of 3% Brewer thioglycollate (GIBCO) medium was injected into peritoneal cavity 4 days prior to cell harvest. The inflammatory cells, comprised of mixture of macrophages and neutrophils, were harvested from euthanized animals as lavage by PBS. Macrophages were isolated as an adherent cells after plating harvested cells onto tissue cultured dishes.

Immunofluorescence Analysis

Peritoneal exudate cells were incubated on coverslips for 60 minutes. The non-adherent cells were washed off and the adherent cells were treated for 1 hr with MIP1α or SDF1α (R&D systems) using by Zigmond glass slide chamber (Neuroprobe, Cobin John, MD). The cells before and after treatment were fixed with 4% paraformaldehyde, permabilized with 0.1% Triton X and stained with TRITC-conjugated phalloidin (Sigma) to visualize F-actin distribution. The slides were analyzed using the Leica TCS confocal microscope and images collected using Leica TCS User software. Images were further processed using NIH Image 1.61 and Adobe Photoshop.

Migration Assays

Thioglycollate-induced peritoneal macrophages were plated on tissue culture dishes and after addition of 100 ng/ml MIP1α, image of migrating macrophages on the heated plate at 37° C. were captured every 10 minutes using CCD camera equipped with Nikon Diaphot Inverted Microscope and processed using NIH image software.

Experimental Inflammation in Air Pouch Model

The air pouch experiments were conducted essentially as described previously (Wisniewski, et al. (1996) *J Immunol.* 156:1609–1615). Briefly, air pouches were induced on the back of wild type and PYK2−/− mice by three subcutaneous injections of air every second day. To induce an acute inflammation, 1 ml of a 2% (w/v) carrageenen solution in the saline was injected directly into the air pouch. After 10 hour, the mice were sacrificed. 2 ml saline was injected into each air pouch, and the exudate was aspirated. Aliquots were diluted with saline and the cells were counted. Further, air pouch was dissected, fixed and stained by hematoxyline cosine. Three arbitrarily selected fields each containing approximately 300 cells were distinguished morphologically and counted per each mouse.

Microinjection

Cells were injected in Hepes-buffered culture medium at room temperature using a Zeiss (Oberkochen, Germany) Axiopvert 35 microscope, an Eppendorf (Hamburg, Germany) micromanipulator 5170, a microinjector 5242 and Sutter capillaries (Novato, Calif.). The holding pressure was 450 hPa, the injection pressure was 500 hPa and the duration of the injection was 200 ms. The concentration of microinjected protein was 1–2 mg/ml in PBS. After microinjection, cells were incubated in DMEM at 37° C.

[$^3$H]Inositol Phospholipids and $Ca^{2+}$ Analyses

Cells grown in 6-well plates were labeled for 24 h in medium-199 containing myo-[$^3$H]inositol(20 µCi/ml). The cells were washed once with PBS and pre-incubated for 10 min. in 2 ml of PBS containing 10 mM LiCl (PH 7.4) at 37° C. prior to the addition of chemokines. The cells were extracted with methanol/1M HCl/chloroform 1:1:1 and analyzed by high-performance liquid chromatography (HPLC) as described (Falasca, et al. (1998) *EMBO J.* 17:414–422). [$Ca^{2+}$] i measurements were performed in single macrophages as described (Falasca, et al. 1995).

Laser Trapping Experiments

For laser trap experiments, beads were prepared as described (Choquet, et al. (1997) *Cell* 88:39–48; Felsenfeld, et al. (1999) *Nature Cell Biology* 1:200–206). Briefly, carboxylated latex beads (0.91 µm; Polyscience) were derivitized with carbodimide and coated with ovalbumin (Sigma). The ovalbumin was further derivitized with covalently linked biotin (Sulpho NHS-LC biotin; Pierce) to permit the binding of avidin (Neutravidin; Molecular Probes) and finally, a recombinant fragment of fibronectin (FN type 3 domains 7–10; FNIII7–10; including the binding site for the integrin α5 β1).

The optical gradient laser trap was formed using a titanium-sapphire laser (800 nM; Coherent) which was excited with an argon ion laser (5W; Coherent). The 800 nM laser beam was focused through the bottom port of a Zeiss Axiovert100 TV to form a trap that was parfocal with the image plane of the microscope. Bead position was visualized using a newvicon camera (MTI Dage) processed through a Hamamatsu Argus 10 image processor for background subtraction and contrast stretching. Video data were collected at 30 frames per second on an SVHS VCR for subsequent analysis. Analysis of bead position was carried out using single particle tracking routines (Gelles; 1987) implemented in the ISEE image analysis software package (Innovision) running on an O2 workstation (Silicon Graphics Inc.).

Beads were placed at ~0.5 mm from the edge of the lamellipodia using a 30 mW (20 pN) trap. The laser trap remained activated until the bead had moved >500 nm from the trap center. Beads that moved <500 nm in 30 s.

Analysis of rho Activation

Measurement of amount of rho-GTP was performed as previously described (Ren, et al. (1999) *EMBO J.* 18:578–585). Briefly, macrophages plated on the fibronectin were washed with ice-cold PBS and lysed in RIPA buffer (50 mM Tris, pH7.2, 1% Triton X-10, 0.5% sodium deoxycholate, 0.1% SDS, 150 mM NaCl, 10 mM $MgCl_2$, 10 mM/ml each leupeptin and aprotinin, and 1 mM PMSF). Cell lysates were centrifuged at 13,000 g at 4° C. for 10 min and incubated with GST-RBD (20 µg) beads at 4° C. for 45 min. The beads were washed four times with washing buffer (Tris buffer containing 1% Triton X-100, 150 mM NaCl, 10 mM MgCl$_2$, 10 µg/ml each leupeptin and aprotinin, and 0.1 mM PMSF). Bound Rho proteins were detected by immunoblotting using a polyclonal antibody against rho-A (Santa Cruz Biotechnology).

EAE Induction

EAE was induced by subcutaneous injection at the base of the tail of 100 µg MOG 35–55 peptide emulsified in complete Freund's Adjuvant and supplemented with 2 mg/ml heat-killed M.tuberculosis H37RA (Difco). Pertussis toxin (200 ng/dose; Sigma) was injected intravenously at the time of MOG injection and 40 hours later.

Clinical signs of EAE were monitored according to Baron, et al. (1993): 1: limp tail; 2: hind leg weakness; 3: total hind leg paralysis; 4: front leg weakness; 5: moribund. Lymphocyte cultures: At various time-points, single-cell suspensions from draining (periaortic) and mesenteric lymphnodes were prepared separately and seeded at $10^6$ cells/ml in 96 well plates and analyzed for proliferation to stimulation with anti CD3/28 (1 µg/ml) and to 5 µM MOG 35–55 peptide. After 48 hours in culture, plates were pulsed with 1 µCi[$^3$H] thymidine (NEN) for 6 hours, harvested, and read in a betaplate (Wallac). Culture supernatants were collected at 24, 48, 72 hours and IL-2, IL-4, IL-10 and IFN-γ accumulation was assessed by ELISA using antibody pairs recommended by Pharmingen. Data was collected from individual mice (two mice per time-point).

CNS-Infiltrating leukocytes were prepared after total bleeding of the mice, cerebellum and spinal cord dissection, incubation with collagenase D (400 U/ml, Boehringer Mannheim) for 45 minutes at 37° C. and centrifugation in 38% Percoll (Pharmacia). The pellet was washed twice and stained with anti-Mac1, anti-panCD45, anti I.A.$^b$, anti-granulocyte (Gr-1), anti-CD3, and anti-B220, antibodies (Pharmingen).

Example I

PYK2 Knockout Experiments

Figure 1B:
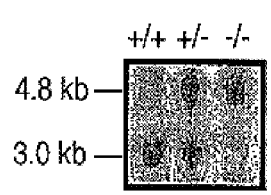
Figure 1C:
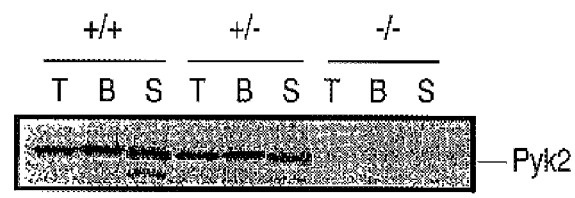
Figure 1D:
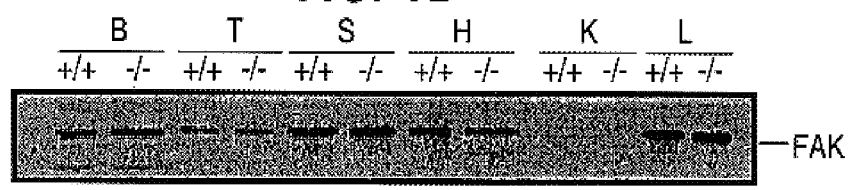

The Pyk2 gene was knocked out of mice by targeted disruption. FIG. 1a shows partial restriction maps of murine Pyk2 locus, the regions used as a targeting vector, and the expected mutant allele. Solid boxes indicate exons. The probe was used for Southern blot hybridization analysis of the genomic DNA from the ES cells and tail biopsy analysis. The solid line under the Pyk2 locus marks the Pyk2 kinase domain. Arrows mark the expected Apal fragments of the wild-type and mutant alleles. Southern blot hybridization analysis of the mouse tail DNA digested with Apal indicates that the Pyk2 knockout was successful (FIG. 1b). Immunoblot analysis (with anti-Pyk2 antibodies) of lysates from Thymus (T), Brain (B), and Spleen (S) from wild-type, Pyk2 +/−, and Pyk2−/− mice also demonstrated the absence of Pyk2 polypeptide in knockout mice (FIG. 1c).

Example II

Analysis of Cytokine Production

RT-PCR (reverse transcriptase-polymerase chain reaction) was used to analyze cytokine productions from wild-type +/+ and Pyk2−/− thioglycollate-elicited peritoneal macrophages stimulated by LPS. Thioglycollate-elicited peritoneal macrophages were incubated with or without LPS (10 µg/mL) for 3 h, 6 h, 12 h, 24 h, and 48 h. Total RNAs were isolated from cells at each time point. After normalization of the amount of mRNA in the total RNAs by RT-PCR of actin mRNA, total RNAs were subjected to RT-PCR with specific probes for various cytokines.

Figure 2:
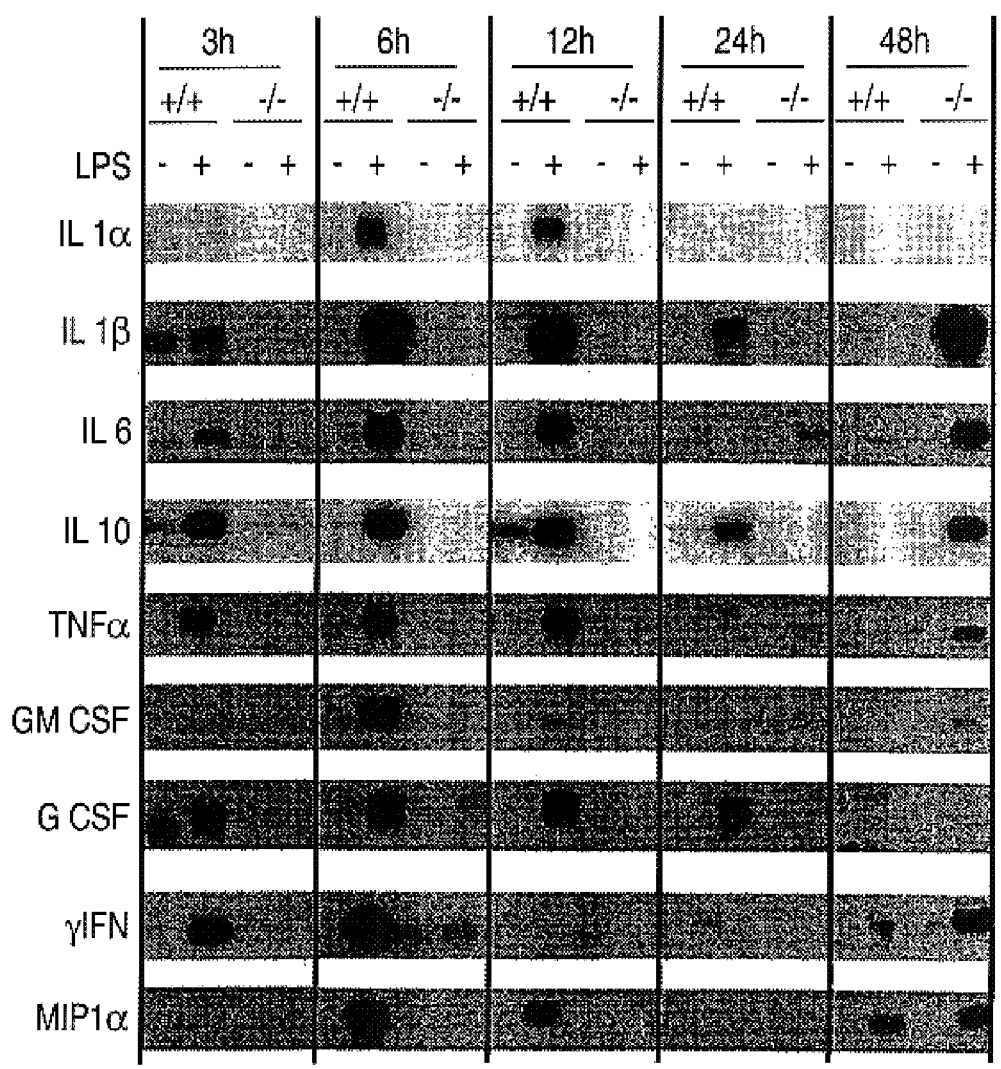
FIG. 2 shows RT-PCR (reverse transcriptase-polymerase chain reaction) analysis of cytokine productions from wild-type +/+ and pyk2−/− thioglycollated-elicited peritoneal macrophages stimulated by LPS. Thioglycollate-elicited peritoneal macrophages were incubated with or without LPS (10 μg/mL) for 3 h, 6 h, 12 h, 24 h, and 48 h. Total RNAs were isolated from cells at each time point and after normalization of the amount of mRNA in the total RNAs by RT-PCR of actin mRNA, total RNAs were subjected to RT-PCR with specific probes for various cytokines.

This experiment reveals a long delay of 24 to 48 hours in the onset of production of cytokines in macrophages derived from PYK2−/− mice (FIG. 2).

RT-PCR analysis was also used to determine the cytokine productions from wild-type +/+ and Pyk2−/− splenocytes stimulated by anti-murine CD3 antibodies. Splenocytes were incubated with or without anti-CD3 (1 µg/mL) for 12 h, 24 h, 48 h and 72 h. Total RNAs were isolated from cells at each time point. After normalization of the amount of mRNA in the total RNAs by RT-PCR of the actin mRNA, total RNAs were subjected to RT-PCR with specific probes for various cytokines.

Figure 3:
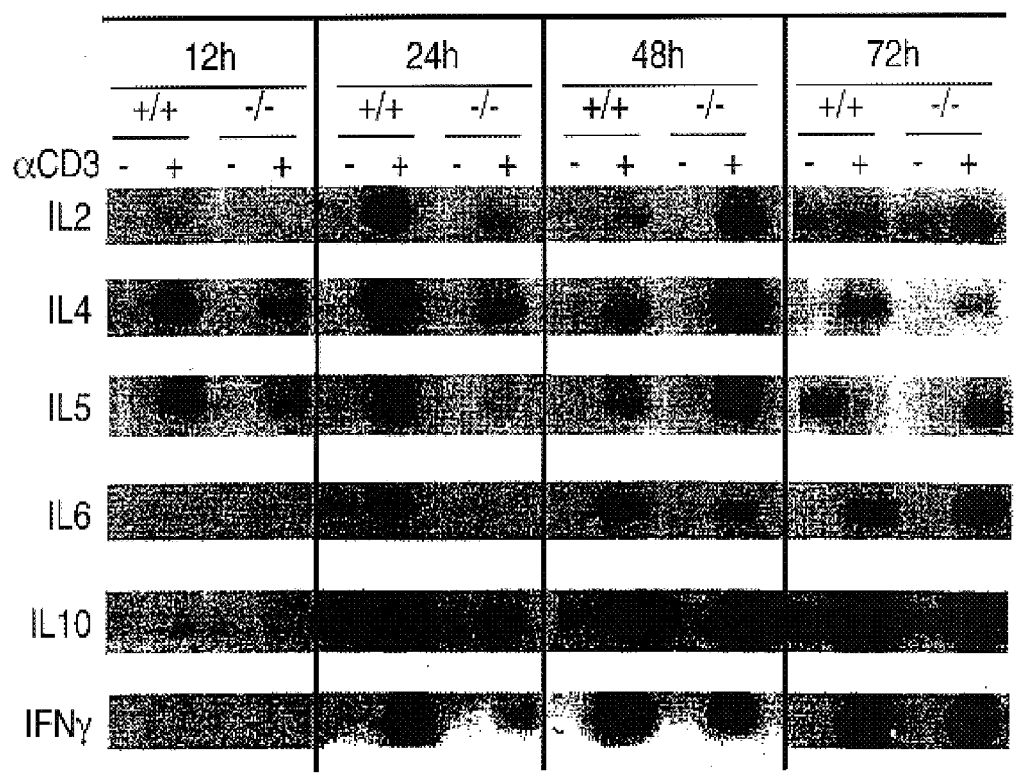
FIG. 3 shows RT-PCR analysis of the cytokine productions from wild-type +/+ and pyk2−/− splenocytes stimulated by anti-murine CD3 antibodies. Splenocytes were incubated with or without anti-CD3 (1 μg/mL) for 12 h, 24 h, 48 h and 72 h. Total RNAs were isolated from cells at each time point and after normalization of the amount of mRNA in the total RNAs by RT-PCR of the actin mRNA, total RNAs were subjected to RT-PCR with specific probes for various cytokines.

This experiment reveals a delay of approximately 24 hours in the production of cytokines in splenocytes derived from PYK2−/− mice (FIG. 3).

Thus, these experiments showed that macrophages and splenocytes from pyk2−/− mice produced decreased amounts of cytokines and chemokines, including IL-1α, IL-1β, IL-6, IL-10, TNF-α, GMCSF, IFN-γ, and MIP1α. Lower production of cytokines and chemokines such as TNF-α and MIP1-α (among others) results in attenuated recruitment and decreased activation of macrophages, T-cells and other hematopoietic and nonhematopoietic cells involved in the inflammatory response. In addition, macrophages from knockout mice had decreased motility in vitro.

Example III

Carageenen Model of Inflammation

In the subcutaneous carageenen air pouch model, a subcutaneous air pouch is surgically induced on the hind flank of the mouse. The air pouch is then filled with the immunogen carageenen, a substance that induces an inflammatory response.

Ten hours after carrageenan injection into wild type or PYK2−/− mice, tissue sections of the injected lesion were examined microscopically for the presence of infiltrating macrophages and neutrophils. Tissues from wild type +/+ and pyk2−/− air pouches were treated with Carageenen for 10 hours after injection. Samples were formalin-fixed and paraffin-embedded. Sections were stained with Hematoxylin and Eosin. The average number of infiltrating cells in wild type mice was 4.8×10$^6$ per injected area, while in the PYK2−/− mice there was an average of only 2.8×10$^6$ cells per injected area (FIG. 4a). Morphological examination of the infiltrating cells indicated that macrophages comprised approximately 70% of the infiltrate in wild-type mice but only 20% of the infiltrate in the PYK2−/− mice, the remaining cells were primarily neutrophils (FIG. 4b). These data show that the failure of PYK2−/− macrophages to migrate effectively in vitro is correlated with a striking deficit in inflammatory infiltration in vivo.

Example IV

Influenza Model of Inflammation

In the influenza model, infection with the influenza virus leads to an overwhelming pulmonary inflammatory response and eventually death.

Figure 5:
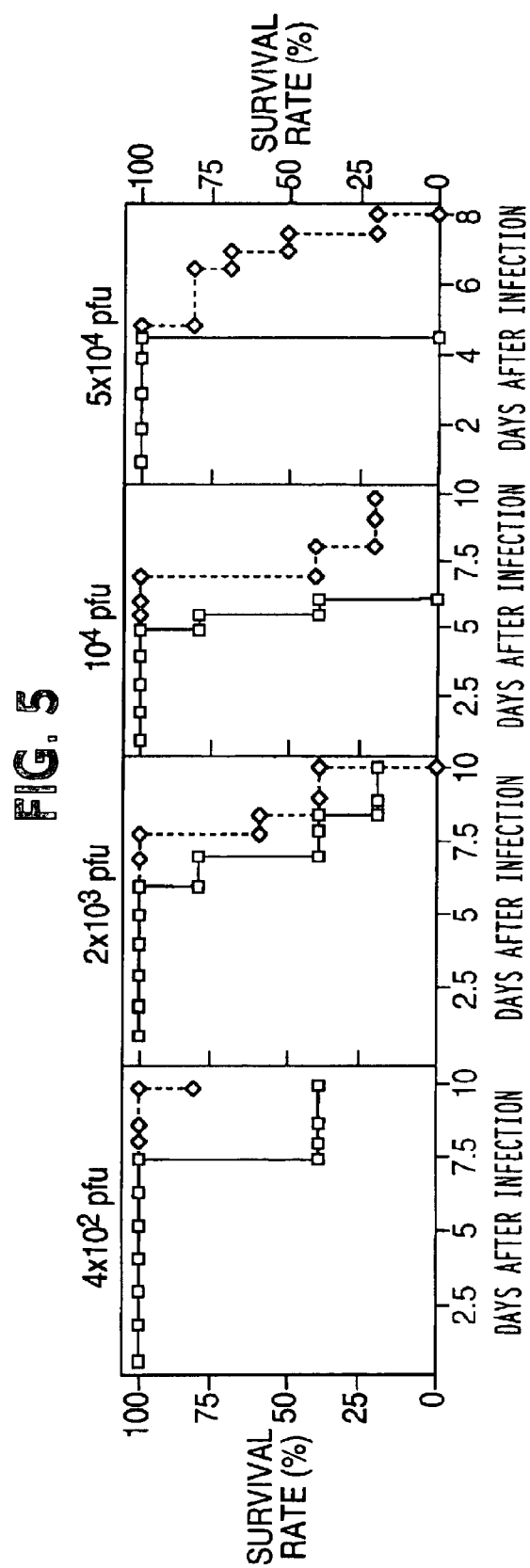
FIG. 5 demonstrates influenza virus-induced inflammation.
Figure 8A:
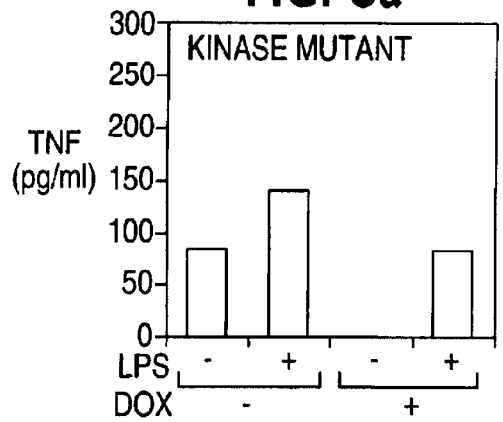
FIGS. 8a, 8b, 8c, and 8d compare the secretion of TNF-α by wild-type and kinase mutant P388D1 cells in response to activators of macrophage function or PYK2 activity.
Figure 8B:
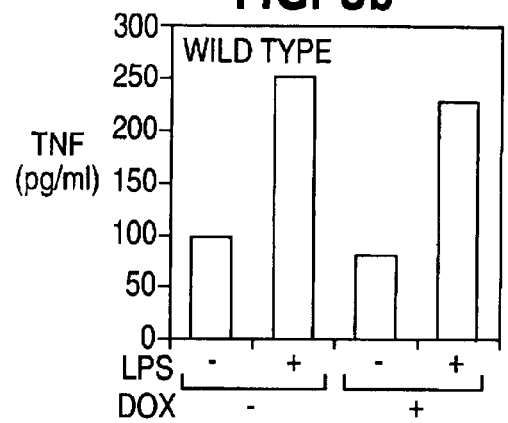
Figure 8C:
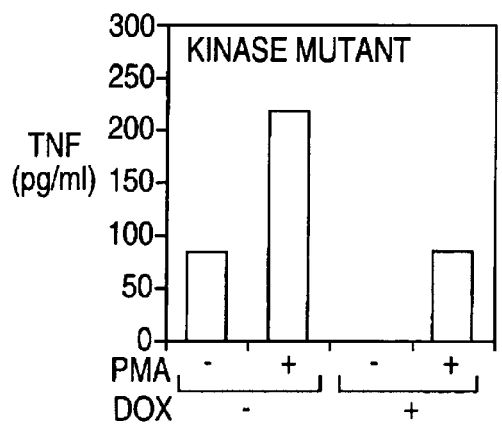
Figure 8D:
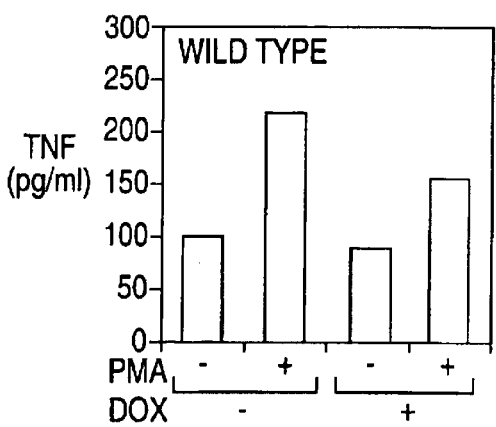

Influenza virus-induced inflammation in mice lungs was studied in lung sections from influenza virus-infected wild-type +/+ and Pyk2−/− mice 4 days after infection with the virus. Lungs were formalin-fixed and paraffin-embedded. Sections were stained with Hematoxylin and Eosin. Histologic sections were made of the lung from influenza virus-infected wild type +/+ and pyk2-/- mice 4 days after infection with the virus. FIG. 5 shows a time course of the survival of mice at different doses of influenza virus.

Histologic examination of the lungs of the knockout and control mice showed that in the lungs of the pyk2 knockout mice there was a significantly lower infiltration of inflammatory cells including PMNs (polymorphonuclear leukocytes), macrophages, and especially T-cells. Thus, on average the Pyk2 knockout mice exhibited decreased pulmonary cellular infiltrate and lived about 48 hours longer than wild-type mice after challenge with the influenza virus.

The attenuated cytokine response and migration defect in vitro correlate with the enhanced survival and decreased pulmonary cellular infiltrate in pyk2-/- mice following influenza challenge.

Example V

Analysis of Cytokine Production in PYK2 Dominant-Negative Mutants

To evaluate the role of PYK2 in mature macrophage cells that express wild-type PYK2, kinase inactive PYK2 protein was introduced into a normal macrophage cell line. Expression of the kinase inactive PYK2 functions as a "dominant-negative" inhibitor and abrogates the function of the endogenous wild-type PYK2 protein in these macrophages.

By "dominant negative mutant protein" is meant a mutant protein that interferes with the normal PYK2 signal transduction pathway. The dominant negative mutant protein contains the domain of interest (e.g., a PYK2 polypeptide or a NBP), but has a mutation preventing proper signaling, for example by preventing binding of a second domain from the same protein. One example of a dominant negative protein is described in Millauer, et al. *Nature* Feb. 10, 1994. Expression of the kinase inactive PYK2 protein decreased secretion of TNF-α in response to LPS, a physiologically relevant inducer of the inflammatory response.

Tyrosine phosphorylation of Pyk2 in response to LPS stimulation was measured in P388D1 cells. Cells were starved overnight in 0.5% serum and stimulated with LPS for variable time intervals (FIG. 6a). After stimulation, cells were washed, lysed, and immuno-precipitated with anti-Pyk2 antibody. Immuno-precipitates were then analyzed by western blotting. Tyrosine phosphorylated bands were detected with the anti- phosphotyrosine antibody 4G10. Maximal phosphorylation was observed after 30 minutes. Cells that had been pre-treated with either herbimycin A or genestein for 4 hours were stimulated with LPS for 30 minutes and analyzed as above (FIG. 6b). Tyrosine phosphorylation was diminished by pre-treatment with non-specific inhibitors of tyrosine phosphorylation.

The murine macrophage cell line (P388D1) was transfected with doxycycline inducible plasmids in order to study the effect of a dominant-negative Pyk2 protein on macrophage function. In the first transfection, a regulator plasmid was introduced and stable, drug-resistant clones were established. These were screened by transient transfection with a doxycycline-responsive, luciferase reporter plasmid. A range of luciferase responses was obtained from different clones. Two clones were selected (based upon their doxycycline response) and transfected with response plasmids containing either HA-tagged, wild-type Pyk2 or the kinase dead Pyk2 mutant (also HA tagged). After drug selection, stable clones were screened for expression of the appropriate protein by western blotting (FIG. 7).

TNF secretion in response to stimulation with either LPS (1 µg/mL) or PMA (1 µg/mL) by the doxycycline inducible clones is shown in FIG. 8. Induction in the presence of doxycycline was carried out for 48 hours followed by stimulation with LPS or PMA overnight (18 hours). Cells expressing the kinase-dead Pyk2 mutant had a blunted response to either LPS or PMA compared with cells expressing the wild-type Pyk2. Secreted TNF-α was measured by ELISA. Both LPS and PMA caused secretion of TNF-α. Secretion of TNF-α was inhibited by herbimycin A and genestein, which are non-specific inhibitors of tyrosine phosphorylation.

Example VI

PYK2-/- Macrophages Exhibit Abnormal Morphology, Enhanced Cell Polarization and Impaired Migration Macrophages normally express high levels of PYK2 and bearly detectable levels of FAK (Lipsky, et al. (1998) *J. Biol. Chem.* 273:11709–11713). It is possible that these cells might be more susceptible to the loss of PYK2. We have first compared the morphology of peritoneal macrophages from wild type or PYK2-/- mice 30 minutes after plating these cells on coverslips or on tissue-culture dishes. The micrographs showed that after adhesion wild-type macrophages adopt a typical round shape. Treatment of wild type macrophages with the chemokine SDF1α resulted in rapid induction of lamellipodia and enhancement of cell spreading. In contrast, most PYK2-/- macrophages displayed a flattened morphology with extensive membrane spreading even without chemokine treatment. Addition of SDF1α further increased the formation of pseudopodia as well as the appearance of long processes.

Morphological abnormalities and impaired cell migration in PYK2-/- macrophages were observed. PYK2-/- or wild type macrophages were plated on tissue culture dishes. Micrographs of unstimulated or SDF1a-stimulated macrophages were obtained and long multidirectional processes were observed. Multidirectional lamellipodia were seen in PYK2-/- but not in wild type macrophages. Micrographs of SDF-stimulated or unstimulated PYK2-/- or wild type macrophages plated on tissue culture dishes at different time points were obtained. The original point of cell movement was observed. Cell contraction and small lamellipodia were observed.

In view of the enhanced spreading with multiple pseudopodia and long processes as well as the enhanced substrate attachment displayed by PYK2-/- macrophages, we considered that macrophage migration in response to chemotactic stimulation could be impaired. We treated wild type and PYK2-/- macrophages with SDF1α and observed cell morphology and movement at ten minute intervals following chemokine stimulation. This experiment shows that within ten minutes wild-type macrophages become polarized, developing lamellipodia, on one side of the cell. At later time points (>20 minutes), the cell body moves in the direction established by the leading edge, detaching from the substrate at the trailing edge. In contrast, formation of new lamellipodia by PYK2-/- macrophages in response to SDF1α, was delayed as compared to wild-type cells. Furthermore, the cell body showed reduced ability to follow the leading edge and failed to detach from the substratum. Over time, the PYK2-/- macrophages extended lamellipodia in several directions with similar failure to detach from the substrate. Eventually, most PYK2-/- macrophages developed several pseudopodia-like processes with minimal net migration. Overall, PYK2-/- macrophages are able to form a leading edge in response to a chemotactic stimulus, albeit with slower kinetics. However, these cells are unable to move the cell body after the leading edge efficiently, and fail to detach the lagging edge from the substratum.

Example VII

Impairment in Contractile Force in PYK2-/- Macrophages Revealed by Optical Tweezer Analysis Microscopic observation of migrating macrophages revealed that PYK2-/- cells could extend lamellipodia but the cell body failed to flow into the newly formed leading edge. We suggested that the contractile activity of the cytoskelton in the lamellipodia was impaired in PYK2-/- macrophages. The contractile force was determined by measuring the rearward movement toward the nucleus of beads coated with recombinant fragment of fibronectin (FN type III domains 7-10) on lamellipodia in opposition to an immobilizing force generated by optical tweezers (Choquet, et al. (1997) Cell 88:39–48; Felsenfeld, et al. (1999) Nature Cell Biology 1:200–206). The velocity of rearward movement of the beads in opposition to this force represents a function of (i) the strength of association between the cytoskeleton and the integrins bound to the fibronectin on the bead, and (ii) the strength of traction force generated by the cytoskeleton itself (Choquet, et al. (1997) Cell 88:39–48; Sheetz, et al. (1998) Trends Cell Biol. 8:51–54). Immobilizing force by optical tweezers was applied to the beads on the lamellipodia of the cells and the movement of the bound beads was monitored. Representative plots of the distance of bead displacement versus time in wild type or PYK2-/- macrophages is presented in FIG. 9a.

The beads on the lamellipodia from wild type macrophages exhibited rearward movement and escaped from the force field of the laser trap. After chemokine stimulation, the velocity of bead movement on the lamellipodia of wild type macrophages was increased and the beads escaped more quickly. With the immobilizing force exerted by the optical tweezers, more than 50% of the beads that were attached to the lamellipodia of either stimulated or unstimulated wild type macrophages were able to escape from the force field of the optical trap. In contrast, beads bound to the lamellipodia of PYK2-/- macrophages did not exhibit rearward movement in presence or absence of chemokine stimulation (FIG. 9a). No beads that were attached to the lamellipodia of either stimulated or unstimulated PYK2-/- macrophages were able to escape from the optical trap (FIG. 9b). Overall, rearward movement, e.g. the contractile force generated by the cytoskeleton, is impaired in PYK2-/- macrophages in comparison to the contractile force generated in wild type macrophages.

Example VIII

Altered Cytoskeletal Organization in PYK2-/- Macrophages

We next examined the status of the cytoskeleton in PYK2-/- macrophages. Visualization of cells stained with fluorescent phalloidin revealed an increase of F-actin in membrane ruffles in PYK2-/- as compared to wild-type macrophages. Analysis of F-actin distribution by confocal microscopy revealed an increase in reorganized F-actin underneath the ruffles in PYK2-/- macrophages. When wild-type macrophages were placed in a chemotactic gradient, phalloidin staining revealed increase in the relative amount of F-actin at the edge of the cell in the region that is exposed to the greatest concentration of chemotactic signal. The distribution of F-actin in stimulated PYK2-/- macrophages was different, in these cells F-actin was distributed at multiple sites along the cell periphery. In migrating wild-type macrophages F-actin is continuously redistributed towards the leading edge of the cell. This redistribution of F-actin does not occur in PYK2-/- macrophages, probably resulting in the failure of the cells to become properly oriented in a chemotactic gradient.

Changes in cytoskeletal organization were observed in PYK2-/- macrophages. PYK2-/- and wild type macrophage were plated on tissue culture dishes, fixed by 4% paraformaldehyde and stained by fluorescently labeled phalloidin or anti-α-tubulin antibodies. Long multi-directional processes and membrane ruffles were observed in PYK2-/- macrophages. Top and side view of F-actin distribution were visualized with a confocal microscope. Reorganized F-actin in PYK2-/- macrophages was observed. The planes of the slices generated in top and side views. PYK2-/- and wild type macrophages were placed in MIP1 α gradient concentration for 60 min., fixed and then stained with fluorescently labeled phalloidin. The top left part of the field was exposed to the highest concentration of MIP1α. Regions with strong phalloidin labeling were observed. Nonstimulated or MIPα-stimulated macrophages were observed. Microtubules assembled at cell periphery in PYK2-/- macrophages were observed. Decreased intensity of MTOC was observed in PYK2-/- macrophages.

We have also examined the distribution of microtubules in wild type and PYK2-/- macrophages. It was proposed that microtubules play an important role in driving actin polymerization and leading-edge lamellipodia protrusion through specific rho-GTPases during cell migration (Waterman-Storer, et al. (1999) Nature Cell Biol. 1:45–50). The organization of microtubules in wild type or PYK2-/- macrophages was visualized by staining permaebilized cells with anti-tubulin antibodies. The results of the experiment show that the microtubules in PYK2-/- macrophages are more assembled than the microtubules in wild type macrophages. Upon chemokine stimulation, the microtubules of wild type macrophages radiate from the microtubules organizing center (MTOC) while PYK2-/- macrophages display long microtubules that are assembled at the cell periphery into longitudinal directions with decreased intensity towards the MTOC. The increased assembly of microtubules in the periphery of PYK2-/- macrophages could be linked to the enhancement in F-actin organization, extensive lamelliopodia formation in this region leading to altered cell polarization.

Example IX

Impairment in rho Activation in PYK2-/- Macrophages

Figure 10A:
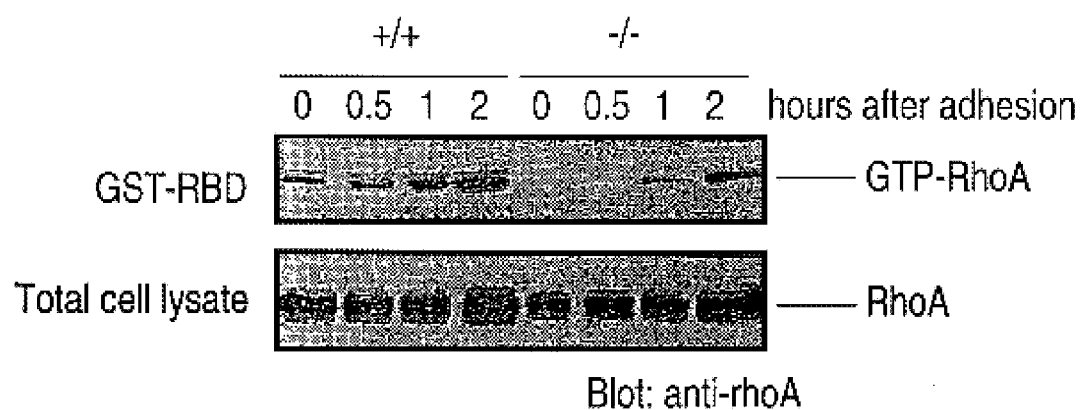

The rho family of small G-protein has been implicated in the control of cytoskelal organization leading to changes in cell morphology and cell migration (Ridley, et al. (1999) Biochem. Soc. Symp. 65:111–123). It was demonstrated that integrin-induced cell adhesion leads to the activation of rho (Ren, et al. (1999) EMBO J. 18:578–585). The activated GTP bound form of rho binds to effector proteins that are involved in the control of cytoskeletal organization and contraction of lamellipodia (Allen, et al. (1997) J. Cell Sci. 110:707–720; Maekawa, et al. (1999) Science 285:895–898). We have analyzed activation of rho in macrophages by applying a "pull-down" assay using a GST fusion protein containing the binding site from rhotekin for the GTP bound form of rho (Ren, et al. (1999) *EMBO J.* 18:578–585). The experiment presented in FIG. 10*a* shows fibronectininduced activation of rho as a function of time. In contrast, a similar experiment performed with PYK2–/– macrophages revealed reduced activation of rho in the mutant macrophages in response to integrin-induced cell adhesion (FIG. 10*a*).

The rho inhibitor C3 was microinjected together with fluorescently labeled dextran into wild type macrophages. After three hours incubation, the morphology of microinjected or non-injected cells was compared by Nomarsky microscopy. The injected macrophages were identified by their fluorescence. Microinjected macrophages, lamellipodia and long process were observed.

We have further examined the role played by rho in the control of macrophage morphology by microinjecting into these cells a specific inhibitor of rho designated C3 (Chardin, et al. (1989) *EMBO J.* 8:1087–1092) together with fluorescently labeled dextran as a specific marker. This experiment demonstrates that wild type macrophages microinjected with C3, showed a rapid and extensive cell spreading with strong ruffling and formation of long processes similar to the morphological changes seen in PYK2–/– macrophages. However, microinjection of C3 into PYK2–/– macrophages did not cause further changes to those seen in untreated PYK2–/– macrophages. Taken together, these experiments show that rho is activated upon adhesion of macrophages and that reduced activation of rho may be responsible for the enhanced spreading, ruffling and formation of long processes in PYK2–/– macrophages.

Example IX

Figure 10B:
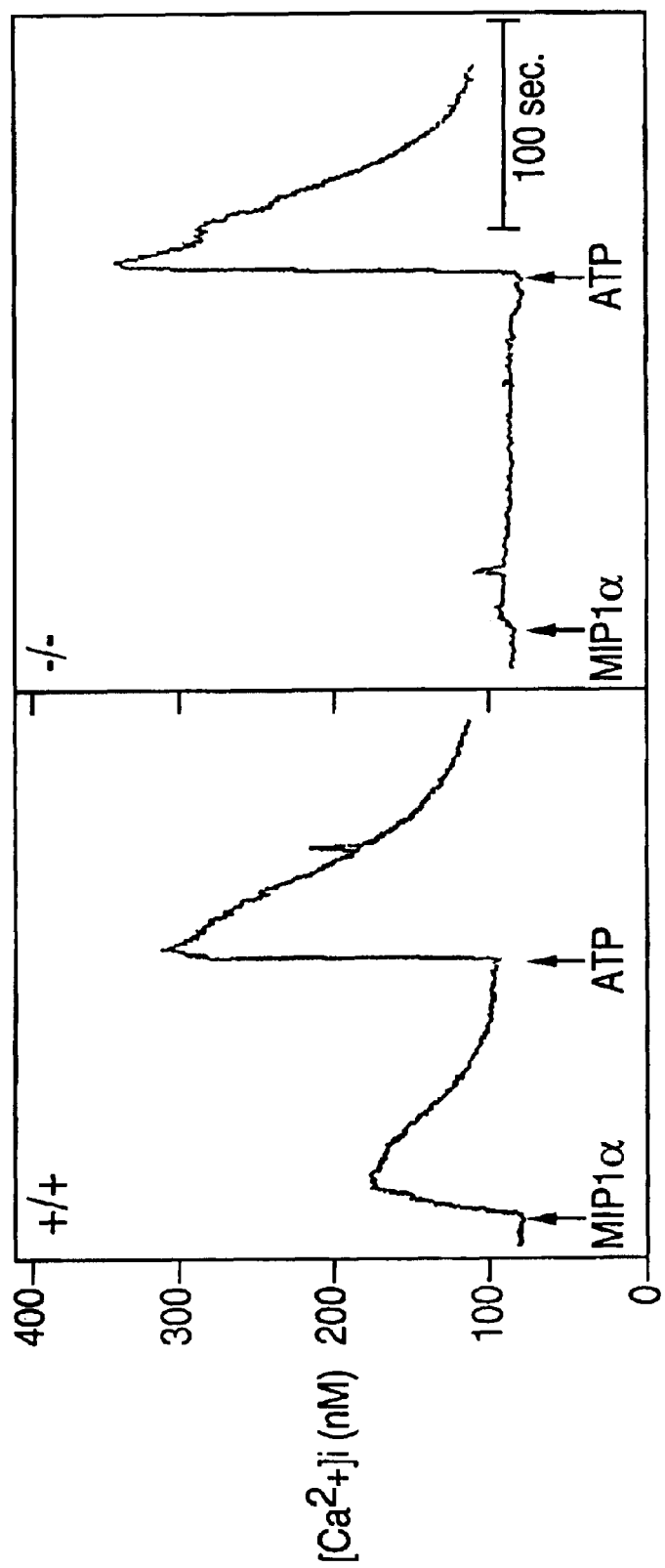

Reduced Intracellular Calcium Release and Ins(1,4, 5)P3 Production in PYK2Macrophages Calcium plays an important role in the control of a variety of intracellular events as well as in the control of cell shape, and cell movement (Lawson and Maxfield, 1995). We therefore measured cytoplasmic calcium release in single cells in response to MIP1α stimulation by using quantitative fluorescence microscopy of Fura-2 loaded cells. Treatment of wild type macrophages attached to cover slips showed maximum increase in cytoplasmic $[Ca^{+2}]$ concentration at approximately 300 nM of MIP1α. By contrast, PYK2–/– adherent macrophages did not show an obvious increase in $[Ca^{+2}]$ concentration (FIG. 10*b*). This experiment shows that PYK2 plays an important role in the control of MIP1α-induced $Ca^{+2}$ release in adherent macrophages. Defect in calcium release may contribute towards the failure of the cells to detach at the rear end leading to impairment in cell migration since proteins that regulate the degradation of focal contact components and disassembly of F-actin require calcium for their action (Witke, et al. (1995) *Cell* 81:41–51; Kulkarni, et al. (1999) *J. Biol Chem.* 274:21265–21275).

A significant proportion of intracellular $Ca^{+2}$ released in response to extracellular signals is mediated by inositol (1,4,5) triphosphate [Ins(1,4,5)$P_3$] production (Furuichi, et al. (1989) *Nature* 342:32–38). We therefore analyzed the production of Ins(1,4,5)$P_3$ in these cells. In this experiment wild type or PYK2–/– macrophages were labeled with [$^3$H] myo-inositol and then stimulated with MIP1α. At various times after MI1α stimulation the production of Ins(1,4,5)$P_3$ was determined by HPLC analysis (Falasca, et al. (1998) *EMBO J.* 17:414–422). Wild type macrophages showed a biphasic production of Ins(1,4,5)$P_3$ with peaks at 20 sec. and 2 min. after MIP1α stimulation. The experiment presented in FIG. 10*c* shows that Ins(1,4,5)$P_3$ production was severely reduced in PYK2–/– macrophages; the peak at 20 sec post stimulation was reduced by approximately 50% as compared to Ins(1,4,5,)$P_3$ production in wild type macrophages and no Ins(1,4,5)$P_3$ was generated after 2 min. of MIP1α stimulation (FIG. 10*c*). We have also detected impairment in the production of glycerophosphoinositol, phosphatidylinositol-3-phosphate and phosphatidylinositol-4-phosphate in PYK2–/– macrophages. These findings suggest that PYK2 deficiency may lead to a more general impairment in phosphatidyl inositol metabolism. We have previously shown that PYK2 forms a complex with a family of phosphatidylinositol transfer proteins designated Nirs both in vitro and in living cells (Lev, et al. (1999) *Mol. Cell. Biol.* 19:2278–2288). The interaction between PYK2 and the phosphatidylinositol transfer proteins and its absence in PYK2–/– macrophages may beresponsible for the impairment in phosphatidylinositol metabolism described.

Example X

Delayed Onset of Experimental Autoimmune Encephalomyelitis (EAE) and a More Severe Disease in PYK2–/– Mice Experimental Autoimmune Encephalomyelitis (EAE) is an inflammatory demyelinating disease of the central nervous system (CNS) which exhibits a predominantly mononuclear infiltrate, and is widely used as an animal model of multiple sclerosis (Zamvil and Steinman (1990) *Annu. Rev. Immunol.* 8:579–621). Since EAE is largely dependent on the activity of macrophages, we have compared the susceptibility of wild type or PYK2–/– mice to EAE by immunizing the mice with Myelin Oligodendrocyte Glycoprotein (MOG) (Johns, et al. (1995) *J. Immunol.* 154:5536–5541; Mendel, et al. (1995) *Eur. J. Immunol.* 25:1951–1959) and monitoring EAE progression. EAE was induced in PYK2–/– and wild type mice (129Sv) and the clinical course of the disease was monitored daily. As shown in FIG. 11*a*, both wild type and PYK2–/– mice are susceptible to MOG-induced EAE. However, the onset of EAE was delayed by approximately two days in PYK2 deficient mice as compared to the onset of the disease in wild-type mice. In several experiments PYK2–/– mice showed lower incidence of EAE; while not more than 75% of the PYK2–/– mice came down with the disease, virtually all wild-type mice became sick. However, the outcome of the disease was more severe in PYK2–/– mice, as compared to wild-type mice. For example, in the experiment depicted in FIG. 11, 50% of PYK2–/– mice (4 of 8) died whereas only one of 8 wild-type mice succumbed, the remaining mice showed partial or complete clinical recovery. EAE recovery may not be due entirely to a reduction in the proinflammatory stimulus. There is evidenece that cytokines and regulatory cells are actively involved in the clinical improvement (Welch, et al. (1980) *J. Immunol.* 125:186–189; Karpus, et al. (1991) *J. Immunol.* 146:1163–1168; Kennedy, et al. (1992) *J. Immunol.* 149:2496–2505); this process appears to be impaired in PYK2–/– mice.

Figure 11B:
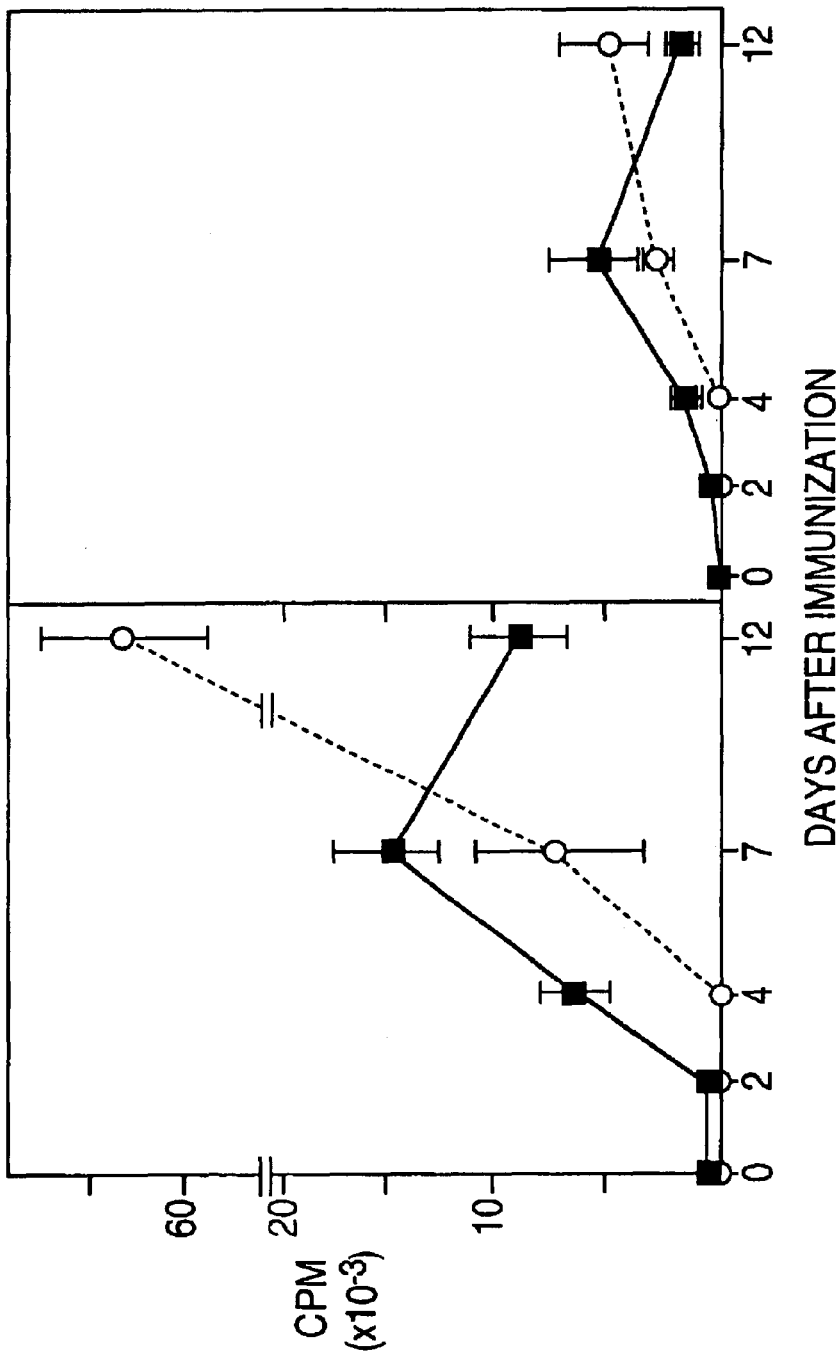

Next, draining lymphnode and central nervous system samples were prepared from wild type or PYK2 deficient mice at different times post induction. We have shown that T cells from wild type and mutant mice proliferate equally well in response to anti-CD3 stimulation at all time-points. However, the experiment presented in FIG. 11*b* shows that the proliferative response towards MOG was delayed in T cells from draining lymphnodes from PYK2–/– mice as compared to T cells from wild-type mice.

One skilled in the art would readily appreciate that the present invention is well adapted to carry out the objects and obtain the ends and advantages mentioned, as well as those inherent therein. The molecular complexes and the methods, procedures, treatments, molecules, specific compounds described herein are presently representative of preferred embodiments are exemplary and are not intended as limitations on the scope of the invention. Changes therein and other uses will occur to those skilled in the art which are encompassed within the spirit of the invention are defined by the scope of the claims.

It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed.

In particular, although some formulations described herein have been identified by the excipients added to the formulations, the invention is meant to also cover the final formulation formed by the combination of these excipients. Specifically, the invention includes formulations in which one to all of the added excipients undergo a reaction during formulation and are no longer present in the final formulation, or are present in modified forms.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described.

Other embodiments are within the following claims.

What is claimed is:

1. A method for treating progressive systemic sclerosis, comprising administering to a patient in need of such treatment one or more compounds selected from the group consisting of quinoxolines and indolinones.

2. The method of claim 1, wherein said patient is a mammal.

3. The method of claim 2, wherein said mammal is a human.

4. The method of claim 1, wherein said one or more compounds is one or more indolinones.

5. The method of claim 1, wherein said one or more compounds is in a pharmaceutically acceptable composition.

6. The method of claim 1, further comprising administering to said patient one or more compounds selected from the group consisting of tyrophostins, quinolines and quinazolines.

7. The method of claim 1, wherein said administering comprises a route selected from the group consisting of oral, rectal and parenteral.

8. The method of claim 7, wherein said route is selected from the group consisting of transmucosal, intestingal, intramuscular, subcutaneous, intravenous, intramedullary, intrathecal, intraventricular, intraperitoneal, intranasal, and intraocular.

9. The method of claim 7, wherein said administering by said parenteral route comprises a depot formulation.

* * * * *

SEQUENCE LISTING

```
<160> NUMBER OF SEQ ID NOS: 6

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 1
cgggatcctc atcatccatc ctaggaaaga                                    30

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 2
cgggaattcg tcgtagtccc agcagcgggt                                    30

<210> SEQ ID NO 3
<211> LENGTH: 10
<212> TYPE: PRT
<213> ORGANISM: Influenza virus

<400> SEQUENCE: 3

Tyr Pro Tyr Asp Val Pro Asp Tyr Ala Ser
  1               5                  10

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Primer
```

-continued

```
<400> SEQUENCE: 4
cacaatgtct tcaaacgcca c                                              21

<210> SEQ ID NO 5
<211> LENGTH: 63
<212> TYPE: DNA
<213> ORGANISM: Artificial Sequence
<220> FEATURE:
<223> OTHER INFORMATION: Description of Artificial Sequence: Primer

<400> SEQUENCE: 5
ggctctagat cacgatgcgt agtcagggac atcgtatggg ractctgcag gtgggtgggc    60
cag                                                                 63

<210> SEQ ID NO 6
<211> LENGTH: 31
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 6
caatgtagct gtcgcgacct gcaagaaaga c                                   31
```